(12) United States Patent
Reymond et al.

(10) Patent No.: US 10,774,077 B2
(45) Date of Patent: Sep. 15, 2020

(54) SUBSTITUTED 2-IMINO-1,3-THIAZOLIDIN-4-ONES AS N-ARACHIDONOYLETHANOLAMINE CELLULAR UPTAKE INHIBITORS

(71) Applicant: UNIVERSITAT BERN, Bern (CH)

(72) Inventors: Jean-Louis Reymond, Bulle (CH); Simon Nicolussi, Staad (CH); Jurg Gertsch, Schaffhausen (CH)

(73) Assignee: UNIVERSITAT BERN, Bern (CH)

( * ) Notice: Subject to any disclaimer, the term of this patent is extended or adjusted under 35 U.S.C. 154(b) by 0 days.

(21) Appl. No.: 16/546,328

(22) Filed: Aug. 21, 2019

(65) Prior Publication Data

US 2019/0382397 A1    Dec. 19, 2019

Related U.S. Application Data

(62) Division of application No. 16/221,634, filed on Dec. 17, 2018, now Pat. No. 10,392,377, which is a division of application No. 15/314,067, filed as application No. PCT/EP2015/061915 on Mar. 28, 2015, now Pat. No. 10,155,754.

(30) Foreign Application Priority Data

May 28, 2014  (EP) .................................... 14170449
Jun. 3, 2014   (EP) .................................... 14171024

(51) Int. Cl.
  *C07D 277/20*  (2006.01)
  *C07D 417/06*  (2006.01)
  *C07D 277/54*  (2006.01)

(52) U.S. Cl.
  CPC ......... *C07D 417/06* (2013.01); *C07D 277/54* (2013.01)

(58) Field of Classification Search
  CPC .................................................. C07D 277/20
  USPC ....................................................... 548/200
  See application file for complete search history.

(56) References Cited

U.S. PATENT DOCUMENTS

| 2,739,888 A | 3/1956 | Sawdey |
| 2,798,067 A | 7/1957 | Sawdey |

FOREIGN PATENT DOCUMENTS

| CN | 1882555 | 12/2006 |
| WO | 2005/016227 | 2/2005 |
| WO | 2005/054215 | 6/2005 |
| WO | 2007/059195 | 5/2007 |
| WO | 2008/100977 | 8/2008 |
| WO | 2009/137133 | 11/2009 |
| WO | 2011/135303 | 11/2011 |

OTHER PUBLICATIONS

Martin H. Bolli et al: "2-Imino-thiazolidin-4-one Derivatives as Potent, Orally Active S1P 1 Receptor Agonists", Journal of Medicinal Chemistry, vol. 53, No. 10, May 6, 2010, pp. 4198-4211.
Ottana R et al: "5-Arylidene-2-phenylimino-4-thiazolidinones as PTP1B and LMW-PTP inhibitors", Bioorganic & Medicinal Chemistry, Pergamon, GB, vol. 17, No. 5, 2009, pp. 1928-1937.
Weiqiang Lu et al: "HL005A new selective PPAR antagonist specifically inhibits the proliferation of MCF-7", Journal of Steroid Biochemistry and Molecular Biology, Elsevier Science Ltd., Oxford, GB, vol. 124, No. 3, Jan. 28, 2011, pp. 112-120.
Bettina Hofmann et al: "A Class of 5-Benzylidene-2-phenylthiazolinones with High Potency as Direct 5-Lipoxygenase Inhibitors", Journal of Medicinal Chemistry, vol. 54, No. 6, Mar. 24, 2011 pp. 1943-1947.
Ottana R et al:"5-Arylidene-2-imino-4-thiazolidinones: Design and synthesis of novel anti-inflammatory agents", Bioorganic & Medicinal Chemistry, Pergamon, GB, vol. 13, No. 13, 2005, pp. 4243-4252.
Ashton et al. "Endocannabinoid system dysfunction in mood and related disorders" Acta Psychiatr Scand 2011: 124: 250-261.
Aso et al. "Cannabinoids for treatment of Alzheimer's disease: moving toward the clinic" Frontiers in Pharm. 5: Article 37, 2014 (11 pages).
Berger et al "Targeting Fatty Acid Binding Protein (FABP) AnandamideTransporters—A Novel Strategy for Development of Anti-Inflammatory and Anti-Nociceptive Drugs" PLOS ONE; Dec. 2012 | vol. 7 | Issue 12, 12 pages.
Boll, "2-Imino-thiazolidin-4-one Derivatives as Potent, Orally Active S1P1 Receptor Agonists" J. Med. Chem. 2010, 53, 4198-4211.

(Continued)

*Primary Examiner* — Douglas M Willis
(74) *Attorney, Agent, or Firm* — JMB Davis Ben-David

(57) ABSTRACT

The invention relates to a compound comprising the following general formula (1):

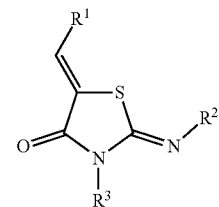

and said compound for use as a medicament, in particular for use in the treatment psychiatric or neurological disorders and inflammation, in particular neuroinflammation: (formula 1) wherein each of R1, R2 and R3 are selected independently from each other from alkyl, alkoxy, alkenyl, alkynyl, cycloalkyl, aryl, heterocycle, or heteroaryl.

19 Claims, No Drawings

(56) References Cited

OTHER PUBLICATIONS

Chicca, "Evidence for Bidirectional Endocannabinoid Transport across Cell Membranes" The Journal of Biological Chemistry vol. 287, No. 41, pp. 34660-34682, Oct. 5, 2012.
Chicca, "Functionalization of β-Caryophyllene Generates Novel Polypharmacology in the Endocannabinoid System" ACS Chem. Biol. 2014, 9, 1499-1507.
Correa, "The Endocannabinoid Anandamide:From Immunomodulation to Neuroprotection. Implications for Multiple Sclerosis" Vitamins and Hormones, vol. 81, Elsevier, 2009, 207-230.
De Lago "UCM707, an inhibitor of the anandamide uptake, behaves as a symptom control agent in models of Huntington's disease and multiple sclerosis, but fails to delay/arrest the progression of different motor-related disorders" European Neuropsychopharmacology (2006) 16, 7-18.
Fowler "Selective inhibition of anandamide cellular uptake versus enzymatic hydrolysis—a difficult issue to handle" European Journal of Pharmacology 492 (2004) 1-11.
Fowler "Transport of endocannabinoids across the plasma membrane and within the cell" FEBS Journal 280 (2013) 1895-1904.
Hasanein "Effects of the Endocannabinoid Transport Inhibitors AM404 and UCM707 on Diabetic Neuropathy in Rats" Clinical and Experimental Pharmacology and Physiology (2009) 36, 1127-1131.
Hofmann, "Marijuana, endocannabinoids, and epilepsy: Potential and challenges for improved therapeutic intervention" Experimental Neurology 244 (2013) 43-50.
Kaczocha "Inhibition of Fatty Acid Binding Proteins Elevates Brain Anandamide Levels and Produces Analgesia" PLOS ONE Apr. 2014 | vol. 9 | Issue 4, 10 pages.
Lopez-Rodriguez "Design, Synthesis and Biological Evaluation of Novel Arachidonic Acid Derivatives as Highly Potent and Selective Endocannabinoid Transporter Inhibitors" J. Med. Chem. 2001, 44, 4505-4508.
Lopez-Rodriguez "Design, synthesis and biological evaluation of new endocannabinoid transporter inhibitors" European Journal of Medicinal Chemistry 38 (2003) 403-412.
Loría "An endocannabinoid tone limits excitotoxicity in vitro and in a model of multiple sclerosis" Neurobiology of Disease 37 (2010) 166-176.
Marsicano "CB1 Cannabinoid Receptors and On-Demand Defense Against Excitotoxicity" Science, 302: 84-88. 2003.
Murillo-Rodríguez, "The Anandamide Membrane Transporter Inhibitor, VDM-11, Modulates Sleep and c-Fos Expression in the Rat Brain" Neuroscience 157 (2008) 1-11.
Murillo-Rodríguez, "The administration of endocannabinoid uptake inhibitors OMDM-2 or VDM-11 promotes sleep and decreases extracellular levels of dopamine in rats" Physiology & Behavior 109 (2013) 88-95.
Nicolussi, "Guineensine is a novel inhibitor of endocannabinoid uptake showing cannabimimetic behavioral effects in BALB/c mice" Pharmacological Research 80 (2014) 52-65.
Nicolussi, "Endocannabinoid Transport Revisited" Vitamins and Hormones, vol. 98 2015 Elsevier pp. 441-485.
Ortar "Novel selective and metabolically stable inhibitors of anandamide cellular uptake" Biochemical Pharmacology 65(2003)1473-1481.
Ortega-Gutiérrez, "Activation of the endocannabinoid system as a therapeutic approach in a murine model of multiple sclerosis" The FASEB Journal express article 10.1096/fj.04-2464fje. Published online Jun. 7, 2005.
Pacher, "The Endocannabinoid System as an Emerging Target of Pharmacotherapy" Pharmacol Rev 58:389-462, 2006.
Scherma, "The anandamide transport inhibitor AM404 reduces the rewarding effects of nicotine and nicotine induced dopamine elevations in the nucleus accumbens shell in rats" British Journal of Pharmacology (2012) 165 2539-2548.
Zhou, "Design, Synthesis, Cytoselective Toxicity, Structure-Activity Relationships, and Pharmacophore of Thiazolidinone Derivatives Targeting Drug-Resistant Lung Cancer Cells" J. Med. Chem. 2008, 51, 1242-1251.
Jordan, V. Craig. "Tamoxifen: a most unlikely pioneering medicine." Nature reviews Drug discovery 2.3 (2003): 205.
Hackam, Daniel G., and Donald A. Redelmeier. "Translation of research evidence from animals to humans." Jama 296.14 (2006): 1727-1732.
Norman, Derek D., et al. "Autotaxin inhibition: development and application of computational tools to identify site-selective lead compounds." Bioorganic & medicinal chemistry 21.17 (2013): 5548-5560.
NPL: Anonymous: "Natural eutectic salts catalyzed one-pot synthesis of 5-arylidene-2-i mi no-4-thiazolidinones I SpringerLink", Jul. 19, 2012 (Jul. 19, 2012).
Brincat, J.P., Carosati, E., Sabatini, S., Manfroni, G., Fravolini, A., Raygada, J.L., Patel, D., Kaatz, G.W. and Cruciani, G., 2010. Discovery of novel inhibitors of the NorA multidrug transporter of *Staphylococcus aureus*. Journal of medicinal chemistry, 54(1), pp. 354-365.
English translation of Notification of Reasons for Refusal of corresponding JP Patent Application No. JP 2016/569730.
CAS Registry No. 866419-78-5; STN Entry Date Oct. 31, 2005; 3-cyclohexyl-2-(cyclohexylimino)-5-[(2,3-dihydro-1,4-benzodioxin-6-yl)methylene]-4-thiazolidinone. 1 page.
CAS Registry No. 740870-50-2; STN Entry Date Sep. 7, 2004; 5-[(2,3-dihydro-1,4-benzodioxin-6-yl) methylene]-3-(2-methoxyethyl)-2- (phenylimino)-4-thiazolidinone. 1 page.
CAS Registry No. 676588-57-1; STN Entry Date Apr. 25, 2004; 5-[(2,3-dihydro-1,4-benzodioxin-6-yl) methylene]-3-methyl-2-[[4-(4-morpholinyl)phenyl]imino]-4-thiazolidinone. 1 page.
CAS Registry No. 345339-01-7; STN Entry Date Jul. 11, 2001; 3-cyclopentyl-2-(phenylimino)-5-[(5,6,7,8-tetrahydro-3-methoxy-2-naphthalenyl)methylene]-4-thiazolidinone. 1 page.
Excerpt from Australian Search Report of corresponding Australian Patent Application No. AU2015265865. 8 pages.

SUBSTITUTED 2-IMINO-1,3-THIAZOLIDIN-4-ONES AS N-ARACHIDONOYLETHANOLAMINE CELLULAR UPTAKE INHIBITORS

CROSS-REFERENCE TO RELATED APPLICATIONS

This is a divisional of U.S. patent application Ser. No. 16/221,634 filed Dec. 17, 2018, which is a divisional of U.S. patent application Ser. No. 15/314,067 filed Nov. 26, 2016, and now issued as U.S. Pat. No. 10,155,754; which was the US national stage of International Patent Application No. PCT/EP2015/061915, filed May 28, 2015, and which in turn claimed the benefit of EP Patent Application Nos. 14171024.4 filed on Jun. 3, 2014 and 14170449.4 filed on May 28, 2014. The contents of the foregoing patent applications are incorporated by reference herein in their entirety.

FIELD OF THE INVENTION

The present invention relates to a class of thiazolidinone derivatives as anandamide cellular uptake inhibitors and their use in the treatment of psychiatric or neurological disorders and inflammation, in particular neuroinflammation.

BACKGROUND OF THE INVENTION

The endocannabinoid system (ECS) is a lipid signaling system comprising endocannabinoids (ECs), which are lipids derived from arachidonic acid, the G-protein-coupled cannabinoid receptors CB1 and CB2, as well as several other actual and potential physiological targets involved in the synthesis, transport and degradation of ECs. The major ECs are 2-arachidonoylglycerol (2-AG) and N-arachidonoyl ethanolamide (AEA; anandamide) which modulate synaptic transmission by retrograde signaling via CB1 receptors and exert potent immunomodulatory effects via both CB1 and CB2 receptors. The ECS has been implicated in physiological and pathophysiological conditions including inflammation, pain, psychiatric disorders and metabolic reprogramming. The ECS provides a primary on-demand protection system against acute excitotoxicity in the central nervous system (CNS) (Marsicano et al., 2003, Science, 302, 84-8.)

Therapeutic strategies within the ECS include the use of cannabinoid receptor agonists and antagonists, blockage of hydrolytic enzymes degrading ECs, such as fatty acid amide hydrolase (FAAH) and monoacylglycerol lipase (MAGL), as well as inhibition of EC cell membrane trafficking. Although so far no membrane protein for EC transport has been identified, several lines of evidence suggest a facilitated membrane transport involving both membrane and cytoplasmic targets (Chicca et al., 2012, J Biol Chem. 287, 36944-67; Fowler C J., 2013, FEBS J., 280:1895-904). The movement of AEA across the cell is affected by the concentration gradient enhanced by rapid intracellular hydrolysis of AEA catalyzed by FAAH. Therefore, FAAH plays a key role in AEA cellular uptake by generating an inward concentration gradient for AEA, which is the major driving force for its cellular uptake.

Using the commercially available AEA uptake inhibitors UCM707, OMDM-2 and LY2183240 evidence for bidirectional transport of both AEA and 2-AG across cell membranes, as well as a common mechanism of cellular membrane transport for all arachidonate-based ECs was recently provided (Chicca et al., 2012, J Biol Chem. 287, 36944-67).

Since all of the available inhibitors are only moderately potent and show low selectivity towards AEA transport inhibition over FAAH inhibition or other cytoplasmic targets, investigations of the mechanisms of AEA and 2-AG cellular uptake are hampered by a lack of adequate tools. As indicated by a recent study (Nicolussi et al., Pharmacol Res., 2014, 80:52-65), the CNS pharmacology of inhibitors of endocannabinoid breakdown and inhibitors of endocannabinoid membrane transport is distinctly different and that inhibition of FAAH and AEA cellular uptake, respectively, can be independent from each other. Prior art has shown the use of Dodeca-2E,4E-diene amides as specific AEA cellular uptake inhibitors as anti-inflammatory agents in skin (WO 2010136221 A1). The potential therapeutic value of specific AEA cellular uptake inhibitors to treat CNS related diseases remains largely unknown. In a murine model of multiple sclerosis, the AEA cell membrane transport and FAAH inhibitor UCM707 showed beneficial effects by reducing microglial activation (Ortega-Gutierrez et al., 2005, FASEB J., 19, 1338-40). Using UCM707, it was shown that an increased AEA tone limits excitotoxicity in vitro and in a model of multiple sclerosis (Loria et al., 2010, Neurobiol Dis., 37, 166-76). The non-specific AEA cellular uptake and FAAH inhibitor AM404 was shown to reduce the rewarding effects of nicotine and nicotine-induced dopamine elevations in the nucleus accumbens shell in rats (Sherma et al., Br J Pharmacol., 2012, 165, 2539-48). The non-specific AEA cell membrane transport inhibitor VDM-11 was shown to modulate sleep and c-Fos expression in the rat brain (Murillo-Rodriguez et al., Neuroscience, 2008, 157, 1-11). The administration of AEA cell membrane transport inhibitors OMDM-2 or VDM-11 was shown to promote sleep and decreases extracellular levels of dopamine in rats (Murillo-Rodriguez et al., Physiol Behav. 2013, 109, 88-95). UCM707 was shown to behave as a symptom control agent in models of Huntington's disease and multiple sclerosis, but failed to delay/arrest the progression of different motor-related disorders (de Lago et al., Eur Neuropsychopharmacol., 2006, 16, 7-18). As shown by a study using UCM707 and AM404, AEA transport inhibitors may have potential in the treatment of painful diabetic neuropathy (Hasanein and Soltani, 2009, Clin Exp Pharmacol Physiol. 36, 1127-31). Targeting fatty acid binding protein (FABP) intracellular AEA carriers has recently been suggested to be a strategy to generate anti-inflammatory and anti-nociceptive drugs (Berger et al., 2012, PLoS One., 7(12):e50968). However, the pharmacology between the inhibition of AEA cell membrane transport and the inhibition of cytoplasmic carriers is expected to be different, as exemplified by the fact that FABP5 inhibitors do apparently not show the same degree of cannabimimetic effects observed with the potent AEA cell membrane transport inhibitor guineensine (Kaczocha et al., PLoS One. 2014, 9(4):e94200; Nicolussi et al., 2014, Pharmacol Res., 80, 52-65).

Overall, there is a need for novel inhibitors of AEA cell membrane transport with superior specificity and potency to address CNS and inflammation related diseases involving aberrant endocannabinoid tone or in which AEA cellular uptake inhibition can target pathophysiological conditions. Given the fact that AEA and other endocannabinoids are involved in both synaptic processes via retrograde signaling and immunomodulatory processes, specific inhibitors of AEA cell membrane transport are expected to exert therapeutic effects in neuropsychiatric diseases involving neuroinflammation. When the degradation of AEA and other endocannabinoids is blocked, for example by covalent inhibition of FAAH, the resulting intracellular accumulation of AEA (Chicca et al., 2012, J Biol Chem., 287, 36944-67) is expected to potentially also have proinflammatory effects via oxygenation of AEA and possibly other endocannabinoids by cyclooxygenase-2 (discussed in Chicca et al, 2014, ACS Chem Biol, http://pubs.acs.org/doi/abs/10.1021/cb500177c). Therefore, the inhibition of degradation of AEA and the inhibition of cell membrane transport are distinct pharmacological interventions. Moreover, specific inhibition of AEA cell membrane transport, unlike inhibition of FAAH or cytoplasmic carriers, is expected to differentially modulate the AEA tone without leading to activation of TRPV1 channels via intracellular AEA accumulation.

Our attention, therefore, is focused on the identification of new class of molecules able to specifically inhibit AEA cellular uptake that do not affect hydrolytic enzymes, such as the serine hydrolase FAAH. We show that these compounds trigger cannabimimetic behavioral effects and inhibit inflammation, in particular neuroinflammation.

The present invention relates to thiazolidinone derivatives and their use for the treatment of psychiatric or neurological disorders and inflammation, in particular neuroinflammation. The use of the compounds of the invention in a method for treatment of psychiatric or neurological disorders is related to attenuation of neuroinflammation and neuronal retrograde signaling mediated via AEA and other endocannabinoids. In example, such diseases include multiple sclerosis, epilepsy, Alzheimers disease, bipolar diseases, schizophrenia, sleeping disorders, and spinal cord injury (Ashton and Moore, Acta Psychiatr Scand. 2011, 124, 250-61; Aso and Ferrer I, Front Pharmacol., 2014, 5, 37; Correa et al. Vitam Horm. 2009, 81, 207-30; Hofmann and Frazier, Exp Neurol. 2013, 244, 43-50; Pacher et al., Pharmacol Rev., 2006, 58, 389-462).

SUMMARY OF THE INVENTION

A first aspect of the invention relates to a compound characterized by a general formula 1

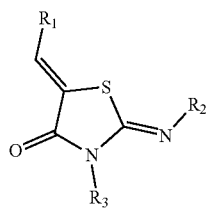

(formula 1)

wherein
$R^1$ is selected from
a substituted or unsubstituted heterocycle, in particular a substituted or unsubstituted $C_3$-$C_{10}$ heterocycle, or
a substituted or unsubstituted heteroaryl, in particular a substituted or unsubstituted $C_5$-$C_{10}$ heteroaryl, and
each of $R^2$ and $R^3$ are selected independently from each other from
a substituted or unsubstituted alkyl, in particular a substituted or unsubstituted $C_1$-$C_{12}$ alkyl,
a substituted or unsubstituted alkoxy, in particular a substituted or unsubstituted $C_1$-$C_{12}$ alkoxy,
a substituted or unsubstituted alkenyl, in particular a substituted or unsubstituted $C_2$-$C_{12}$ alkenyl,
a substituted or unsubstituted alkynyl, in particular a substituted or unsubstituted $C_2$-$C_{12}$ alkynyl,
a substituted or unsubstituted cycloalkyl, in particular a substituted or unsubstituted $C_3$-$C_{10}$ cycloalkyl,
a substituted or unsubstituted aryl, in particular a substituted or unsubstituted $C_6$-$C_{10}$ aryl,
a substituted or unsubstituted heterocycle, in particular a substituted or unsubstituted $C_3$-$C_{10}$ heterocycle, or
a substituted or unsubstituted heteroaryl, in particular a substituted or unsubstituted $C_5$-$C_{10}$ heteroaryl.

A second aspect of the invention relates to a compound characterized by a general formula 1

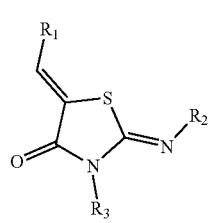

(formula 1)

wherein
$R^2$ is selected from
a substituted or unsubstituted alkyl, in particular a substituted or unsubstituted $C_1$-$C_{12}$ alkyl,
a substituted or unsubstituted alkoxy, in particular a substituted or unsubstituted $C_1$-$C_{12}$ alkoxy,
a substituted or unsubstituted alkenyl, in particular a substituted or unsubstituted $C_2$-$C_{12}$ alkenyl,
a substituted or unsubstituted alkynyl, in particular a substituted or unsubstituted $C_2$-$C_{12}$ alkynyl,
a substituted or unsubstituted cycloalkyl, in particular a substituted or unsubstituted $C_3$-$C_{10}$ cycloalkyl,
a substituted or unsubstituted aryl, in particular a substituted or unsubstituted $C_6$-10 aryl,
a substituted or unsubstituted heterocycle, in particular a substituted or unsubstituted $C_3$-$C_{10}$ heterocycle, or
a substituted or unsubstituted heteroaryl, in particular a substituted or unsubstituted $C_5$-$C_{10}$ heteroaryl, and
each of $R^1$ and $R^3$ are selected independently from each other from
a substituted or unsubstituted alkyl, in particular a substituted or unsubstituted $C_1$-$C_{12}$ alkyl,
a substituted or unsubstituted alkoxy, in particular a substituted or unsubstituted $C_1$-$C_{12}$ alkoxy,
a substituted or unsubstituted alkenyl, in particular a substituted or unsubstituted $C_2$-$C_{12}$ alkenyl,
a substituted or unsubstituted alkynyl, in particular a substituted or unsubstituted $C_2$-$C_{12}$ alkynyl,
a substituted or unsubstituted cycloalkyl, in particular a substituted or unsubstituted $C_3$-$C_{10}$ cycloalkyl,
a substituted or unsubstituted aryl, in particular a substituted or unsubstituted $C_6$-$C_{10}$ aryl,
a substituted or unsubstituted heterocycle, in particular a substituted or unsubstituted $C_3$-$C_{10}$ heterocycle, or
a substituted or unsubstituted heteroaryl, in particular a substituted or unsubstituted $C_5$-$C_{10}$ heteroaryl.

A third aspect of the invention relates to a compound characterized by a general formula 1

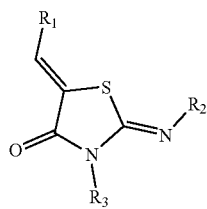

(formula 1)

wherein
R³ is selected from
  a substituted or unsubstituted alkyl, in particular a substituted or unsubstituted $C_1$-$C_{12}$ alkyl,
  a substituted or unsubstituted alkoxy, in particular a substituted or unsubstituted $C_1$-$C_{12}$ alkoxy,
  a substituted or unsubstituted alkenyl, in particular a substituted or unsubstituted $C_2$-$C_{12}$ alkenyl,
  a substituted or unsubstituted alkynyl, in particular a substituted or unsubstituted $C_2$-$C_{12}$ alkynyl,
  a substituted or unsubstituted cycloalkyl, in particular a substituted or unsubstituted $C_3$-$C_{10}$ cycloalkyl,
  a substituted or unsubstituted aryl, in particular a substituted or unsubstituted $C_6$-10 aryl,
  a substituted or unsubstituted heterocycle, in particular a substituted or unsubstituted $C_3$-$C_{10}$ heterocycle, or
  a substituted or unsubstituted heteroaryl, in particular a substituted or unsubstituted $C_5$-$C_{10}$ heteroaryl, and
each of R¹ and R² are selected independently from each other from
  a substituted or unsubstituted alkyl, in particular a substituted or unsubstituted $C_1$-$C_{12}$ alkyl,
  a substituted or unsubstituted alkoxy, in particular a substituted or unsubstituted $C_1$-$C_{12}$ alkoxy,
  a substituted or unsubstituted alkenyl, in particular a substituted or unsubstituted $C_2$-$C_{12}$ alkenyl,
  a substituted or unsubstituted alkynyl, in particular a substituted or unsubstituted $C_2$-$C_{12}$ alkynyl,
  a substituted or unsubstituted cycloalkyl, in particular a substituted or unsubstituted $C_3$-$C_{10}$ cycloalkyl,
  a substituted or unsubstituted aryl, in particular a substituted or unsubstituted $C_6$-$C_{10}$ aryl,
  a substituted or unsubstituted heterocycle, in particular a substituted or unsubstituted $C_3$-$C_{10}$ heterocycle, or
  a substituted or unsubstituted heteroaryl, in particular a substituted or unsubstituted $C_5$-$C_{10}$ heteroaryl.

A fourth aspect of the invention relates to a compound characterized by the following general formula (1)

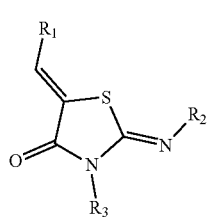

(formula 1)

wherein
R¹ is selected from
  a substituted or unsubstituted alkyl, in particular a substituted or unsubstituted $C_1$-$C_{12}$ alkyl,
  a substituted or unsubstituted alkoxy, in particular a substituted or unsubstituted $C_1$-$C_{12}$ alkoxy,
  a substituted or unsubstituted alkenyl, in particular a substituted or unsubstituted $C_2$-$C_{12}$ alkenyl,
  a substituted or unsubstituted alkynyl, in particular a substituted or unsubstituted $C_2$-$C_{12}$ alkynyl,
  a substituted or unsubstituted cycloalkyl, in particular a substituted or unsubstituted $C_3$-$C_{10}$ cycloalkyl,
  a substituted or unsubstituted aryl, in particular a substituted or unsubstituted $C_6$-$C_{10}$ aryl, and
each of R² and R³ are selected independently from each other from
  a substituted or unsubstituted alkyl, in particular a substituted or unsubstituted $C_1$-$C_{12}$ alkyl,
  a substituted or unsubstituted alkoxy, in particular a substituted or unsubstituted $C_1$-$C_{12}$ alkoxy,
  a substituted or unsubstituted alkenyl, in particular a substituted or unsubstituted $C_2$-$C_{12}$ alkenyl,
  a substituted or unsubstituted alkynyl, in particular a substituted or unsubstituted $C_2$-$C_{12}$ alkynyl,
  a substituted or unsubstituted cycloalkyl, in particular a substituted or unsubstituted $C_3$-$C_{10}$ cycloalkyl,
  a substituted or unsubstituted aryl, in particular a substituted or unsubstituted $C_6$-$C_{10}$ aryl,
  a substituted or unsubstituted heterocycle, in particular a substituted or unsubstituted $C_3$-$C_{10}$ heterocycle, or
  a substituted or unsubstituted heteroaryl, in particular a substituted or unsubstituted $C_5$-$C_{10}$ heteroaryl.

A fifth aspect of the invention relates to a compound according to the first, second, third or fourth aspect of the invention for use as a medicament.

A sixth aspect of the invention relates to a compound according to the first, second, third or fourth aspect of the invention for use in the treatment of psychiatric or neurological disorders and inflammation, in particular neuroinflammation.

A seventh aspect of the invention relates to a pharmaceutical preparation for use in the treatment of psychiatric or neurological disorders and inflammation, in particular neuroinflammation, comprising at least one compound according to the the first, second, third or fourth aspect of the invention.

A eight aspect of the invention relates to the compound of the first aspect, particularly the first, second and third sub aspect, of the invention for use as an endocannabinoid system modulator.

A ninth aspect of the invention relates to the compound of the first aspect, particularly the first, second and third sub aspect, of the invention for use as an AEA uptake Inhibitor.

DETAILED DESCRIPTION OF THE INVENTION

The compounds of the invention may also be used as an analgesic. Reference is made to the figures and experimental section.

The term "substituted" refers to the addition of a substituent group to a parent moiety.

"Substituent groups" can be protected or unprotected and can be added to one available site or to many available sites in a parent moiety. Substituent groups may also be further substituted with other substituent groups and may be attached directly or by a linking group such as an alkyl, an amide or hydrocarbyl group to a parent moiety. "Substituent groups" amenable herein include, without limitation, halogen, oxygen, nitrogen, sulphur, hydroxyl, alkyl, alkenyl, alkynyl, acyl, carboxyl, aliphatic groups, alicyclic groups, alkoxy, substituted oxy, aryl, aralkyl, amino, imino, amido fluorinated compounds etc.

As used herein the term "alkyl," refers to a saturated straight or branched hydrocarbon moiety containing in particular up to 12 carbon atoms. Examples of alkyl groups include, without limitation, methyl, ethyl, propyl, butyl, isopropyl, n-hexyl, octyl, and the like. Alkyl groups typically include from 1 to about 12 carbon atoms ($C_1$-$C_{12}$ alkyl).

As used herein the term "cycloalkyl" refers to an interconnected alkyl group forming a saturated or unsaturated (or partially unsaturated) ring or polyring structure containing 3 to 10, particularly 5 to 10 carbon atoms. Examples of cycloalkyl groups include, without limitation, cyclopropane, cyclopentane, cyclohexane, norbornane, decaline or adamantan (Tricyclo[3.3.1.1]decan), and the like. Cycloalkyl groups typically include from 5 to 10 carbon atoms ($C_5$-$C_{10}$ cycloalkyl).

Alkyl or cycloalkyl groups as used herein may optionally include further substituent groups. A substitution on the cycloalkyl group also encompasses an aryl, a heterocycle or a heteroaryl substituent, which can be connected to the cycloalkyl group via one atom or two atoms of the cycloalkyl group.

As used herein the term "alkenyl," refers to a straight or branched hydrocarbon chain moiety containing in particular up to 12 carbon atoms and having at least one carbon-carbon double bond. Examples of alkenyl groups include, without limitation, ethenyl, propenyl, butenyl, 1-methyl-2-buten-1-yl, dienes such as 1,3-butadiene and the like. Alkenyl groups as used herein may optionally include further substituent groups.

As used herein the term "alkynyl," refers to a straight or branched hydrocarbon moiety containing in particular up to 12 carbon atoms and having at least one carbon-carbon triple bond. Examples of alkynyl groups include, without limitation, ethynyl, 1-propynyl, 1-butynyl, and the like. Alkynyl groups as used herein may optionally include further substituent groups.

As used herein the term "alkoxy," refers to an oxygen alkyl moiety containing in particular 1 to 12 carbon atoms comprising at least one oxygen moiety instead of a $CH_2$ moiety.

Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups. Furthermore, "alkoxy" groups include straight or branched ether groups (e.g. —$CH_2$—$CH_2$—O—$CH_3$) or polyether groups, which comprise several interconnected monomer alkoxy groups (e.g. —O—$CH_2$—$CH_2$—O—$CH_3$).

As used herein the term "heterocycle" refers to an interconnected alkyl group forming a saturated or unsaturated ring or polyring structure containing 3 to 10, particularly 5 to 10 carbon atoms in which at least one carbon atom is replaced with an oxygen, a nitrogen or a sulphur atom forming a nonaromatic structure. Heterocyclic groups as used herein may optionally include further substituent groups. A substitution on the heterocyclic group also encompasses an aryl, a cycloalkyl or a heteroaryl substituent, which can be connected to the heterocyclic group via one atom or two atoms of the heterocyclic group (comparable to indole).

As used herein the term "aryl" refers to a hydrocarbon with alternating double and single bonds between the carbon atoms forming an aromatic ring structure, in particular a six ($C_6$ to ten ($C_{10}$) membered ring or polyring structure. The term "heteroaryl" refers to aromatic structures comprising a five to ten membered ring or polyring structure, comparable to aryl compounds, in which at least one member is an oxygen or a nitrogen or a sulphur atom. Due to simplicity reasons they are denominated $C_5$ to $C_{10}$ heteroaryl, wherein at least one carbon atom is replaced with an oxygen, a nitrogen or a sulphur atom forming an aromatic structure. For example a $C_5$ heteroaryl comprises a five membered ring structure with at least one carbon atom being replaced with an oxygen, a nitrogen or a sulphur atom. Aryl or hetero aryl groups as used herein may optionally include further substituent groups. A substitution on the hetero aryl group also encompasses an aryl, a cycloalkyl or a heterocycle substituent, which can be connected to the hetero aryl via one atom or two atoms of the hetero aryl group (comparable to indole). The same applies to an aryl group.

As used herein "*" indicates a center of a E- or Z-isomer structure, which is located on the atom below the asterisk *.

According to a first aspect of the invention, the invention relates to a compound characterized by a general formula 1

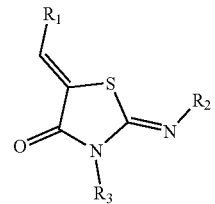

(formula 1)

wherein
$R^1$ is selected from
  a substituted or unsubstituted heterocycle, in particular a substituted or unsubstituted $C_3$-$C_{10}$ heterocycle, or
  a substituted or unsubstituted heteroaryl, in particular a substituted or unsubstituted $C_5$-$C_{10}$ heteroaryl, and
each of $R^2$ and $R^3$ are selected independently from each other from
  a substituted or unsubstituted alkyl, in particular a substituted or unsubstituted $C_1$-$C_{12}$ alkyl,
  a substituted or unsubstituted alkoxy, in particular a substituted or unsubstituted $C_1$-$C_{12}$ alkoxy,
  a substituted or unsubstituted alkenyl, in particular a substituted or unsubstituted $C_2$-$C_{12}$ alkenyl,
  a substituted or unsubstituted alkynyl, in particular a substituted or unsubstituted $C_2$-$C_{12}$ alkynyl,
  a substituted or unsubstituted cycloalkyl, in particular a substituted or unsubstituted $C_3$-$C_{10}$ cycloalkyl,
  a substituted or unsubstituted aryl, in particular a substituted or unsubstituted $C_6$-$C_{10}$ aryl,
  a substituted or unsubstituted heterocycle, in particular a substituted or unsubstituted $C_3$-$C_{10}$ heterocycle, or
  a substituted or unsubstituted heteroaryl, in particular a substituted or unsubstituted $C_5$-$C_{10}$ heteroaryl.

In some embodiments, $R^1$ comprises the general formula 2a' to 2j',

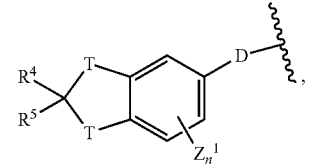

(2a')

-continued (2b')
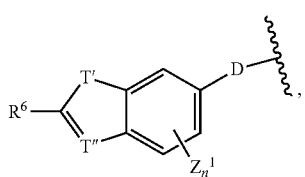

(2c')
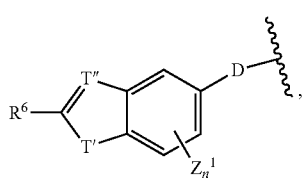

(2d')
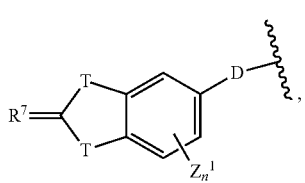

(2e')
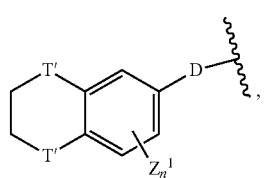

(2f')
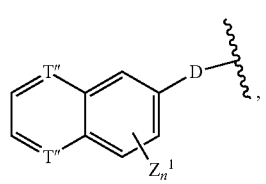

(2g')
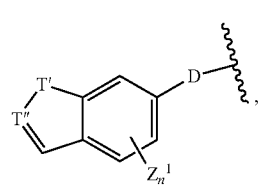

(2h')
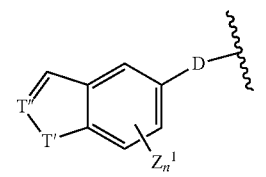

(2i')
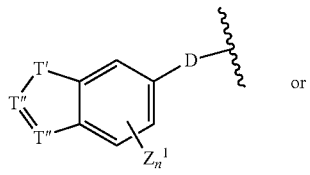
or

-continued (2j')
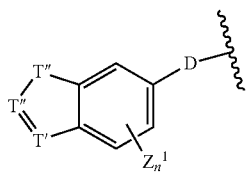

with D being a $C_1$ to $C_4$ alkyl,
with each T being selected independently from each other from —$CH_2$—, —NH—, —S—, —O—, —CHCH$_3$—, —C(CH$_3$)$_2$— or —NR—, in particular from NH, —S— or —O—, and
with T' being selected from —$CH_2$—, —NH—, —S—, —O—, —CHCH$_3$—, —C(CH$_3$)$_2$— or —NR$^c$—, and
with each T" being selected independently from each other from being selected from —CH— or =N—,
with $R^4$ and $R^5$ being selected independently from each other from —H, —F, —CH$_3$, —CH$_2$CH$_3$, —OCH$_3$, —CH$_2$CF$_3$, —CHFCF$_3$, —CF$_2$CF$_3$, —CHF$_2$, —CH$_2$F or —CF$_3$, in particular with $R^5$ and $R^6$ being selected independently from each other from H, —F or —CH$_3$, and
with $R^6$ being selected from —OH, —OCH$_3$, —OCH$_2$CH$_3$, —CH$_3$ or H,
with $R^7$ being selected from =NH, =S or =O, in particular from O, and
with n of $Z^1_n$ being 0, 1, 2 or 3, in particular n of $Z^1_n$ being 0 or 1, and with each $Z^1$ independently from any other $Z^1_n$ being selected from —F, —Cl, —Br, —I, CN, —$R^a$, —$OR^a$, —(CH$_2$)$_r$OR$^a$, —$SR^a$, —(CH$_2$)$_r$SR$^a$ or —$NR^a_2$, with each $R^a$ being selected independently from each other from H, a substituted or unsubstituted $C_1$-$C_8$ alkyl, in particular $C_1$-$C_4$ alkyl, a substituted or unsubstituted $C_2$-$C_8$ alkenyl, in particular $C_2$-$C_4$ alkenyl, or a substituted or unsubstituted $C_2$-$C_8$ alkynyl, in particular $C_2$-$C_4$ alkynyl, with r being 1, 2, 3 or 4, in particular r is 1,
with $R^c$ being —CH$_2$OH, —CH$_3$, —CH$_2$CH$_3$, —CH$_2$CH$_2$CH$_3$, —CH(CH$_3$)$_2$, —CH$_2$CF$_3$, —CHFCF$_3$, —CF$_2$CF$_3$, —CHF$_2$, —CH$_2$F, —CF$_3$.

In some embodiments, $R^1$ comprises the general formula 2a to 2j, (2a)
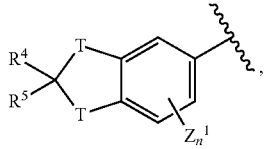

(2b)
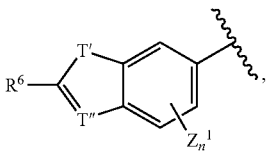

(2c)
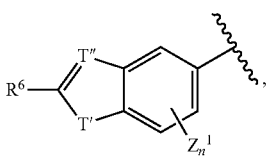

-continued (2d)

(2e)

(2f)

(2g)

(2h)

(2i)

(2j)

with each T being selected independently from each other from —CH$_2$, —NH, —S, —O, —CHCH$_3$, —C(CH$_3$)$_2$ or —NR$^c$, in particular from NH, —S or —O, and with T' being selected from —CH$_2$, —NH, —S, —O, —CHCH$_3$, —C(CH$_3$)$_2$ or —NR, and with each T" being selected independently from each other from being selected from —CH or =N, with R$^4$ and R$^5$ being selected independently from each other from —H, —F, —CH$_3$, —CH$_2$CH$_3$, —OCH$_3$, —CH$_2$CF$_3$, —CHFCF$_3$, —CF$_2$CF$_3$, —CHF$_2$, —CH$_2$F or —CF$_3$, in particular with R$^5$ and R$^6$ being selected independently from each other from H, —F or —CH$_3$, and with R$^6$ being selected from —OH, —OCH$_3$, —OCH$_2$CH$_3$, —CH$_3$ or H, with R$^7$ being selected from =NH, =S or =O, in particular from 0, and with n of Z$^1_n$ being 0, 1, 2 or 3, in particular n of Z$^1_n$ being 0 or 1, and with each Z$^1$ independently from any other Z$^1_n$ being selected from —F, —Cl, —Br, —I, CN, —R$^a$, —OR$^a$, —(CH$_2$)$_r$OR$^a$, —SR$^a$, —(CH$_2$)$_r$SR$^a$ or —NR$^a_2$, with each R$^a$ being selected independently from each other from H, a substituted or unsubstituted C$_1$-C$_8$ alkyl, in particular C$_1$-C$_4$ alkyl, a substituted or unsubstituted C$_2$-C$_8$ alkenyl, in particular C$_2$-C$_4$ alkenyl, or a substituted or unsubstituted C$_2$-C$_8$ alkynyl, in particular C$_2$-C$_4$ alkynyl, with r being 1, 2, 3 or 4, in particular r is 1, with R$^c$ being —CH$_2$OH, —CH$_3$, —CH$_2$CH$_3$, —CH$_2$CH$_2$CH$_3$, —CH(CH$_3$)$_2$, —CH$_2$CF$_3$, —CHFCF$_3$, —CF$_2$CF$_3$, —CHF$_2$, —CH$_2$F, —CF$_3$.

In some embodiments, R$^1$ comprises the general formula 2b' to 2i' or 2b to 2i, in particular the general formula 2b to 2i, with R$^c$, n of Z$^1_n$ and Z$^1_n$ having the same meaning as defined previously, and with T' of the compound according to formula 2a being selected from —NH, —S, —O or —NR$^c$, wherein in particular T' is O, R$^4$ and R$^5$ being selected independently from each other from —H, —F, —CH$_3$, in particular with R$^5$ and R$^6$ being H, with T' of the compound according to formula 2b or 2c being selected from —NH, —S, —O or —NR$^c$, wherein in particular T' is S or —NH, and T" being selected from —CH or =N, and with R$^6$ being selected from —CH$_3$ or H, in particular R$^6$ is H, with each T of the compound according to formula 2d being selected independently from each other from —NH, —S, —O or —NR$^c$, in particular at least one T is selected from NH or —NCH$_3$, more particularly the T in the position 4, with respect to the connection to the parent moiety, is —NH, and with R$^7$ being selected from =NH, =S or =O, in particular from O, and with T' of the compound according to formula 2e being selected from —CH$_2$, —NH, —S or —O, in particular T' being —NH or —O, with each T" of the compound according to formula 2f being selected independently from each other from —CH or =N, in particular each T" is =N, with T' of the compound according to formula 2g or 2h being selected from —NH, —S, —O or —NR$^c$, wherein in particular T' is —NR$^c$ or —NH, and T" being selected from —CH or =N, in particular T" is =N, with T' of the compound according to formula 2i or 2j being selected from —NH or —NR$^c$, wherein in particular T' is —NH, and T" is =N.

In some embodiments, R$^1$ comprises the general formula 2b to 2h, (2b)

(2c)

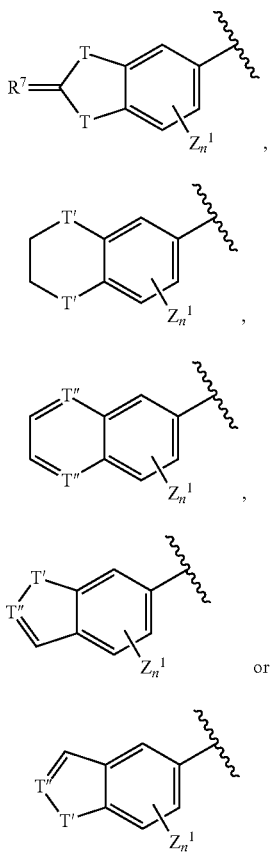

(2d)

(2e)

(2f)

(2g)

or (2h)

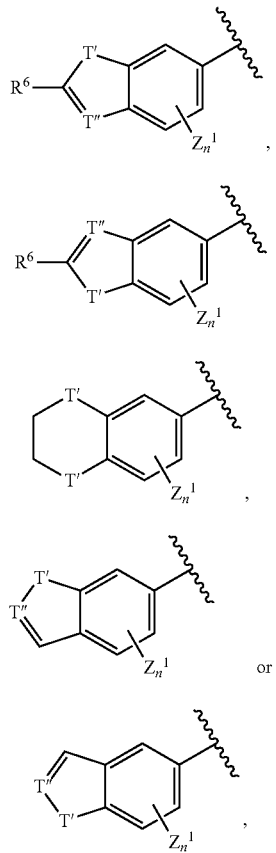

(2b)

(2c)

(2e)

(2g)

or (2h)

with T, T', T", n of $Z_n^1$, $Z_n^1$, $R^6$ and $R^7$ having the same meaning as defined previously.

In some embodiments, $R^1$ comprises the general formula 2b' to 2h' or 2b to 2h, in particular the general formula 2b to 2h, with $R^c$, n of $Z_n^1$ and $Z_n^1$ having the same meaning as defined previously, and
- with T' of the compound according to formula 2b or 2c being selected from —NH, —S, —O or —NR$^c$, wherein in particular T' is S or —NH, and T" being selected from —CH or =N, and with $R^6$ being selected from —CH$_3$ or H, in particular $R^6$ is H,
- with each T of the compound according to formula 2d being selected independently from each other from —NH, —S, —O or —NR$^c$, in particular at least one T is selected from NH or —NCH$_3$, more particularly the T in the position 4, with respect to the connection to the parent moiety, is —NH, and with $R^7$ being selected from =NH, =S or =O, in particular from O, and
- with T' of the compound according to formula 2e being selected from —CH$_2$, —NH, —S or —O, in particular T' being —O,
- with each T" of the compound according to formula 2f being selected independently from each other from —CH or =N, in particular each T" is =N,
- with T' of the compound according to formula 2g or 2h being selected from —NH, —S, —O or —NR$^c$, wherein in particular T' is —NR$^c$ or —NH, and T" being selected from —CH or =N, in particular T" is =N.

In some embodiments, $R^1$ comprises the general formula 2b, 2c, 2e, 2g or 2h with T, T', T", n of $Z_n^1$, $Z_n^1$, $R^6$ and $R^7$ having the same meaning as defined previously.

In some embodiments, $R^1$ comprises the general formula 2b', 2c', 2e', 2g' or 2h' or 2b, 2c, 2e, 2g or 2h, in particular the general formula 2b, 2c, 2e, 2g or 2h, with $R^c$, n of $Z_n^1$ and $Z_n^1$ having the same meaning as defined previously and
- with T' of the compound according to formula 2b or 2c being selected from —NH, —S, —O or —NR$^c$, wherein in particular T' is S or —NH, and T" being selected from —CH or =N, and with $R^6$ being selected from —CH$_3$ or H, in particular $R^6$ is H,
- with T' of the compound according to formula 2e being selected from —CH$_2$, —NH, —S or —O, in particular T' being —O,
- with T' of the compound according to formula 2g or 2h being selected from —NH, —S, —O or —NR$^c$, wherein in particular T' is —NR$^c$ or —NH, and T" being selected from —CH or =N, in particular T" is =N.

In some embodiments, $R^1$ comprises the general formula 2b, 2c, 2g or 2h,

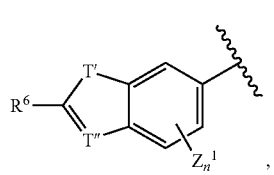

(2b)

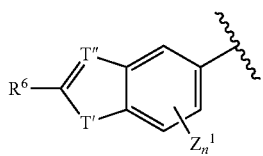
(2c)

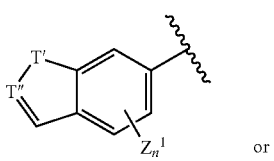
(2g)

or

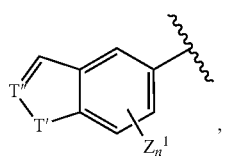
(2h)

with T, T', T", n of $Z_n^1$, $Z_n^1$, $R^6$ and $R^7$ having the same meaning as defined previously.

In some embodiments, $R^1$ comprises the general formula 2b', 2c', 2g' or 2h' or 2b, 2c, 2g or 2h, in particular the general formula 2b, 2c, 2g or 2h, with $R^c$, n of $Z_n^1$ and $Z_n^1$ having the same meaning as defined previously and
with T' of the compound according to formula 2b or 2c being selected from —NH, —S, —O or —NR$^c$, wherein in particular T' is S or —NH, and T" being selected from —CH or =N, and with $R^6$ being selected from —CH$_3$ or H, in particular $R^6$ is H,
with T' of the compound according to formula 2g or 2h being selected from —NH, —S, —O or —NR$^c$, wherein in particular T' is —NR$^c$ or —NH, and T" being selected from —CH or =N, in particular T" is =N.

In some embodiments, $R^1$ comprises the general formula 2b or 2c

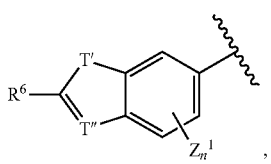
(2b)

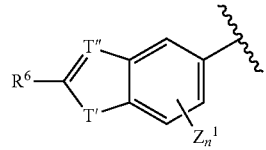
(2c)

with T', T", n of $Z_n^1$, $Z_n^1$ and $R^6$ having the same meaning as defined previously.

In some embodiments, $R^1$ comprises the general formula 2b' or 2c' or 2b or 2c, in particular the general formula 2b or 2c, with $R^c$, n of $Z_n^1$ and $Z_n^1$ having the same meaning as defined previously,
with T' of the compound according to formula 2b or 2c being selected from —NH, —S, —O or —NR$^c$, wherein in particular T' is S or —NH, and T" being selected from —CH or =N, and with $R^6$ being selected from —CH$_3$ or H, in particular $R^6$ is H.

In some embodiments, $R^1$ comprises the general formula 2c

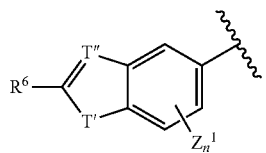
(2c)

with T', T", n of $Z_n^1$, $Z_n^1$ and $R^6$ having the same meaning as defined previously.

In some embodiments, $R^1$ comprises the general formula 2c' or 2c, in particular the general formula 2c, with $R^c$, n of $Z_n^1$ and $Z_n^1$ having the same meaning as defined previously,
with T' of the compound according to formula 2c being selected from —NH, —S, —O or —NR$^c$, wherein in particular T' is —NH, and T" being selected from —CH or =N, in particular from =N, and with $R^6$ being selected from —CH$_3$ or H, in particular $R^6$ is H.

In some embodiments, $R^c$ is selected from —CH$_2$OH, —CH$_3$, —CH$_2$CH$_3$, —CH$_2$CH$_2$CH$_3$ or —CH(CH$_3$)$_2$, in particular from —CH$_3$, —CH$_2$CH$_3$ or —CH(CH$_3$)$_2$, more particularly $R^c$ is CH$_3$.

In some embodiments, n of $Z_n^1$ is 0, 1 or 2, in particular n is 0 or 1.

In some embodiments, n of $Z_n^1$ is 1.
In some embodiments, n of $Z_n^1$ is 0.
In some embodiments, each $Z^1$ independently from any other $Z^1$ is selected from —F, —Cl, —Br, —I, CN, —R$^a$, —OR$^a$, CH$_2$OR$^a$, with each R$^a$ being selected independently from each other from H, a substituted or unsubstituted C$_1$-C$_{08}$ alkyl, in particular C$_1$-C$_4$ alkyl, a substituted or unsubstituted C$_2$-C$_8$ alkenyl, in particular C$_2$-C$_4$ alkenyl, or a substituted or unsubstituted C$_2$-C$_8$ alkynyl, in particular C$_2$-C$_4$ alkynyl.

In some embodiments, each $Z^1$ independently from any other $Z^1$ is selected from —F, —Cl, —Br, —I, CN, CH$_2$OR$^a$ or —OR$^a$, with each R$^a$ being selected independently from each other from H, a substituted or unsubstituted C$_1$-C$_{08}$ alkyl, in particular C$_1$-C$_4$ alkyl, a substituted or unsubstituted C$_2$-C$_8$ alkenyl, in particular C$_2$-C$_4$ alkenyl, or a substituted or unsubstituted C$_2$-C$_8$ alkynyl, in particular C$_2$-C$_4$ alkynyl.

In some embodiments, each $Z^1$ independently from any other $Z^1$ is selected from —F, —Cl, —Br, —I, CN, OH, CH$_2$OH, CH$_2$OR$^a$ or —OR$^a$ with R$^a$ being selected from a C$_1$-C$_4$ alkyl, C$_2$-C$_4$ alkenyl or C$_2$-C$_4$ alkenyl, in particular from a C$_1$-C$_4$ alkyl.

In some embodiments, each $Z^1$ independently from any other $Z^1$ is selected from CN, OH, —OCH$_3$, —OCH$_2$CH$_3$, —O(CH$_2$)$_2$CH$_3$, —O(CH$_2$)CCH, —CH$_2$OCH$_3$, —CH$_2$OCH$_2$CH$_3$, —CH$_2$O(CH$_2$)$_2$CH$_3$ or —CH$_2$O(CH$_2$)CCH, in particular from CN, OH, —OCH$_3$ or —CH$_2$OCH$_3$, more particularly from —OCH$_3$ or —CH$_2$OCH$_3$.

In some embodiments, $R^1$ is selected from

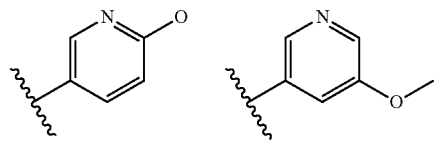

-continued
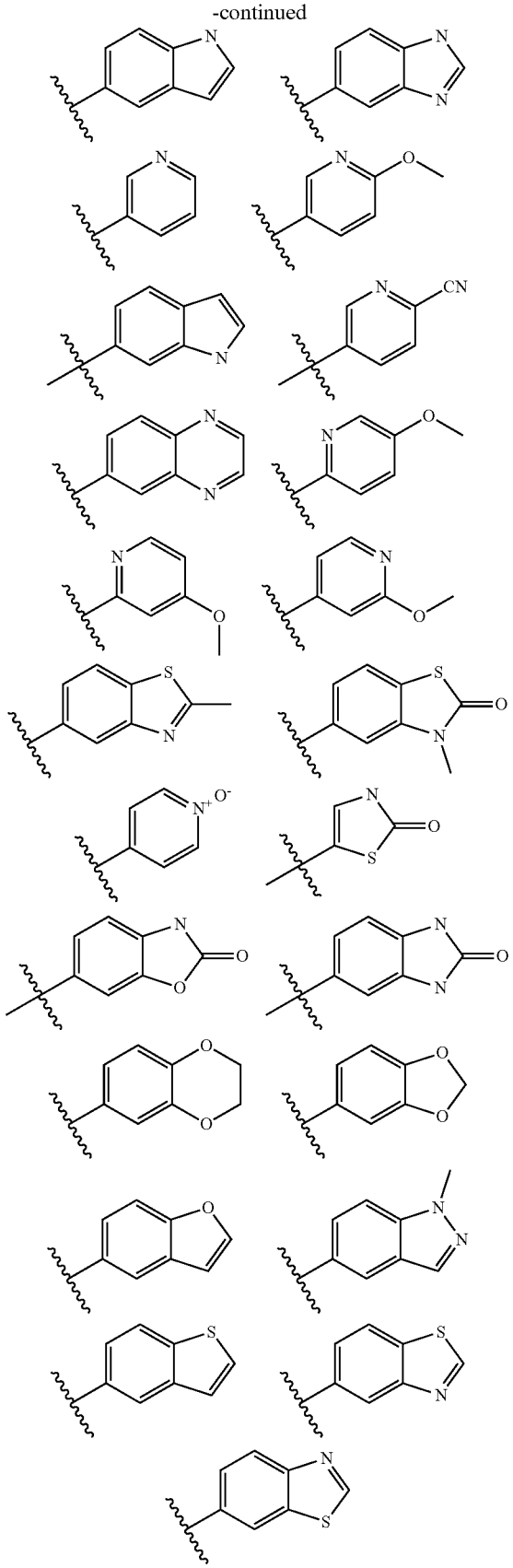
or derivatives thereof.
In some embodiments, $R^1$ is selected from
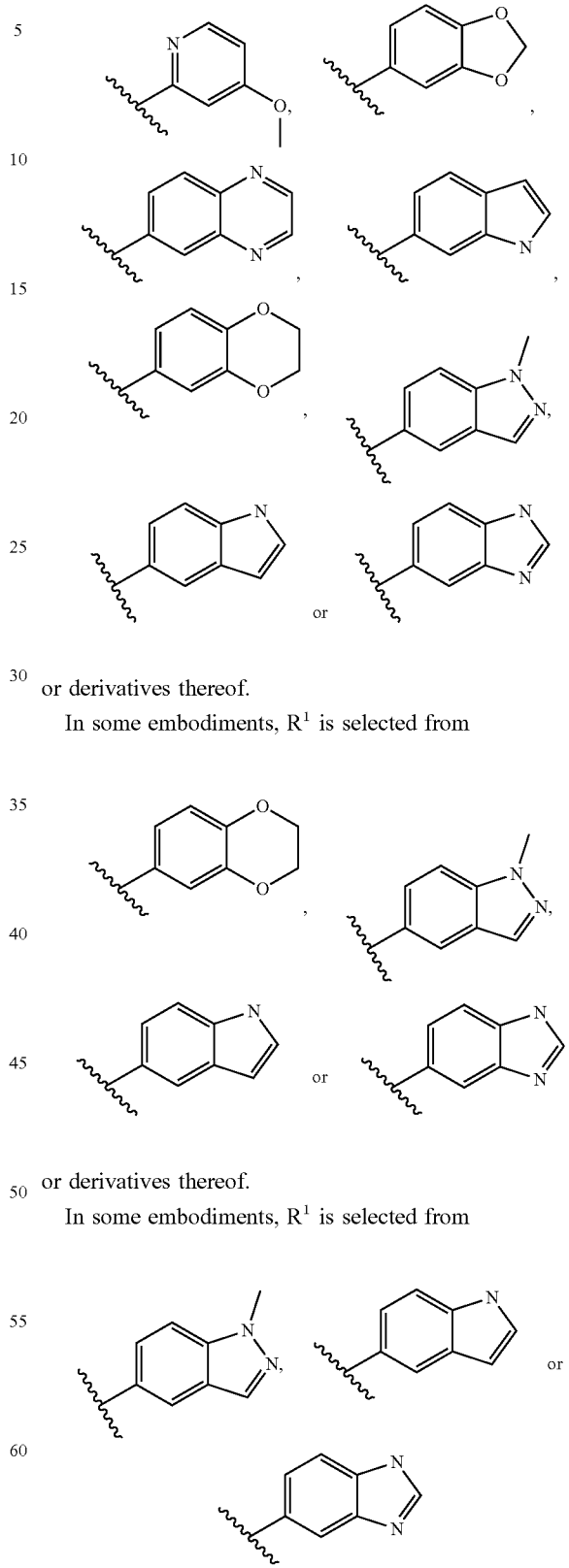
or derivatives thereof.
In some embodiments, $R^1$ is selected from
or derivatives thereof.
In some embodiments, $R^1$ is selected from
or derivatives thereof.

In some embodiments, $R^1$ is selected from

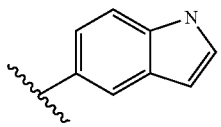 or 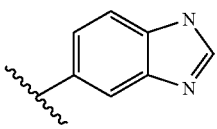

or derivatives thereof.

In some embodiments $R^1$ comprises the general formula 3a to 3k

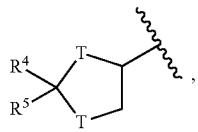 (3a)

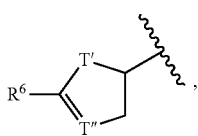 (3b)

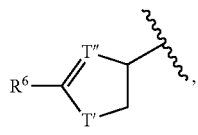 (3c)

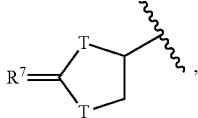 (3d)

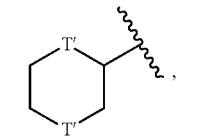 (3e)

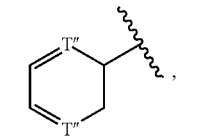 (3f)

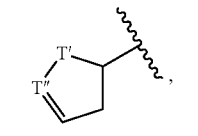 (3g)

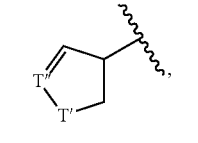 (3h)

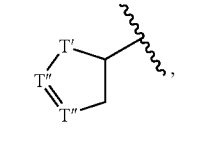 (3i)

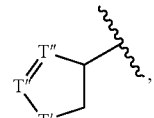 (3j)

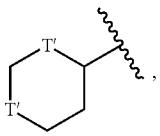 (3k)

with each T being selected independently from each other from —$CH_2$, —NH, —S, —O, —$CHCH_3$, —$C(CH_3)_2$ or —$NR^c$, in particular from NH, —S or —O, and with T' being selected from —$CH_2$, —NH, —S, —O, —$CHCH_3$, —$C(CH_3)_2$ or —$NR^c$, and with each T" being selected independently from each other from being selected from —CH or =N, with $R^4$ and $R^5$ being selected independently from each other from —H, —F, —$CH_3$, —$CH_2CH_3$, —$OCH_3$, —$CH_2CF_3$, —$CHFCF_3$, —$CF_2CF_3$, —$CHF_2$, —$CH_2F$ or —$CF_3$, in particular with $R^5$ and $R^6$ being selected independently from each other from H, —F or —$CH_3$, and with $R^6$ being selected from —OH, —$OCH_3$, —$OCH_2CH_3$, —$CH_3$ or H, with $R^7$ being selected from =NH, =S or =O, in particular from 0, and with $R^c$ being —$CH_2OH$, —$CH_3$, —$CH_2CH_3$, —$CH_2CH_2CH_3$, —$CH(CH_3)_2$, —$CH_2CF_3$, —$CHFCF_3$, —$CF_2CF_3$, —$CHF_2$, —$CH_2F$, —$CF_3$.

In some embodiments $R^1$ comprises the general formula 3a to 3k with T' of the compound according to formula 3a being selected from —NH, —S, —O or —$NR^c$, wherein in particular T' is O, $R^4$ and $R^5$ being selected independently from each other from —H, —F, —$CH_3$, in particular with $R^5$ and $R^6$ being H, with T' of the compound according to formula 3b or 3c being selected from —NH, —S, —O or —$NR^c$, wherein in particular T' is —NH, and T" being selected from —CH or =N, and with $R^6$ being selected from —$CH_3$ or H, in particular $R^6$ is H, with each T of the compound according to formula 3d being selected independently from each other from —NH, —S, —O or —$NR^c$, in particular at least one T is selected from NH or —$NCH_3$, more particularly the T in the position 4, with respect to the connection to the parent moiety, is —NH, and with $R^7$ being selected from =NH, =S or =O, in particular from 0, and with T' of the compound according to formula 3e being selected from —$CH_2$, —NH, —S or —O, in particular T' being —NH or —O, with each T" of the compound according to formula 3f being selected independently from each other from —CH or =N, in particular each T" is =N, with T' of the compound according to formula 3g or 3h being selected from —NH or —$NR^c$, wherein in particular T' is —$NCH_3$, and T" being selected from —CH or =N, in particular from =N, with T' of the compound according to formula 3i or 3j being selected from —NH or —$NR^c$, wherein in particular T' is —NH, and T" is =N.

In some embodiments $R^1$ is selected from a substituted or unsubstituted $C_5$ heterocycle or a substituted or unsubstituted $C_5$-$C_6$ heteroaryl, wherein in particular the substituted $C_5$ heterocycle or the substituted $C_5$-$C_6$ heteroaryl comprises at least one substituent $Z^1$ In some embodiments $R^1$ is selected from a substituted or unsubstituted pyran, furan, imidazole, thiophen, pyrrol, pyridine, pyrazine, thiazol, oxazol, cumarin, benzoimidazole, indol, Isoindol, benzodiazol, benzotriazol, benzoxazol, benzothiazol or pyrazin and derivatives thereof, wherein in particular the substituted compounds comprises at least one substituent Z.

In some embodiments, $R^c$ is selected from —$CH_2OH$, —$CH_3$, —$CH_2CH_3$, —$CH_2CH_2CH_3$ or —$CH(CH_3)_2$, in particular from —$CH_3$, —$CH_2CH_3$ or —$CH(CH_3)_2$, more particularly $R^c$ is $CH_3$.

In some embodiments, $R^2$ is selected from
a substituted or unsubstituted alkyl, in particular a substituted or unsubstituted $C_1$-$C_{12}$ alkyl,
a substituted or unsubstituted alkenyl, in particular a substituted or unsubstituted $C_2$-$C_{12}$ alkenyl,
a substituted or unsubstituted alkynyl, in particular a substituted or unsubstituted $C_2$-$C_{12}$ alkynyl,
a substituted or unsubstituted cycloalkyl, in particular a substituted or unsubstituted $C_3$-$C_{10}$ cycloalkyl,
a substituted or unsubstituted aryl, in particular a substituted or unsubstituted $C_6$-$C_{10}$ aryl.

In some embodiments, $R^2$ is selected from
a substituted or unsubstituted alkyl, in particular a substituted or unsubstituted $C_1$-$C_{12}$ alkyl,
a substituted or unsubstituted alkenyl, in particular a substituted or unsubstituted $C_2$-$C_{12}$ alkenyl,
a substituted or unsubstituted alkynyl, in particular a substituted or unsubstituted $C_2$-$C_{12}$ alkynyl,
a substituted or unsubstituted aryl, in particular a substituted or unsubstituted $C_6$-$C_{10}$ aryl, or
a substituted or unsubstituted heteroaryl, in particular a substituted or unsubstituted $C_5$-$C_{10}$ heteroaryl.

In some embodiments, $R^2$ is selected from
a substituted or unsubstituted $C_1$-$C_4$ alkyl,
a substituted or unsubstituted $C_2$-$C_4$ alkenyl,
a substituted or unsubstituted $C_2$-$C_4$ alkynyl,
a substituted or unsubstituted $C_6$ aryl, or
a substituted or unsubstituted $C_5$-$C_6$- heteroaryl.

In some embodiments, $R^2$ is selected from
a substituted alkyl, alkenyl or alkynyl, wherein the substituted alkyl, alkenyl or alkynyl comprises the formula -L-Ar,
with L being
an alkyl, in particular a $C_1$-$C_{12}$ alkyl, more particularly a $C_1$-$C_4$ alkyl,
an alkenyl, in particular a $C_2$-$C_{12}$ alkenyl, more particularly a $C_2$-$C_4$ alkenyl,
an alkynyl, in particular a $C_2$-$C_{12}$ alkynyl, more particularly a $C_2$-$C_4$ alkynyl, and
Ar being a substituted or unsubstituted $C_5$-$C_6$- aryl or a substituted or unsubstituted $C_5$-$C_6$- heteroaryl, or
a substituted or unsubstituted $C_6$- aryl or a substituted or unsubstituted $C_5$-$C_6$- heteroaryl, wherein in particular the substituted $C_6$- aryl or the substituted $C_5$-$C_6$- heteroaryl comprises at least one substituent $Z^2$.

In some embodiments, $R^2$ is selected from a substituted alkyl, wherein the substituted alkyl comprises the formula -L-Ar,
with L being
an alkyl, in particular a $C_1$-$C_{12}$ alkyl, more particularly a $C_1$-$C_4$ alkyl, and
Ar being a substituted or unsubstituted $C_5$-$C_6$- aryl or a substituted or unsubstituted $C_5$-$C_6$- heteroaryl, or
a substituted or unsubstituted $C_6$- aryl or a substituted or unsubstituted $C_5$-$C_6$- heteroaryl wherein in particular the substituted $C_6$- aryl or the substituted $C_5$-$C_6$- heteroaryl comprises at least one substituent $Z^2$.

In some embodiments, $R^2$ is selected from a substituted alkyl, wherein the substituted alkyl comprises the formula -L-Ar, with L being an alkyl, in particular a $C_1$-$C_{12}$ alkyl, more particularly a $C_1$-$C_4$ alkyl, and Ar being a substituted or unsubstituted $C_5$-$C_6$- aryl or a substituted or unsubstituted $C_5$-$C_6$- heteroaryl, wherein in particular the substituted $C_6$-aryl or the substituted $C_5$-$C_6$- heteroaryl comprises at least one substituent $Z^2$.

In some embodiments, $R^2$ is selected from a substituted or unsubstituted $C_6$- aryl or a substituted or unsubstituted $C_5$-$C_6$- heteroaryl, wherein in particular the substituted $C_6$-aryl or the substituted $C_5$-$C_6$- heteroaryl comprises at least one substituent $Z^2$.

In some embodiments, $R^2$ is selected from
a substituted alkyl, alkenyl or alkynyl, wherein the substituted alkyl, alkenyl or alkynyl comprises the formula 4a

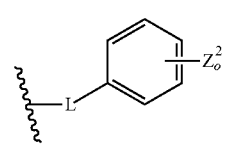

(formula 4a)

or
a substituted or unsubstituted $C_6$- aryl, wherein the substituted $C_6$ aryl comprises the formula 4b

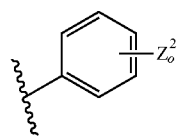

(formula 4b)

with L being
an alkyl, in particular a $C_1$-$C_{12}$ alkyl, more particularly a $C_1$-$C_4$ alkyl,
an alkenyl, in particular a $C_2$-$C_{12}$ alkenyl, more particularly a $C_2$-$C_4$ alkenyl,
an alkynyl, in particular a $C_2$-$C_{12}$ alkynyl, more particularly a $C_2$-$C_4$ alkynyl, and
o of $Z^2_o$ is 0, 1, 2, 3, 4 or 5, in particular 0, 1, 2 or 3, more particularly 0 or 1, and
each $Z^2$ independently from any other $Z^2$ is selected from —F, —Cl, —Br, —I, CN, —$R^b$, —$OR^b$, —$(CH_2)_rOR^b$, —$SR^b$, —$(CH_2)_rSR^b$ or —$NR^b_2$, with each $R^b$ being selected independently from each other from H, a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl, or a substituted or unsubstituted $C_2$-$C_{12}$ alkynyl, in particular $C_2$-$C_4$ alkynyl, with r being 1, 2, 3 or 4, in particular r is 1.

In some embodiments, $R^2$ is selected from
a substituted alkyl wherein the substituted alkyl comprises the formula 4a (formula 4a)

or
a substituted or unsubstituted $C_6$- aryl, wherein the substituted $C_6$ aryl comprises the formula 4b (formula 4b)

with L being an alkyl, in particular a $C_1$-$C_{12}$ alkyl, more particularly a $C_1$-$C_4$ alkyl, and
o of $Z^2_o$ is 0, 1, 2, 3, 4 or 5, in particular 0, 1, 2 or 3, more particularly 0 or 1, and
each $Z^2$ independently from any other $Z^2$ is selected from —F, —Cl, —Br, —I, CN, —$R^b$, —$OR^b$, —$(CH_2)_rOR^b$, —$SR^b$, —$(CH_2)_rSR^b$ or —$NR^b_2$, with each $R^b$ being selected independently from each other from H, a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl, or a substituted or unsubstituted $C_2$-$C_{12}$ alkynyl, in particular $C_2$-$C_4$ alkynyl, with r being 1, 2, 3 or 4, in particular r is 1.

In some embodiments, $R^2$ is selected from a substituted alkyl, wherein the substituted alkyl comprises the formula 4a, with L being an alkyl, in particular a $C_1$-$C_{12}$ alkyl, more particularly a $C_1$-$C_4$ alkyl, and o of $Z^2_o$ is 0, 1, 2, 3, 4 or 5, in particular 0, 1, 2 or 3, more particularly 0 or 1, and each $Z^2$ independently from any other $Z^2$ is selected from —F, —Cl, —Br, —I, CN, —$R^b$, —$OR^b$, —$(CH_2)_rOR^b$ or —$NR^b_2$, with each $R^b$ being selected independently from each other from H, a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl, or a substituted or unsubstituted $C_2$-$C_{12}$ alkynyl, in particular $C_2$-$C_4$ alkynyl, with r being 1, 2, 3 or 4, in particular r is 1.

In some embodiments, $R^2$ is selected from a substituted alkyl, wherein the substituted alkyl comprises the formula 4a, with L being an alkyl, in particular a $C_1$-$C_{12}$ alkyl, more particularly a $C_1$-$C_4$ alkyl, and o of $Z^2_o$ is 0, 1, 2, 3, 4 or 5, in particular 0, 1, 2 or 3, more particularly 0 or 1, and each $Z^2$ independently from any other $Z^2$ is selected from —F, —Cl, —Br, —I, CN, —$R^b$, —$OR^b$, —$(CH_2)_rOR^b$ or —$NR^b_2$, with each $R^b$ being selected independently from each other from H, a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl, or a substituted or unsubstituted $C_2$-$C_{12}$ alkynyl, in particular $C_2$-$C_4$ alkynyl, with r being 1, 2, 3 or 4, in particular r is 1.

In some embodiments, $R^2$ is selected from a substituted alkyl, wherein the substituted alkyl comprises the formula 4a, with L being an alkyl, in particular a $C_1$-$C_{12}$ alkyl, more particularly a $C_1$-$C_4$ alkyl,
an alkenyl, in particular a $C_2$-$C_{12}$ alkenyl, more particularly a $C_2$-$C_4$ alkenyl,
an alkynyl, in particular a $C_2$-$C_{12}$ alkynyl, more particularly a $C_2$-$C_4$ alkynyl,
and o of $Z^2_o$ is 1 and $Z^2$ is selected from —F, —Cl, —Br, —I, CN, —$R^b$, —$OR^b$, —$(CH_2)_rOR^b$ or —$NR^b_2$, with each $R^b$ being selected independently from each other from H, a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl, or a substituted or unsubstituted $C_2$-$C_{12}$ alkynyl, in particular $C_2$-$C_4$ alkynyl, with r being 1, 2, 3 or 4, in particular r is 1.

In some embodiments, $R^2$ is selected from a substituted alkyl, wherein the substituted alkyl comprises the formula 4a, with L being an alkyl, in particular a $C_1$-$C_{12}$ alkyl, more particularly a $C_1$-$C_4$ alkyl, and o of $Z^2_o$ is 0.

In some embodiments, $R^2$ is selected from a substituted alkyl, wherein the substituted alkyl comprises the formula 4b, with o of $Z^2_o$ being 0, 1, 2, 3, 4 or 5, in particular 0, 1, 2 or 3, more particularly 0 or 1, and each $Z^2$ independently from any other $Z^2$ is selected from —F, —Cl, —Br, —I, CN, —$R^b$, —$OR^b$, —$(CH_2)_rOR^b$ or —$NR^b_2$, with each $R^b$ being selected independently from each other from H, a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl, or a substituted or unsubstituted $C_2$-$C_{12}$ alkynyl, in particular $C_2$-$C_4$ alkynyl, with r being 1, 2, 3 or 4, in particular r is 1.

In some embodiments, $R^2$ is selected from a substituted alkyl, wherein the substituted alkyl comprises the formula 4b, with o of $Z^2_o$ being 0, 1, 2, 3, 4 or 5, in particular 0, 1, 2 or 3, more particularly 0 or 1, and each $Z^2$ independently from any other $Z^2$ is selected from —F, —Cl, —Br, —I, ON, —$R^b$, —$OR^b$, —$(CH_2)_rOR^b$ or —$NR^b_2$, with each $R^b$ being selected independently from each other from H, a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl, or a substituted or unsubstituted $C_2$-$C_{12}$ alkynyl, in particular $C_2$-$C_4$ alkynyl, with r being 1, 2, 3 or 4, in particular r is 1.

In some embodiments, $R^2$ is selected from a substituted alkyl, wherein the substituted alkyl comprises the formula 4b, with o of $Z^2_o$ being 1 and $Z^2$ is selected from —F, —Cl, —Br, —I, CN, —$R^b$, —$OR^b$, —$(CH_2)_rOR^b$ or —$NR^b_2$, with each $R^b$ being selected independently from each other from H, a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl, or a substituted or unsubstituted $C_2$-$C_{12}$ alkynyl, in particular $C_2$-$C_4$ alkynyl, with r being 1, 2, 3 or 4, in particular r is 1.

In some embodiments, $R^2$ is selected from a substituted alkyl, wherein the substituted alkyl comprises the formula 4b, with o of $Z^2_o$ being 0.

In some embodiments, o of $Z^2_o$ is 0, 1, 2, 3, 4 or 5, in particular 0, 1, 2 or 3, more particularly 0 or 1, and each $Z^2$ is selected independently from any other $Z^2$ from —F, —Cl, —Br, —I, CN, —$R^b$, —$OR^b$, $CH_2OR^b$ or —$NR^b_2$, in particular from —F, —Cl, —$R^b$, —$OR^b$, $CH_2OR^b$ or —$NR^b_2$, more particularly from —F, —Cl, —$R^b$, with each $R^b$ being selected independently from each other from H, a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl or a substituted or unsubstituted $C_2$-$C_{12}$ alkynyl, in particular $C_2$-$C_4$ alkynyl.

In some embodiments, o of $Z^2_o$ is 0, 1, 2, 3, 4 or 5, in particular 0, 1, 2 or 3, more particularly 0 or 1, and each $Z^2$ is selected independently from any other $Z^2$ from —F, —Cl, —Br, —I or —$R^b$, in particular from $R^b$, with $R^b$ being selected from a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl or a substituted or unsubstituted $C_2$-$C_{12}$ alkynyl, in particular $C_2$-$C_4$ alkynyl.

In some embodiments, o of $Z^2_o$ is 0, 1, 2, 3, 4 or 5, in particular 0, 1, 2 or 3, more particularly 0 or 1, and each $Z^2$ is selected independently from any other $Z^2$ from —F, —Cl, —Br, —I or —$R^b$, in particular from $R^b$, with $R^b$ being selected from a substituted or unsubstituted $C_1$-$C_{12}$ alkyl, in particular $C_1$-$C_4$ alkyl.

In some embodiments, o of $Z^2_o$ is 0, 1, 2, 3, 4 or 5, in particular 0, 1, 2 or 3, more particularly 0 or 1, and each $Z^2$ is selected independently from any other $Z^2$ is selected from —$R^b$, with $R^b$ being selected from a substituted or unsubstituted $C_1$-$C_{12}$ alkyl, in particular $C_1$-$C_4$ alkyl.

In some embodiments, o of $Z^2_o$ is 0 or 1.

In some embodiments, o of $Z^2_o$ is 1.

In some embodiments, o of $Z^2_o$ is 0.

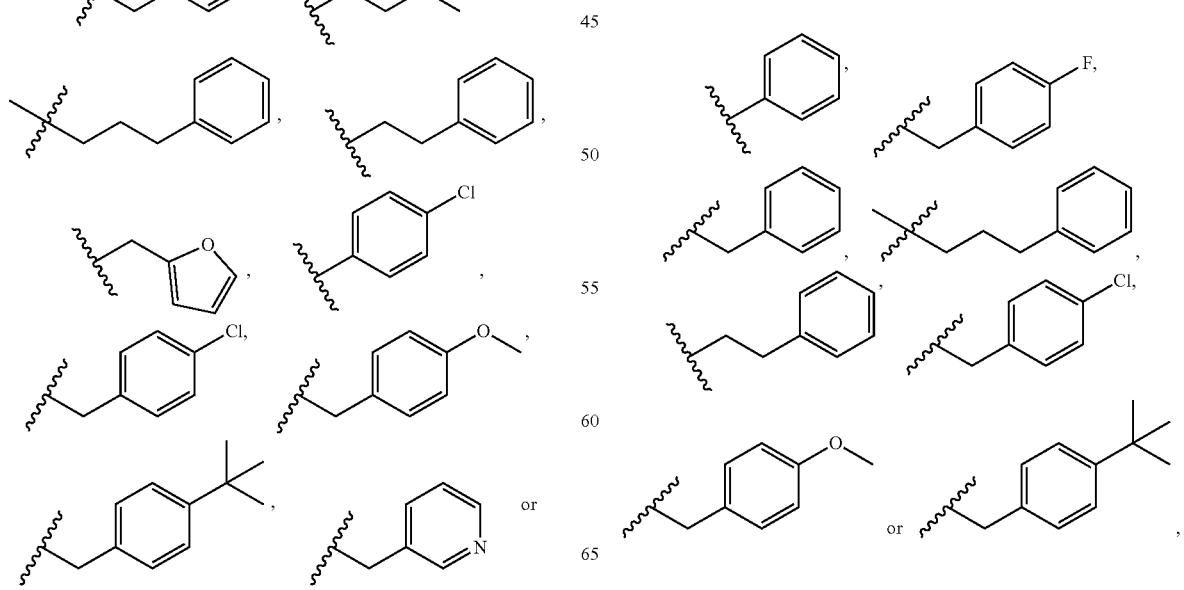

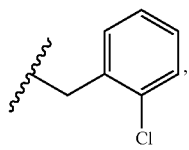

In some embodiments, $R^2$ is selected from

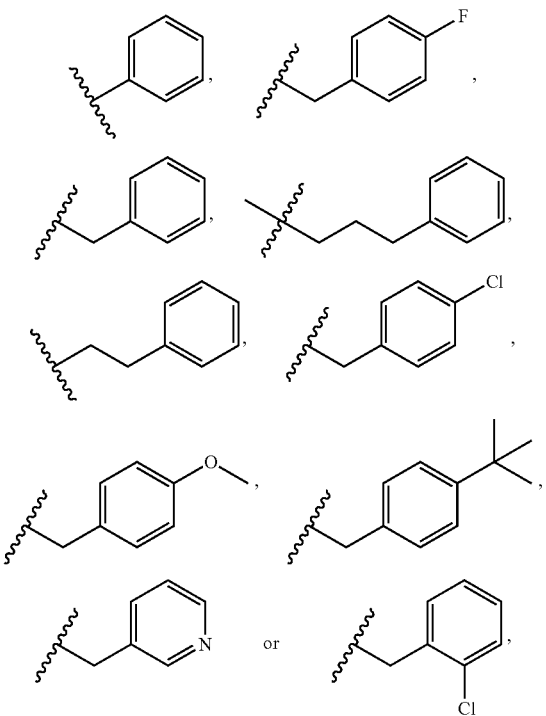

or derivatives thereof.

In some embodiments, $R^2$ is selected from or derivatives thereof.

In some embodiments, $R^2$ is selected from

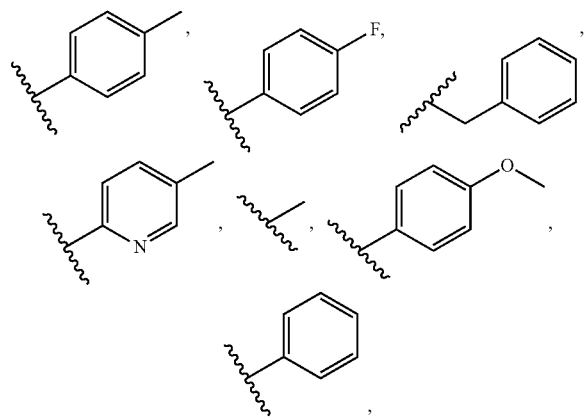

or derivatives thereof.

In some embodiments, $R^2$ is selected from

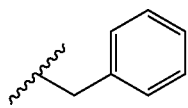 [SMILES: *Cc1ccccc1]

or derivatives thereof.

In some embodiments, $R^2$ is selected from

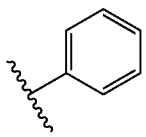 [SMILES: *c1ccccc1]

or derivatives thereof.

In some embodiments, $R^3$ is selected from
- a substituted or unsubstituted alkyl, in particular a substituted or unsubstituted $C_1$-$C_{12}$ alkyl,
- a substituted or unsubstituted alkenyl, in particular a substituted or unsubstituted $C_2$-$C_{12}$ alkenyl,
- a substituted or unsubstituted alkynyl, in particular a substituted or unsubstituted $C_2$-$C_{12}$ alkynyl,
- a substituted or unsubstituted cycloalkyl, in particular a substituted or unsubstituted $C_3$-$C_{10}$ cycloalkyl,
- a substituted or unsubstituted aryl, in particular a substituted or unsubstituted $C_6$-$C_{10}$ aryl.

In some embodiments, $R^3$ is selected from
- a substituted or unsubstituted alkyl, in particular a substituted or unsubstituted $C_1$-$C_{12}$ alkyl,
- a substituted or unsubstituted alkenyl, in particular a substituted or unsubstituted $C_2$-$C_{12}$ alkenyl,
- a substituted or unsubstituted alkynyl, in particular a substituted or unsubstituted $C_2$-$C_{12}$ alkynyl,
- a substituted or unsubstituted aryl, in particular a substituted or unsubstituted $C_6$-$C_{10}$ aryl, or
- a substituted or unsubstituted heteroaryl, in particular a substituted or unsubstituted $C_5$-$C_{10}$ heteroaryl.

In some embodiments, $R^3$ is selected from
- a substituted or unsubstituted $C_1$-$C_4$ alkyl,
- a substituted or unsubstituted $C_2$-$C_4$ alkenyl,
- a substituted or unsubstituted $C_2$-$C_4$ alkynyl,
- a substituted or unsubstituted $C_6$ aryl, or
- a substituted or unsubstituted $C_5$-$C_6$- heteroaryl.

In some embodiments, $R^3$ is selected from
- a substituted alkyl, alkenyl or alkynyl, wherein the substituted alkyl, alkenyl or alkynyl comprises the formula -D-Ar,
  - with D being
    - an alkyl, in particular a $C_1$-$C_{12}$ alkyl, more particularly a $C_1$-$C_4$ alkyl,
    - an alkenyl, in particular a $C_2$-$C_{12}$ alkenyl, more particularly a $C_2$-$C_4$ alkenyl,
    - an alkynyl, in particular a $C_2$-$C_{12}$ alkynyl, more particularly a $C_2$-$C_4$ alkynyl, and
  - Ar being a substituted or unsubstituted $C_5$-$C_6$- aryl or a substituted or unsubstituted $C_5$-$C_6$- heteroaryl, or
- a substituted or unsubstituted $C_6$- aryl or a substituted or unsubstituted $C_5$-$C_6$- heteroaryl, wherein in particular the substituted $C_6$- aryl or the substituted $C_5$-$C_6$- heteroaryl comprises at least one substituent $Z^3$.

In some embodiments, $R^3$ is selected from
- a substituted alkyl, wherein the substituted alkyl comprises the formula -D-Ar,
  - with D being
    - an alkyl, in particular a $C_1$-$C_{12}$ alkyl, more particularly a $C_1$-$C_4$ alkyl, and
  - Ar being a substituted or unsubstituted $C_5$-$C_6$- aryl or a substituted or unsubstituted $C_5$-$C_6$- heteroaryl, or
- a substituted or unsubstituted $C_6$- aryl or a substituted or unsubstituted $C_5$-$C_6$- heteroaryl wherein in particular the substituted $C_6$- aryl or the substituted $C_5$-$C_6$- heteroaryl comprises at least one substituent $Z^3$.

In some embodiments, $R^3$ is selected from a substituted alkyl, wherein the substituted alkyl comprises the formula -D-Ar, with L being an alkyl, in particular a $C_1$-$C_{12}$ alkyl, more particularly a $C_1$-$C_4$ alkyl, and Ar being a substituted or unsubstituted $C_5$-$C_6$- aryl or a substituted or unsubstituted $C_5$-$C_6$- heteroaryl, wherein in particular the substituted $C_6$- aryl or the substituted $C_5$-$C_6$- heteroaryl comprises at least one substituent $Z^3$.

In some embodiments, $R^3$ is selected from a substituted or unsubstituted $C_6$- aryl or a substituted or unsubstituted $C_5$-$C_6$- heteroaryl, wherein in particular the substituted $C_6$- aryl or the substituted $C_5$-$C_6$- heteroaryl comprises at least one substituent $Z^3$.

In some embodiments, $R^3$ is selected from
- a substituted alkyl, alkenyl or alkynyl, wherein the substituted alkyl, alkenyl or alkynyl comprises the formula 5a

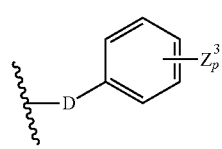

(formula 5a)

or a substituted or unsubstituted $C_6$- aryl, wherein the substituted $C_6$ aryl comprises the

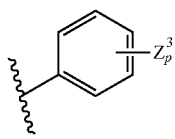
(formula 5b)

with D being
an alkyl, in particular a $C_1$-$C_{12}$ alkyl, more particularly a $C_1$-$C_4$ alkyl,
an alkenyl, in particular a $C_2$-$C_{12}$ alkenyl, more particularly a $C_2$-$C_4$ alkenyl,
an alkynyl, in particular a $C_2$-$C_{12}$ alkynyl, more particularly a $C_2$-$C_4$ alkynyl, and
p of $Z^3p$ is 0, 1, 2, 3, 4 or 5, in particular 0, 1, 2 or 3, more particularly 0 or 1, and
each $Z^3$ independently from any other $Z^3$ is selected from —F, —Cl, —Br, —I, CN, —$R^d$, —$OR^d$, —$(CH_2)_rOR^d$, —$SR^d$, —$(CH_2)_rSR^d$ or —$NR^d_2$, with each $R^d$ being selected independently from each other from H, a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl, or a substituted or unsubstituted $C_2$-$C_{12}$ alkynyl, in particular $C_2$-$C_4$ alkynyl, with r being 1, 2, 3 or 4, in particular r is 1.

In some embodiments, $R^3$ is selected from
a substituted alkyl wherein the substituted alkyl comprises the formula 5a

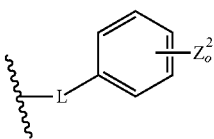
(formula 5a)

or
a substituted or unsubstituted $C_6$- aryl, wherein the substituted $C_6$ aryl comprises the formula 5b

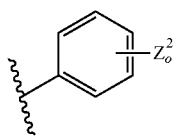
(formula 5b)

with D being an alkyl, in particular a $C_1$-$C_{12}$ alkyl, more particularly a $C_1$-$C_4$ alkyl, and
p of $Z^3_p$ is 0, 1, 2, 3, 4 or 5, in particular 0, 1, 2 or 3, more particularly 0 or 1, and
each $Z^3$ independently from any other $Z^3$ is selected from —F, —Cl, —Br, —I, CN, —$R^d$, —$OR^d$, —$(CH_2)_rOR^d$, —$SR^d$, —$(CH_2)_rSR^d$ or —$NR^d_2$, with each $R^d$ being selected independently from each other from H, a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl, or a substituted or unsubstituted $C_2$-$C_{12}$ alkynyl, in particular $C_2$-$C_4$ alkynyl, with r being 1, 2, 3 or 4, in particular r is 1.

In some embodiments, $R^3$ is selected from a substituted alkyl, wherein the substituted alkyl comprises the formula 5a, with D being an alkyl, in particular a $C_1$-$C_{12}$ alkyl, more particularly a $C_1$-$C_4$ alkyl, and p of $Z^3_p$ is 0, 1, 2, 3, 4 or 5, in particular 0, 1, 2 or 3, more particularly 0 or 1, and each $Z^3$ independently from any other $Z^3$ is selected from —F, —Cl, —Br, —I, CN, —$R^d$, —$OR^d$, —$(CH_2)_rOR^d$, —$SR^d$, —$(CH_2)_rSR^d$ or —$NR^d_2$, with each $R^d$ being selected independently from each other from H, a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl, or a substituted or unsubstituted $C_2$-$C_{12}$ alkynyl, in particular $C_2$-$C_4$ alkynyl, with r being 1, 2, 3 or 4, in particular r is 1.

In some embodiments, $R^3$ is selected from a substituted alkyl, wherein the substituted alkyl comprises the formula 5a, with D being an alkyl, in particular a $C_1$-$C_{12}$ alkyl, more particularly a $C_1$-$C_4$ alkyl, and p of $Z^3_p$ is 0, 1, 2, 3, 4 or 5, in particular 0, 1, 2 or 3, more particularly 0 or 1, and each $Z^3$ independently from any other $Z^3$ is selected from —F, —Cl, —Br, —I, CN, —$R^d$, —$OR^d$, —$(CH_2)_rOR^d$, —$SR^d$, —$(CH_2)_rSR^d$ or —$NR^d_2$, with each $R^d$ being selected independently from each other from H, a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl, or a substituted or unsubstituted $C_2$-$C_{12}$ alkynyl, in particular $C_2$-$C_4$ alkynyl, with r being 1, 2, 3 or 4, in particular r is 1.

In some embodiments, $R^3$ is selected from a substituted alkyl, wherein the substituted alkyl comprises the formula 5a, with D being
an alkyl, in particular a $C_1$-$C_{12}$ alkyl, more particularly a $C_1$-$C_4$ alkyl,
an alkenyl, in particular a $C_2$-$C_{12}$ alkenyl, more particularly a $C_2$-$C_4$ alkenyl,
an alkynyl, in particular a $C_2$-$C_{12}$ alkynyl, more particularly a $C_2$-$C_4$ alkynyl,
and p of $Z^3_p$ is 1 and $Z^3$ is selected from —F, —Cl, —Br, —I, CN, —$R^d$, —$OR^d$, —$(CH_2)_rOR^d$, —$SR^d$, —$(CH_2)_rSR^d$ or —$NR^d_2$, with each $R^d$ being selected independently from each other from H, a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl, or a substituted or unsubstituted $C_2$-$C_{12}$ alkynyl, in particular $C_2$-$C_4$ alkynyl, with r being 1, 2, 3 or 4, in particular r is 1.

In some embodiments, $R^3$ is selected from a substituted alkyl, wherein the substituted alkyl comprises the formula 5a, with D being an alkyl, in particular a $C_1$-$C_{12}$ alkyl, more particularly a $C_1$-$C_4$ alkyl, and p of $Z^3_p$ is 0.

In some embodiments, $R^3$ is selected from a substituted alkyl, wherein the substituted alkyl comprises the formula 5b, with p of $Z^3_p$ being 0, 1, 2, 3, 4 or 5, in particular 0, 1, 2 or 3, more particularly 0 or 1, and each $Z^3$ independently from any other $Z^3$ is selected from —F, —Cl, —Br, —I, CN, —$R^d$, —$OR^d$, —$(CH_2)_rOR^d$, —$SR^d$, —$(CH_2)_rSR^d$ or —$NR^d_2$, with each $R^d$ being selected independently from each other from H, a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl, or a substituted or unsubstituted $C_2$-$C_{12}$ alkynyl, in particular $C_2$-$C_4$ alkynyl, with r being 1, 2, 3 or 4, in particular r is 1.

In some embodiments, $R^3$ is selected from a substituted alkyl, wherein the substituted alkyl comprises the formula 5b, with p of $Z^3_p$ being 0, 1, 2, 3, 4 or 5, in particular 0, 1, 2 or 3, more particularly 0 or 1, and each $Z^3$ independently from any other $Z^3$ is selected from —F, —Cl, —Br, —I, CN, —$R^d$, —$OR^d$, —$(CH_2)_rOR^d$, —$SR^d$, —$(CH_2)_rSR^d$ or —NR$^d_2$, with each R$^d$ being selected independently from each other from H, a substituted or unsubstituted C$_1$-C$_{12}$ alkyl, in particular C$_1$-C$_4$ alkyl, a substituted or unsubstituted C$_2$-C$_{12}$ alkenyl, in particular C$_2$-C$_4$ alkenyl, or a substituted or unsubstituted C$_2$-C$_{12}$ alkynyl, in particular C$_2$-C$_4$ alkynyl, with r being 1, 2, 3 or 4, in particular r is 1.

In some embodiments, R$^3$ is selected from a substituted alkyl, wherein the substituted alkyl comprises the formula 5b, with p of Z$^3_p$ being 1 and Z$^3$ is selected from —F, —Cl, —Br, —I, ON, —R$^d$, —OR$^d$, —(CH$_2$)$_r$OR$^d$, —SR$^d$, —(CH$_2$)$_r$SR$^d$ or —NR$^d_2$, with each R$^d$ being selected independently from each other from H, a substituted or unsubstituted C$_1$-C$_{12}$ alkyl, in particular C$_1$-C$_4$ alkyl, a substituted or unsubstituted C$_2$-C$_{12}$ alkenyl, in particular C$_2$-C$_4$ alkenyl, or a substituted or unsubstituted C$_2$-C$_{12}$ alkynyl, in particular C$_2$-C$_4$ alkynyl, with r being 1, 2, 3 or 4, in particular r is 1.

In some embodiments, R$^3$ is selected from a substituted alkyl, wherein the substituted alkyl comprises the formula 5b, p of Z$^3_p$ being 0.

In some embodiments, p of Z$^3_p$ is 0, 1, 2, 3, 4 or 5, in particular 0, 1, 2 or 3, more particularly 0 or 1, and each Z$^3$ is selected independently from any other Z$^3$ from —F, —Cl, —Br, —I, ON, —R$^d$, —OR$^d$, CH$_2$OR$^d$ or —NR$^d_2$, in particular from —F, —Cl, —R$^d$, —OR$^d$, CH$_2$OR$^d$ or —NR$^d_2$, more particularly from —F, —Cl, —R$^d$, with each R$^d$ being selected independently from each other from H, a substituted or unsubstituted C$_1$-C$_{12}$ alkyl, in particular C$_1$-C$_4$ alkyl, a substituted or unsubstituted C$_2$-C$_{12}$ alkenyl, in particular C$_2$-C$_4$ alkenyl or a substituted or unsubstituted C$_2$-C$_{12}$ alkynyl, in particular C$_2$-C$_4$ alkynyl.

In some embodiments, p of Z$^3_p$ is 0, 1, 2, 3, 4 or 5, in particular 0, 1, 2 or 3, more particularly 0 or 1, and each Z$^3$ is selected independently from any other Z$^3$ from —F, —Cl, —Br, —I or —R$^d$, in particular from R$^d$, with R$^d$ being selected from a substituted or unsubstituted C$_1$-C$_{12}$ alkyl, in particular C$_1$-C$_4$ alkyl, a substituted or unsubstituted C$_2$-C$_{12}$ alkenyl, in particular C$_2$-C$_4$ alkenyl or a substituted or unsubstituted C$_2$-C$_{12}$ alkynyl, in particular C$_2$-C$_4$ alkynyl.

In some embodiments, p of Z$^3_p$ is 0, 1, 2, 3, 4 or 5, in particular 0, 1, 2 or 3, more particularly 0 or 1, and each Z$^3$ is selected independently from any other Z$^3$ from —F, —Cl, —Br, —I or —R$^d$, in particular from R$^d$, with R$^d$ being selected from a substituted or unsubstituted C$_1$-C$_{12}$ alkyl, in particular C$_1$-C$_4$ alkyl.

In some embodiments, p of Z$^3_p$ is 0, 1, 2, 3, 4 or 5, in particular 0, 1, 2 or 3, more particularly 0 or 1, and each Z$^3$ is selected independently from any other Z$^3$ is selected from —R$^d$, with R$^d$ being selected from a substituted or unsubstituted C$_1$-C$_{12}$ alkyl, in particular C$_1$-C$_4$ alkyl.

In some embodiments, p of Z$^3_p$ is 0 or 1.
In some embodiments, p of Z$^3_p$ is 1.
In some embodiments, p of Z$^3_p$ is 0.
In some embodiments, R$^3$ is selected from

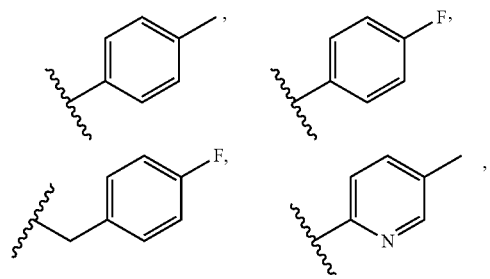

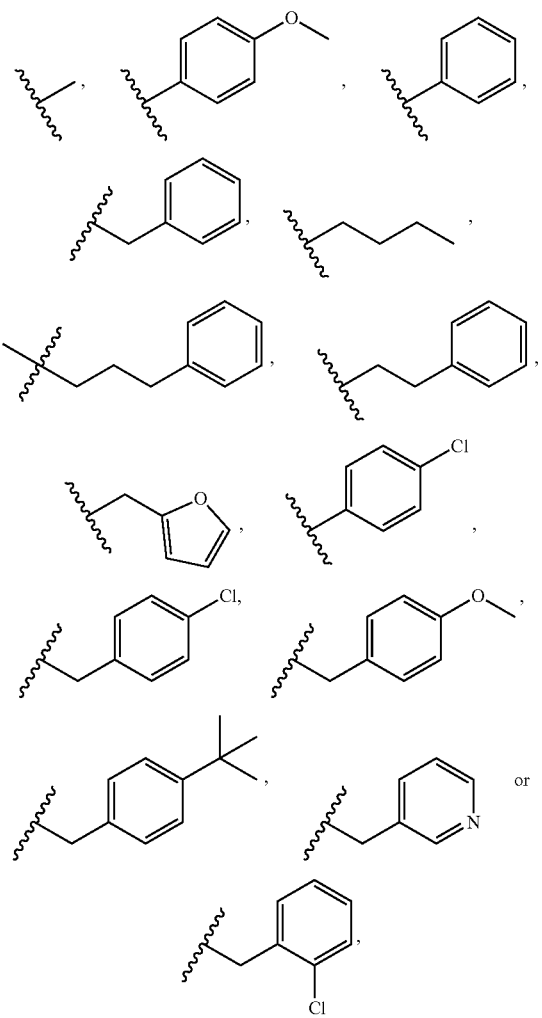

or derivatives thereof.

In some embodiments, R$^3$ is selected from

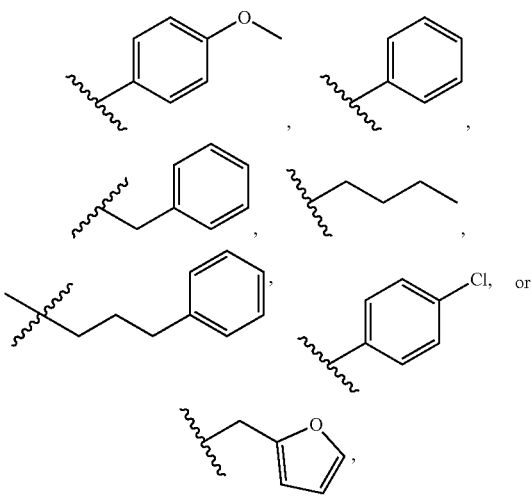

or derivatives thereof.

In some embodiments, $R^3$ is selected from

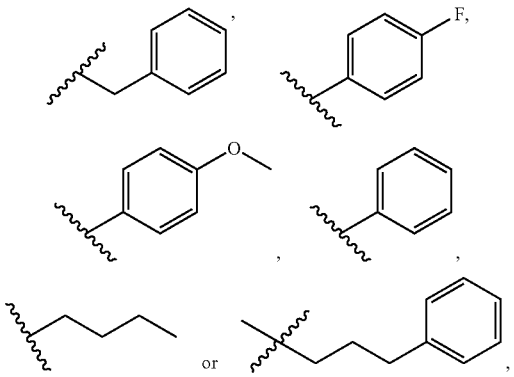, or derivatives thereof.

In some embodiments, $R^3$ is selected from

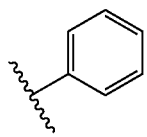 [SMILES: *c1ccccc1]

or derivatives thereof.

Any embodiment described for $R^2$ or $R^3$ according to the first aspect of the invention may be combined with any embodiment described for $R^1$ according to the first aspect of the invention.

In some embodiments of a first sub aspect of the first aspect, $R^1$ comprises the general formula 2a' or 2e',

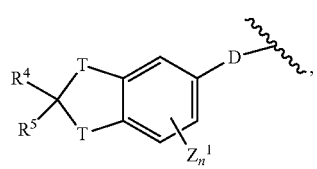 (2a')

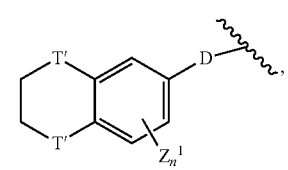 (2e')

with D being a $C_1$ to $C_4$ alkyl, or the general formula 2a or 2e,

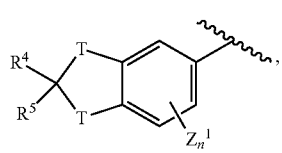 (2a)

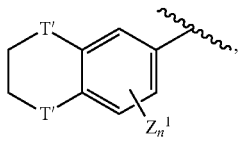 (2e)

with each T being selected independently from each other from —$CH_2$—, —NH—, —S—, —O—, —$CHCH_3$—, —$C(CH_3)_2$— or —$NR^c$—, in particular from NH, —S or —O, with $R^c$ being —$CH_2OH$, —$CH_3$, —$CH_2CH_3$, —$CH_2CH_2CH_3$, —$CH(CH_3)_2$, —$CH_2CF_3$, —$CHFCF_3$, —$CF_2CF_3$, —$CHF_2$, —$CH_2F$, —$CF_3$ and with T' being selected from —$CH_2$—, —NH—, —S—, —O—, —$CHCH_3$—, or —$C(CH_3)_2$— and with $R^4$ and $R^5$ being selected independently from each other from —H, —F, —$CH_3$, —$CH_2CH_3$, —$OCH_3$, —$CH_2CF_3$, —$CHFCF_3$, —$CF_2CF_3$, —$CHF_2$, —$CH_2F$ or —$CF_3$, in particular with $R^5$ and $R^6$ being selected independently from each other from H, —F or —$CH_3$, and with n of $Z^1_n$ being 0, 1, 2 or 3, in particular n of $Z^1_n$ being 0 or 1, and with each $Z^1$ independently from any other $Z^1$ being selected from —F, —Cl, —Br, —I, CN, —$R^a$, —$OR^a$, —$(CH_2)_rOR^a$, —$SR^a$, —$(CH_2)_rSR^a$ or —$NR^a_2$, with each $R^a$ being selected independently from each other from H, a substituted or unsubstituted $C_1$-$C_8$ alkyl, in particular $C_1$-$C_4$ alkyl, a substituted or unsubstituted $C_2$-$C_8$ alkenyl, in particular $C_2$-$C_4$ alkenyl, or a substituted or unsubstituted $C_2$-$C_8$ alkynyl, in particular $C_2$-$C_4$ alkynyl, with r being 1, 2, 3 or 4, in particular r is 1, $R^2$ is selected from
- a substituted or unsubstituted cycloalkyl, in particular a substituted or unsubstituted $C_3$-$C_{10}$ cycloalkyl,
- a substituted or unsubstituted aryl, in particular a substituted or unsubstituted $C_6$-$C_{10}$ aryl,
- a substituted or unsubstituted saturated heterocycle, in particular a substituted or unsubstituted $C_3$-$C_{10}$ heterocycle, or
- a substituted or unsubstituted heteroaryl, in particular a substituted or unsubstituted $C_5$-$C_{10}$ heteroaryl, and and $R^3$ is selected from
- a substituted or unsubstituted alkyl, in particular a substituted or unsubstituted $C_1$-$C_{12}$ alkyl,
- a substituted or unsubstituted alkoxy, in particular a substituted or unsubstituted $C_1$-$C_{12}$ alkoxy,
- a substituted or unsubstituted alkenyl, in particular a substituted or unsubstituted $C_1$-$C_{12}$ alkenyl,
- a substituted or unsubstituted alkynyl, in particular a substituted or unsubstituted $C_1$-$C_{12}$ alkynyl,
- a substituted or unsubstituted cycloalkyl, in particular a substituted or unsubstituted $C_3$-$C_{10}$ cycloalkyl,
- a substituted or unsubstituted aryl, in particular a substituted or unsubstituted $C_6$-$C_{10}$ aryl,
- a substituted or unsubstituted saturated heterocycle, in particular a substituted or unsubstituted $C_3$-$C_{10}$ heterocycle, or
- a substituted or unsubstituted heteroaryl, in particular a substituted or unsubstituted $C_5$-$C_{10}$ heteroaryl.

In some embodiments, particularly of the first sub aspect, $R^1$ comprises the general formula 2a or 2e,

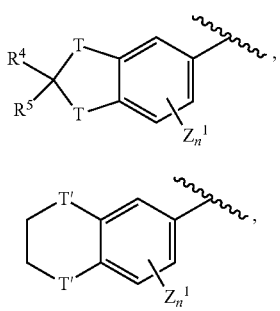

(2a)

(2e)

in particular 2e, with D, T, T', n of $Z_n^1$, $Z_n^1$, $R^4$ and $R^5$ having the same meaning as defined previously.

In some embodiments, particularly of the first sub aspect, T of the compound according to formula 2a is selected from —NH, —S, —O or —NR$^c$, wherein in particular T is O, $R^4$ and $R^5$ being selected independently from each other from —H, —F, —CH$_3$, in particular with $R^5$ and $R^6$ being H, and T' of the compound according to formula 2e is selected from —CH$_2$, —NH, —S or —O, in particular T' is —NH or —O, more particularly O.

In some embodiments, particularly of the first sub aspect, n of $Z^1_n$ is 0, 1 or 2, in particular n is 0 or 1. In some embodiments, n of $Z^1_n$ is 1. In some embodiments, n of $Z^1_n$ is 0.

In some embodiments, particularly of the first sub aspect, each $Z^1$ independently from any other $Z^1$ is selected from —F, —Cl, —Br, —I, CN, —R$^a$, —OR$^a$, CH$_2$OR$^a$, with each $R^a$ being selected independently from each other from H, a substituted or unsubstituted C$_1$-C$_{08}$ alkyl, in particular C$_1$-C$_4$ alkyl, a substituted or unsubstituted C$_2$-C$_8$ alkenyl, in particular C$_2$-C$_4$ alkenyl, or a substituted or unsubstituted C$_2$-C$_8$ alkynyl, in particular C$_2$-C$_4$ alkynyl In some embodiments, particularly of the first sub aspect, each $Z^1$ independently from any other $Z^1$ is selected from —F, —Cl, —Br, —I, CN, CH$_2$OR$^a$ or —OR$^a$, with each $R^a$ being selected independently from each other from H, a substituted or unsubstituted C$_1$-C$_{08}$ alkyl, in particular C$_1$-C$_4$ alkyl, a substituted or unsubstituted C$_2$-C$_8$ alkenyl, in particular C$_2$-C$_4$ alkenyl, or a substituted or unsubstituted C$_2$-C$_8$ alkynyl, in particular C$_2$-C$_4$ alkynyl.

In some embodiments, particularly of the first sub aspect, each $Z^1$ independently from any other $Z^1$ is selected from —F, —Cl, —Br, —I, CN, OH, CH$_2$OH, CH$_2$OR$^a$ or —OR$^a$ with $R^a$ being selected from a C$_1$-C$_4$ alkyl, C$_2$-C$_4$ alkenyl or C$_2$-C$_4$ alkenyl, in particular from a C$_1$-C$_4$ alkyl.

In some embodiments, particularly of the first sub aspect, each $Z^1$ independently from any other $Z^1$ is selected from CN, OH, —OCH$_3$, —OCH$_2$CH$_3$, —O(CH$_2$)$_2$CH$_3$, —O(CH$_2$)CCH, —CH$_2$OCH$_3$, —CH$_2$OCH$_2$CH$_3$, —CH$_2$O(CH$_2$)$_2$CH$_3$ or —CH$_2$O(CH$_2$)CCH, in particular from CN, OH, —OCH$_3$ or —CH$_2$OCH$_3$, more particularly from —OCH$_3$ or —CH$_2$OCH$_3$.

In some embodiments, particularly of the first sub aspect, $R^2$ is selected from a substituted or unsubstituted C$_3$-C$_6$ cycloalkyl, a substituted or unsubstituted C$_6$ aryl, or a substituted or unsubstituted C$_5$-C$_6$- heteroaryl.

In some embodiments, particularly of the first sub aspect, $R^2$ is selected from
a substituted alkyl, alkenyl or alkynyl, wherein the substituted alkyl, alkenyl or alkynyl comprises the formula -L-Ar, with L being
an alkyl, in particular a C$_1$-C$_{12}$ alkyl, more particularly a C$_1$-C$_4$ alkyl,
an alkenyl, in particular a C$_1$-C$_{12}$ alkenyl, more particularly a C$_1$-C$_4$ alkenyl,
an alkynyl, in particular a C$_1$-C$_{12}$ alkynyl, more particularly a C$_1$-C$_4$ alkynyl, and
Ar being a substituted or unsubstituted C$_5$-C$_6$- aryl or a substituted or unsubstituted C$_5$-C$_6$- heteroaryl, or
a substituted or unsubstituted C$_6$- aryl or a substituted or unsubstituted C$_5$-C$_6$-heteroaryl, wherein in particular the substituted C$_6$- aryl or the substituted C$_5$-C$_6$-heteroaryl comprises at least one substituent $Z^2$.

In some embodiments, particularly of the first sub aspect, $R^2$ is selected from
a substituted alkyl, alkenyl or alkynyl, wherein the substituted alkyl, alkenyl or alkynyl comprises the formula 4a

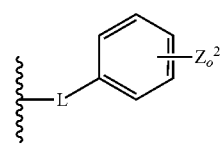

(formula 4a)

or
a substituted or unsubstituted C$_6$- aryl, wherein the substituted C$_6$ aryl comprises the formula 4b

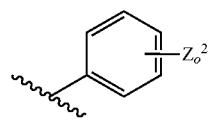

(formula 4b)

with L being
an alkyl, in particular a C$_1$-C$_{12}$ alkyl, more particularly a C$_1$-C$_4$ alkyl,
an alkenyl, in particular a C$_1$-C$_{12}$ alkenyl, more particularly a C$_1$-C$_4$ alkenyl,
an alkynyl, in particular a C$_1$-C$_{12}$ alkynyl, more particularly a C$_1$-C$_4$ alkynyl, and
o of $Z^2_o$ is 0, 1, 2, 3, 4 or 5, in particular 0, 1, 2 or 3, more particularly 0 or 1, and
each $Z^2$ independently from any other $Z^2$ is selected from —F, —Cl, —Br, —I, CN, —R$^b$, —OR$^b$, —(CH$_2$)$_r$OR$^b$, —SR$^b$, —(CH$_2$)$_r$SR$^b$ or —NR$^b_2$, with each R$^b$ being selected independently from each other from H, a substituted or unsubstituted C$_1$-C$_{12}$ alkyl, in particular C$_1$-C$_4$ alkyl, a substituted or unsubstituted C$_2$-C$_{12}$ alkenyl, in particular C$_2$-C$_4$ alkenyl, or a substituted or unsubstituted C$_2$-C$_{12}$ alkynyl, in particular C$_2$-C$_4$ alkynyl, with r being 1, 2, 3 or 4, in particular r is 1.

In some embodiments, particularly of the first sub aspect, o of $Z^2_o$ is 0, 1, 2, 3, 4 or 5, in particular 0, 1, 2 or 3, more particularly 0 or 1, and each $Z^2$ is selected independently from any other $Z^2$ from —F, —Cl, —Br, —I, CN, —R$^b$, —OR$^b$, CH$_2$OR$^b$ or —NR$^b_2$, in particular from —F, —Cl, —R$^b$, —OR$^b$, CH$_2$OR$^b$ or —NR$^b_2$, more particularly from —F, —Cl, —R$^b$, with each R$^b$ being selected independently from each other from H, a substituted or unsubstituted C$_1$-C$_{12}$ alkyl, in particular C$_1$-C$_4$ alkyl, a substituted or unsubstituted $C_2$-$C_{12}$ alkenyl, in particular $C_2$-$C_4$ alkenyl, or a substituted or unsubstituted $C_2$-$C_{12}$ alkynyl, in particular $C_2$-$C_4$ alkynyl, In some embodiments, particularly of the first sub aspect, o of $Z^2_o$ is 0, 1, 2, 3, 4 or 5, in particular 0, 1, 2 or 3, more particularly 0 or 1, and each $Z^2$ is selected independently from any other $Z^2$ from —F, —Cl, —Br, —I or —$R^b$, in particular from $R^b$, with $R^b$ being selected from a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl or a substituted or unsubstituted $C_2$-$C_{12}$ alkynyl, in particular $C_2$-$C_4$ alkynyl.

In some embodiments, particularly of the first sub aspect, o of $Z^2_o$ is 0

In some embodiments, particularly of the first sub aspect, $R^3$ is selected from a substituted or unsubstituted alkyl, in particular a substituted or unsubstituted $C_1$-$C_{10}$ alkyl, a substituted or unsubstituted alkenyl, in particular a substituted or unsubstituted $C_1$-$C_{10}$ alkenyl, a substituted or unsubstituted alkynyl, in particular a substituted or unsubstituted $C_1$-$C_{10}$ alkynyl, a substituted or unsubstituted cycloalkyl, in particular a substituted or unsubstituted $C_3$-$C_{10}$ cycloalkyl, a substituted or unsubstituted aryl, in particular a substituted or unsubstituted $C_6$-$C_{10}$ aryl, a substituted or unsubstituted heteroaryl, in particular a substituted or unsubstituted $C_5$-$C_{10}$ heteroaryl.

In some embodiments, particularly of the first sub aspect, $R^3$ is selected from a substituted or unsubstituted alkyl, in particular a substituted or unsubstituted $C_1$-$C_{10}$ alkyl, a substituted or unsubstituted alkenyl, in particular a substituted or unsubstituted $C_1$-$C_{10}$ alkenyl, a substituted or unsubstituted alkynyl, in particular a substituted or unsubstituted $C_1$-$C_{10}$ alkynyl, a substituted or unsubstituted aryl, in particular a substituted or unsubstituted $C_6$-$C_{10}$ aryl, or a substituted or unsubstituted heteroaryl, in particular a substituted or unsubstituted $C_5$-$C_{10}$ heteroaryl.

In some embodiments, particularly of the first sub aspect, $R^3$ is selected from a substituted or unsubstituted $C_1$-$C_4$ alkyl, a substituted or unsubstituted $C_1$-$C_4$ alkenyl, a substituted or unsubstituted $C_1$-$C_4$ alkynyl, a substituted or unsubstituted $C_6$ aryl, a substituted or unsubstituted $C_6$-cycloalkyl; or a substituted or unsubstituted $C_5$-$C_6$- heteroaryl, in particular a substituted or unsubstituted $C_6$-cycloalkyl or a substituted or unsubstituted $C_5$-$C_6$- heteroaryl.

In some embodiments, particularly of the first sub aspect, $R^3$ is selected from
a substituted alkyl, alkenyl or alkynyl, wherein the substituted alkyl, alkenyl or alkynyl comprises the formula -D-Ar,
with D being
an alkyl, in particular a $C_1$-$C_{12}$ alkyl, more particularly a $C_1$-$C_4$ alkyl,
an alkenyl, in particular a $C_1$-$C_{12}$ alkenyl, more particularly a $C_1$-$C_4$ alkenyl,
an alkynyl, in particular a $C_1$-$C_{12}$ alkynyl, more particularly a $C_1$-$C_4$ alkynyl, and
Ar being a substituted or unsubstituted $C_5$-$C_6$- aryl or a substituted or unsubstituted $C_5$-$C_6$- heteroaryl, or
a substituted or unsubstituted $C_6$- aryl or a substituted or unsubstituted $C_5$-$C_6$-heteroaryl, wherein in particular the substituted $C_6$- aryl or the substituted $C_5$-$C_6$-heteroaryl comprises at least one substituent $Z^3$.

In some embodiments, particularly of the first sub aspect, $R^3$ is selected from
a substituted alkyl, alkenyl or alkynyl, wherein the substituted alkyl, alkenyl or alkynyl comprises the formula 5a

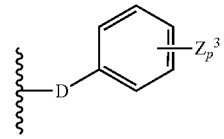

(formula 5a)

or
a substituted or unsubstituted $C_6$- aryl, wherein the substituted $C_6$ aryl comprises the formula 5b

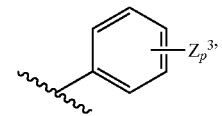

(formula 5b)

in particular the formula 5b,
with D being
an alkyl, in particular a $C_1$-$C_{12}$ alkyl, more particularly a $C_1$-$C_4$ alkyl,
an alkenyl, in particular a $C_1$-$C_{12}$ alkenyl, more particularly a $C_1$-$C_4$ alkenyl,
an alkynyl, in particular a $C_1$-$C_{12}$ alkynyl, more particularly a $C_1$-$C_4$ alkynyl, and
p of $Z^3_p$ is 0, 1, 2, 3, 4 or 5, in particular 0, 1, 2 or 3, more particularly 0 or 1, and
each $Z^3$ independently from any other $Z^3$ is selected from —F, —Cl, —Br, —I, CN, —$R^d$, —$OR^d$, —$(CH_2)_rOR^d$ —$SR^d$, —$(CH_2)_rSR^d$ or —$NR^d_2$, with each $R^d$ being selected independently from each other from H, a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl, or a substituted or unsubstituted $C_2$-$C_{12}$ alkynyl, in particular $C_2$-$C_4$ alkynyl, with r being 1, 2, 3 or 4, in particular r is 1.

In some embodiments, particularly of the first sub aspect, p of $Z^3_p$ is 0, 1, 2, 3, 4 or 5, in particular 0, 1, 2 or 3, more particularly 0 or 1, and each $Z^3$ is selected independently from any other $Z^3$ from —F, —Cl, —Br, —I, CN, —$R^d$, —$OR^d$, $CH_2OR^d$ or —$NR^d_2$, in particular from —F, —Cl, —$R^d$, —$OR^d$, $CH_2OR^d$ or —$NR^d_2$, more particularly from —F, —Cl, —$R^d$, with each $R^d$ being selected independently from each other from H, a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl, or a substituted or unsubstituted $C_2$-$C_{12}$ alkynyl, in particular $C_2$-$C_4$ alkynyl.

In some embodiments, particularly of the first sub aspect, p of $Z^3_p$ is 0, 1, 2, 3, 4 or 5, in particular 0, 1, 2 or 3, more particularly 0 or 1, and each $Z^3$ is selected independently from any other $Z^3$ from —F, —Cl, —Br, —I or —$R^d$, in particular from $R^d$, with $R^d$ being selected from a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl or a substituted or unsubstituted $C_2$-$C_{12}$ alkynyl, in particular $C_2$-$C_4$ alkynyl.

In some embodiments, particularly of the first sub aspect, p of $Z^3_p$ is 0.

In some embodiments, particularly of the first sub aspect, $R^1$ comprises the general formula 2e,

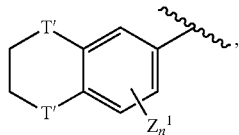

(2e)

with T' being O and n of $Z_n^1$ being 0, and
$R^3$ is selected from a substituted or unsubstituted cycloalkyl, in particular a substituted or unsubstituted $C_3$-$C_{10}$ cycloalkyl, more particularly cyclohexane $Z_n^1$, $R^4$ and $R^5$ having the same meaning as defined previously, and
$R^2$ is selected from
- a substituted or unsubstituted cycloalkyl, in particular a substituted or unsubstituted $C_3$-$C_{10}$ cycloalkyl,
- a substituted or unsubstituted aryl, in particular a substituted or unsubstituted $C_{6-10}$ aryl,
- a substituted or unsubstituted saturated heterocycle, in particular a substituted or unsubstituted $C_3$-$C_{10}$ heterocycle, or
- a substituted or unsubstituted heteroaryl, in particular a substituted or unsubstituted $C_5$-$C_{10}$ heteroaryl, or $R^2$ is selected from
- a substituted or unsubstituted $C_3$-$C_6$ cycloalkyl, a substituted or unsubstituted $C_6$ aryl, or a substituted or unsubstituted $C_5$-$C_6$- heteroaryl, or $R^2$ is selected from
- a substituted alkyl, alkenyl or alkynyl, wherein the substituted alkyl, alkenyl or alkynyl comprises the formula -L-Ar,
  with L being
    an alkyl, in particular a $C_1$-$C_{12}$ alkyl, more particularly a $C_1$-$C_4$ alkyl,
    an alkenyl, in particular a $C_1$-$C_{12}$ alkenyl, more particularly a $C_1$-$C_4$ alkenyl,
    an alkynyl, in particular a $C_1$-$C_{12}$ alkynyl, more particularly a $C_1$-$C_4$ alkynyl, and
  Ar being a substituted or unsubstituted $C_5$-$C_6$- aryl or a substituted or unsubstituted $C_5$-$C_6$- heteroaryl, or
- a substituted or unsubstituted $C_6$- aryl or a substituted or unsubstituted $C_5$-$C_6$- heteroaryl, wherein in particular the substituted $C_6$- aryl or the substituted $C_5$-$C_6$- heteroaryl comprises at least one substituent $Z^2$, or $R^2$ is selected from
- a substituted alkyl, alkenyl or alkynyl, wherein the substituted alkyl, alkenyl or alkynyl comprises the formula 4a

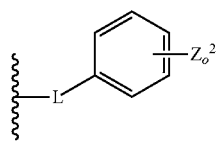

(formula 4a)

or
- a substituted or unsubstituted $C_6$- aryl, wherein the substituted $C_6$ aryl comprises the formula 4b

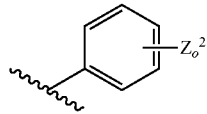

(formula 4b)

with L being
  an alkyl, in particular a $C_1$-$C_{12}$ alkyl, more particularly a $C_1$-$C_4$ alkyl,
  an alkenyl, in particular a $C_1$-$C_{12}$ alkenyl, more particularly a $C_1$-$C_4$ alkenyl,
  an alkynyl, in particular a $C_1$-$C_{12}$ alkynyl, more particularly a $C_1$-$C_4$ alkynyl, and
o of $Z_o^2$ is 0, 1, 2, 3, 4 or 5, in particular 0, 1, 2 or 3, more particularly 0 or 1, and
  each $Z^2$ independently from any other $Z^2$ is selected from —F, —Cl, —Br, —I, CN, —$R^b$, —$OR^b$, —$(CH_2)_rOR^b$, —$SR^b$, —$(CH_2)_rSR^b$ or —$NR^b_2$, with each $R^b$ being selected independently from each other from H, a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl, or a substituted or unsubstituted $C_2$-$C_{12}$ alkynyl, in particular $C_2$-$C_4$ alkynyl, with r being 1, 2, 3 or 4, in particular r is 1, or
o of $Z_o^2$ is 0, 1, 2, 3, 4 or 5, in particular 0, 1, 2 or 3, more particularly 0 or 1, and each $Z^2$ is selected independently from any other $Z^2$ from —F, —Cl, —Br, —I, CN, —$R^b$, —$OR^b$, $CH_2OR^b$ or —$NR^b_2$, in particular from —F, —Cl, —$R^b$, —$OR^b$, $CH_2OR^b$ or —$NR^b_2$, more particularly from —F, —Cl, —$R^b$, with each $R^b$ being selected independently from each other from H, a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl, or a substituted or unsubstituted $C_2$-$C_{12}$ alkynyl, in particular $C_2$-$C_4$ alkynyl, or
o of $Z_o^2$ is 0, 1, 2, 3, 4 or 5, in particular 0, 1, 2 or 3, more particularly 0 or 1, and each $Z^2$ is selected independently from any other $Z^2$ from —F, —Cl, —Br, -1 or —$R^b$, in particular from $R^b$, with $R^b$ being selected from a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl or a substituted or unsubstituted $C_2$-$C_{12}$ alkynyl, in particular $C_2$-$C_4$ alkynyl,
o of $Z_o^2$ is 0, or
$R^2$ is selected from

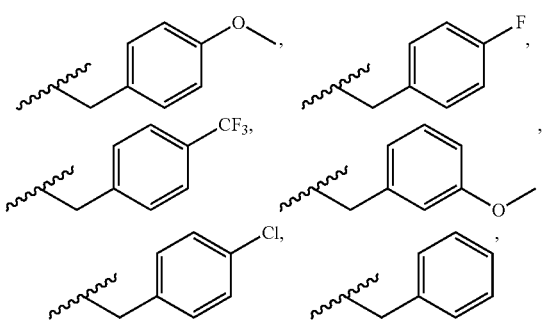

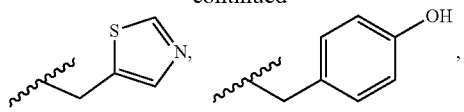

wherein the structure is exploratory and OH is in ortho, para or meta position to the attachment position to the parent moiety,

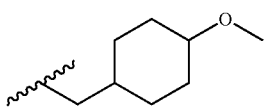 [SMILES: *CC1CCC(OC)CC1]

wherein the structure is exploratory and OCH$_3$ is in ortho, para or meta position to the attachment position to the parent moiety,

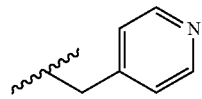

wherein the structure is exploratory and N is in ortho, para or meta position to the attachment position to the parent moiety, Particular embodiments of the first sub aspect are:

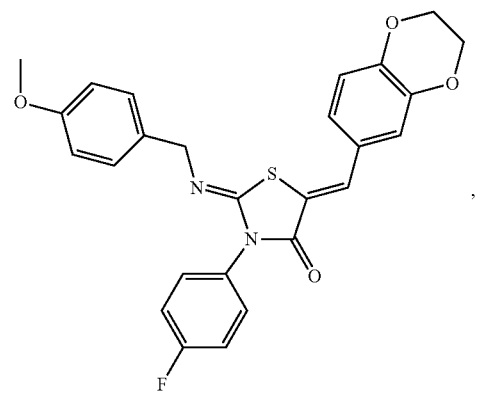

,

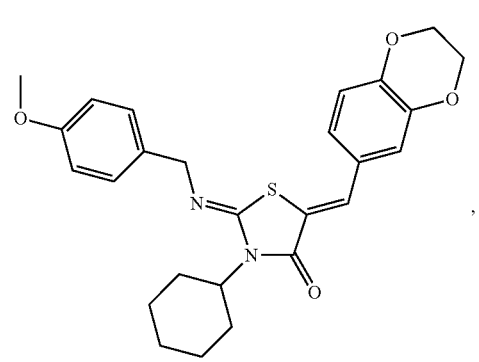

,

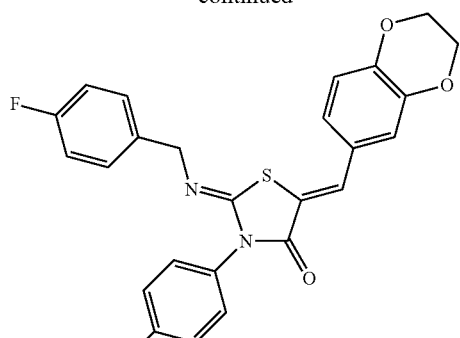

,

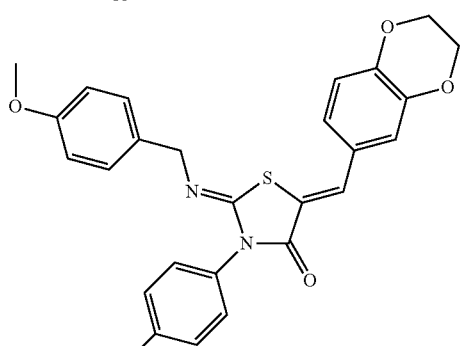

,

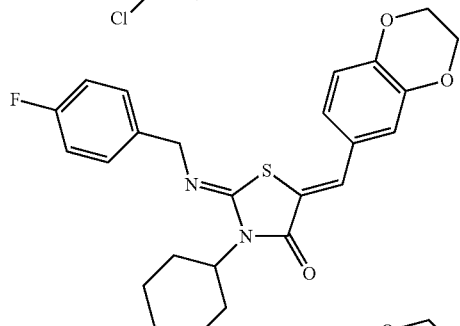

,

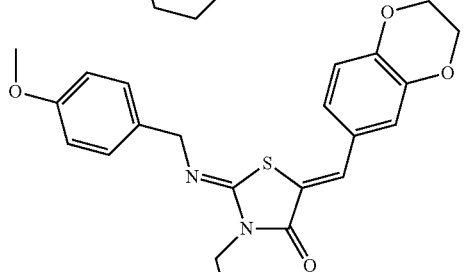

,

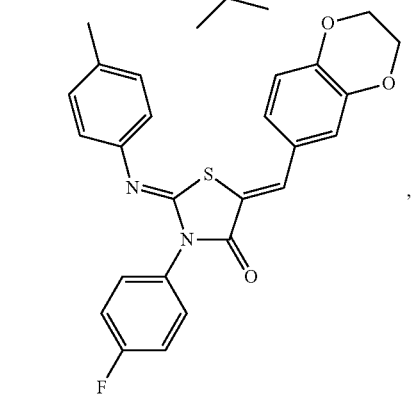

,

-continued
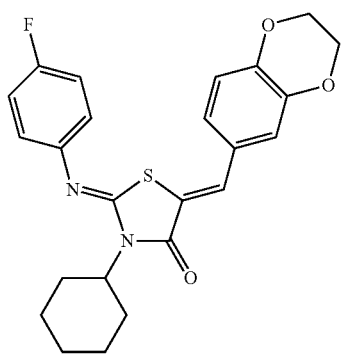,
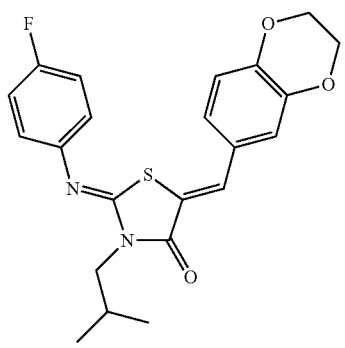,
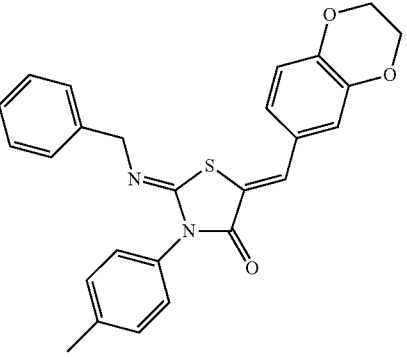,
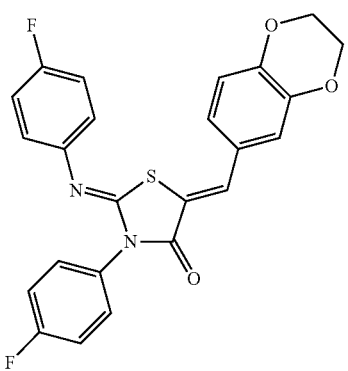,
-continued
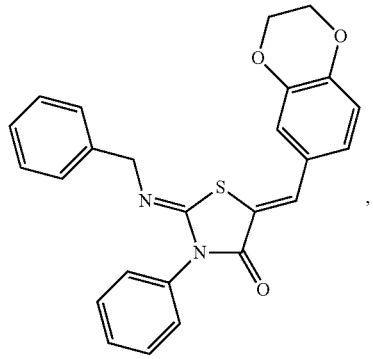,
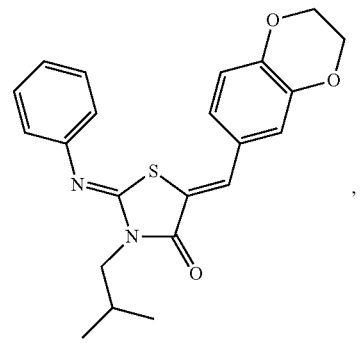,
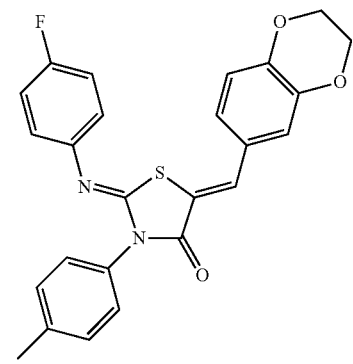,
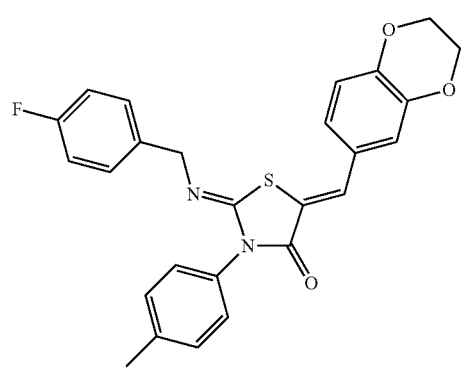,

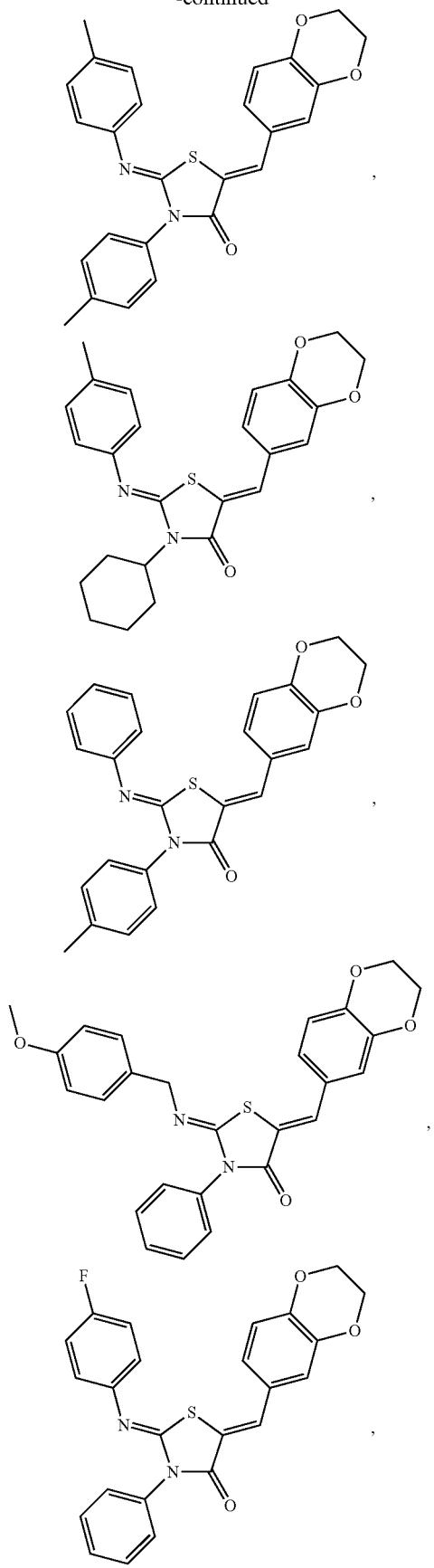
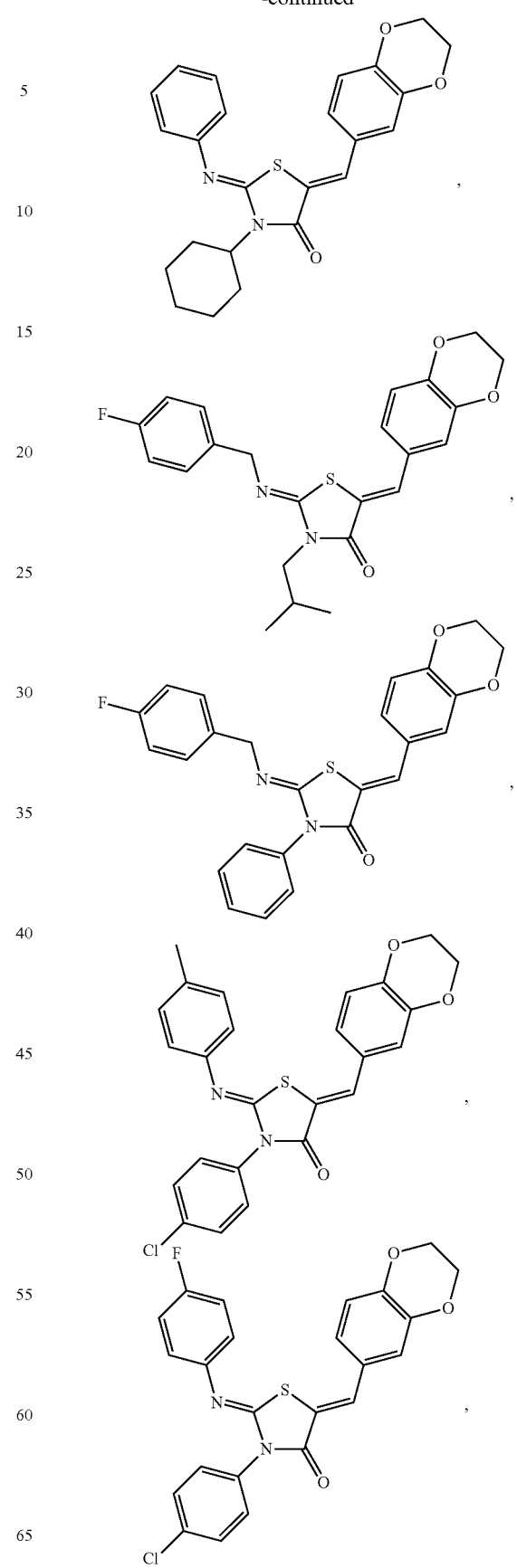

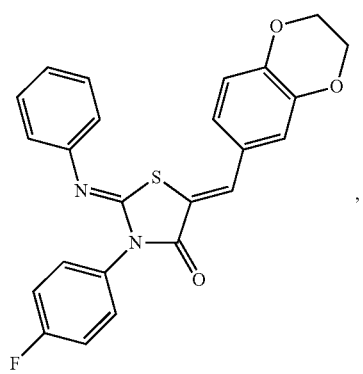
,
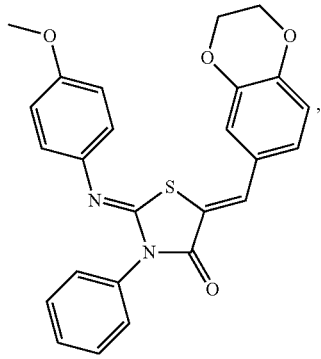
,
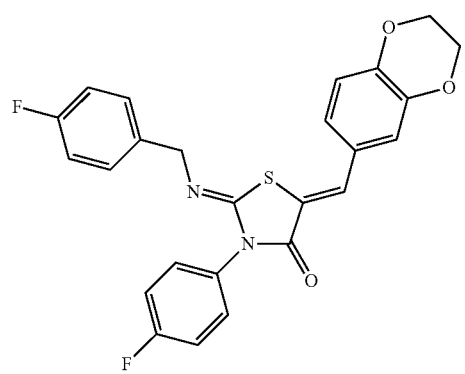
,
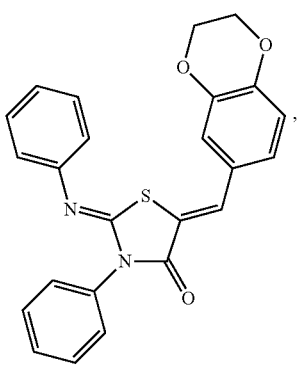
,
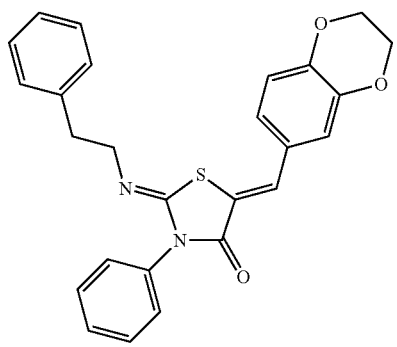
,
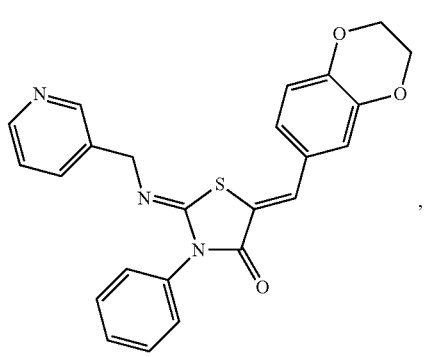
,
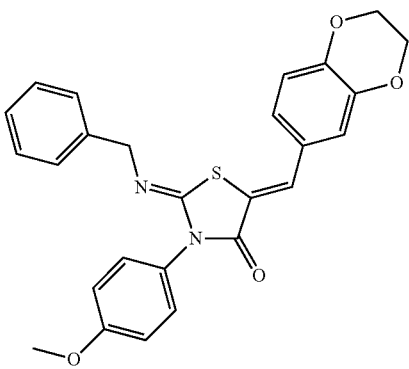
, 49
-continued
50
-continued
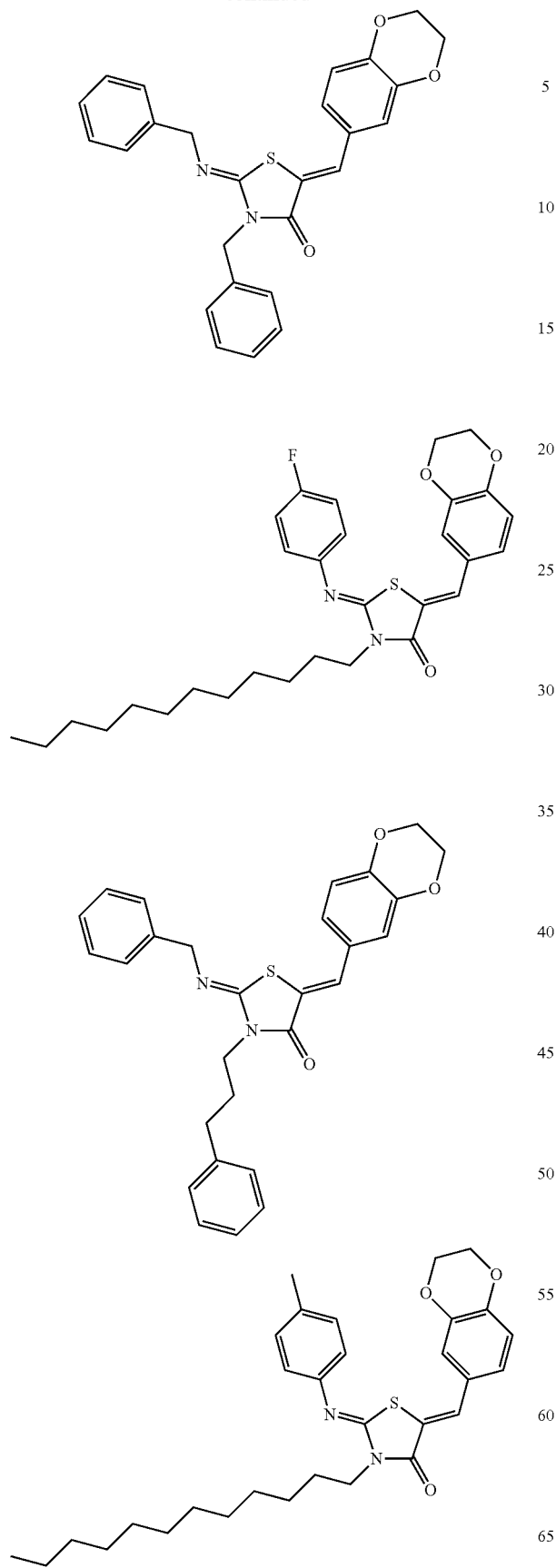
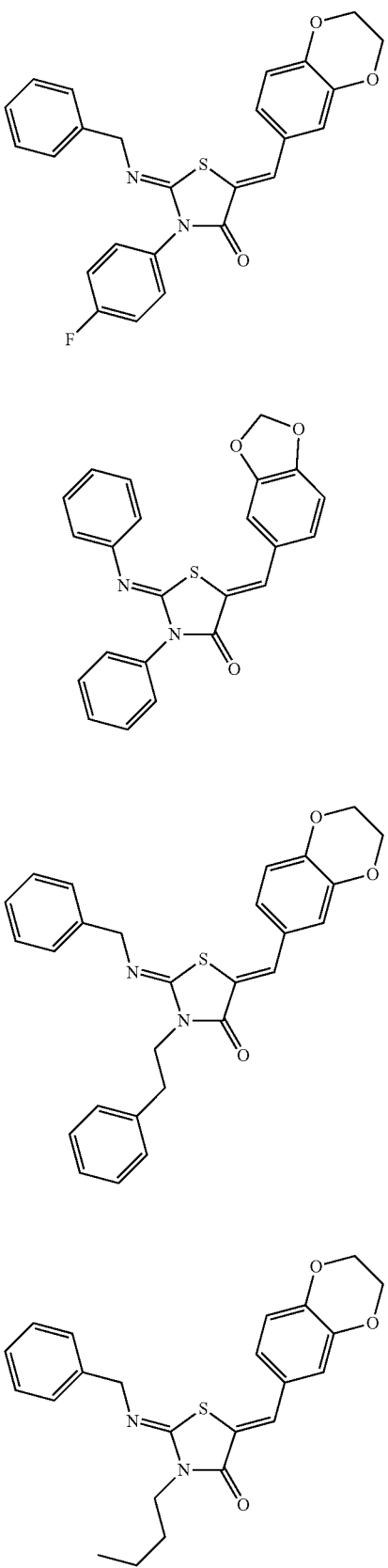

51
-continued

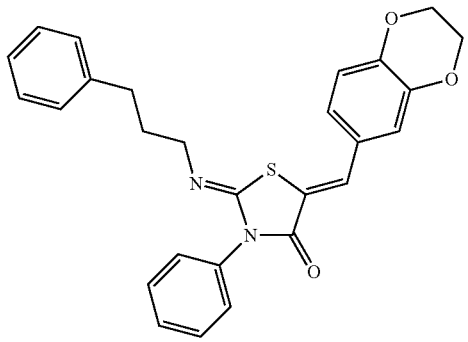

52
-continued

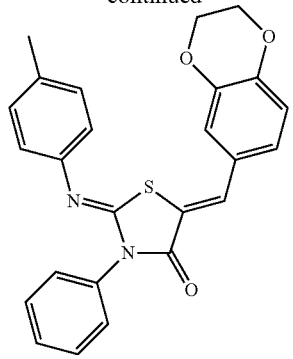

The IUPAC name is given below:

| ETI-T-compound | IUPAC name |
| --- | --- |
| 24_Q_B | (2Z,5Z)-2-(4-methoxybenzylimino)-3-(4-fluorophenyl)-5-((2,3-dihydrobenzo[b][1,4]dioxin-6-yl)methylene)thiazolidin-4-one |
| 24_Q_I | (2Z,5Z)-2-(4-methoxybenzylimino)-3-cyclohexyl-5-((2,3-dihydrobenzo[b][1,4]dioxin-6-yl)methylene)thiazolidin-4-one |
| 24_P_L | (2Z,5Z)-2-(4-fluorobenzylimino)-3-(4-chlorophenyl)-5-((2,3-dihydrobenzo[b][1,4]dioxin-6-yl)methylene)thiazolidin-4-one |
| 24_Q_L | (2Z,5Z)-2-(4-methoxybenzylimino)-3-(4-chlorophenyl)-5-((2,3-dihydrobenzo[b][1,4]dioxin-6-yl)methylene)thiazolidin-4-one |
| 24_P_I | (2Z,5Z)-2-(4-fluorobenzylimino)-3-cyclohexyl-5-((2,3-dihydrobenzo[b][1,4]dioxin-6-yl)methylene)thiazolidin-4-one |
| 24_Q_X | (2Z,5Z)-2-(4-methoxybenzylimino)-5-((2,3-dihydrobenzo[b][1,4]dioxin-6-yl)methylene)-3-isobutylthiazolidin-4-one |
| 24_A_B | (2Z,5Z)-5-(2,3-dihydro-1,4-benzodioxin-6-ylmethylene)-3-(4-fluorophenyl)-2-(p-tolylimino)thiazolidin-4-one |
| 24_B_I | (2Z,5Z)-2-(4-fluorophenylimino)-3-cyclohexyl-5-((2,3-dihydrobenzo[b][1,4]dioxin-6-yl)methylene)thiazolidin-4-one |
| 24_B_X | (2Z,5Z)-2-(4-fluorophenylimino)-5-((2,3-dihydrobenzo[b][1,4]dioxin-6-yl)methylene)-3-isobutylthiazolidin-4-one |
| 24_Q_A | (2Z,5Z)-2-(4-methoxybenzylimino)-5-((2,3-dihydrobenzo[b][1,4]dioxin-6-yl)methylene)-3-p-tolylthiazolidin-4-one |
| 24_B_B | (2Z,5Z)-2-(4-fluorophenylimino)-3-(4-fluorophenyl)-5-((2,3-dihydrobenzo[b][1,4]dioxin-6-yl)methylene)thiazolidin-4-one |
| 24_C_N | (2Z,5Z)-2-(benzylimino)-5-((2,3-dihydrobenzo[b][1,4]dioxin-6-yl)methylene)-3-phenylthiazolidin-4-one |
| 24_N_X | (2Z,5Z)-5-((2,3-dihydrobenzo[b][1,4]dioxin-6-yl)methylene)-3-isobutyl-2-(phenylimino)thiazolidin-4-one |
| 24_B_A | (2Z,5Z)-2-(4-fluorophenylimino)-5-((2,3-dihydrobenzo[b][1,4]dioxin-6-yl)methylene)-3-p-tolylthiazolidin-4-one |
| 24_P_A | (2Z,5Z)-2-(4-fluorobenzylimino)-5-((2,3-dihydrobenzo[b][1,4]dioxin-6-yl)methylene)-3-p-tolylthiazolidin-4-one |
| 24_A_A | (2Z,5Z)-2-(p-tolylimino)-5-((2,3-dihydrobenzo[b][1,4]dioxin-6-yl)methylene)-3-p-tolylthiazolidin-4-one |
| 24_A_I | (2Z,5Z)-3-cyclohexyl-5-(2,3-dihydro-1,4-benzodioxin-6-ylmethylene)-2-(p-tolylimino)thiazolidin-4-one |
| 24_N_A | (2Z,5Z)-5-((2,3-dihydrobenzo[b][1,4]dioxin-6-yl)methylene)-2-(phenylimino)-3-p-tolylthiazolidin-4-one |
| 24_Q_N | (2Z,5Z)-2-(4-methoxybenzylimino)-5-((2,3-dihydrobenzo[b][1,4]dioxin-7-yl)methylene)-3-phenylthiazolidin-4-one |
| 24_B_N | (2Z,5Z)-2-(4-fluorophenylimino)-5-((2,3-dihydrobenzo[b][1,4]dioxin-6-yl)methylene)-3-phenylthiazolidin-4-one |
| 24_N_I | (2Z,5Z)-3-cyclohexyl-5-((2,3-dihydrobenzo[b][1,4]dioxin-6-yl)methylene)-2-(phenylimino)thiazolidin-4-one |
| 24_P_X | (2Z,5Z)-2-(4-fluorobenzylimino)-5-((2,3-dihydrobenzo[b][1,4]dioxin-6-yl)methylene)-3-isobutylthiazolidin-4-one |
| 24_P_N | (2Z,5Z)-2-(4-fluorobenzylimino)-5-((2,3-dihydrobenzo[b][1,4]dioxin-6-yl)methylene)-3-phenylthiazolidin-4-one |
| 24_A_L | (2Z,5Z)-2-(p-tolylimino)-3-(4-chlorophenyl)-5-((2,3-dihydrobenzo[b][1,4]dioxin-6-yl)methylene)thiazolidin-4-one |
| 24_B_L | (2Z,5Z)-2-(4-fluorophenylimino)-3-(4-chlorophenyl)-5-((2,3-dihydrobenzo[b][1,4]dioxin-6-yl)methylene)thiazolidin-4-one |
| 24_N_B | (2Z,5Z)-3-(4-fluorophenyl)-5-((2,3-dihydrobenzo[b][1,4]dioxin-6-yl)methylene)-2-(phenylimino)thiazolidin-4-one |
| 24_A_X | (2Z,5Z)-2-(p-tolylimino)-5-((2,3-dihydrobenzo[b][1,4]dioxin-6-yl)methylene)-3-isobutylthiazolidin-4-one |
| 24 | (2Z,5Z)-5-((2,3-dihydrobenzo[b][1,4]dioxin-6-yl)methylene)-3-phenyl-2-(phenylimino)thiazolidin-4-one |

| ETI-T-compound | IUPAC name |
|---|---|
| 24_F_N | (2Z,5Z)-2-(4-methoxyphenylimino)-5-((2,3-dihydrobenzo[b][1,4]dioxin-6-yl)methylene)-3-phenylthiazolidin-4-one |
| 24_P_B | (2Z,5Z)-2-(4-fluorobenzylimino)-3-(4-fluorophenyl)-5-((2,3-dihydrobenzo[b][1,4]dioxin-6-yl)methylene)thiazolidin-4-one |
| 24_S_N | (2Z,5Z)-2-((pyridin-3-yl)methylimino)-5-((2,3-dihydrobenzo[b][1,4]dioxin-7-yl)methylene)-3-phenylthiazolidin-4-one |
| 24_A_N | (2Z,5Z)-2-(p-tolylimino)-5-((2,3-dihydrobenzo[b][1,4]dioxin-6-yl)methylene)-3-phenylthiazolidin-4-one |
| 24_K_N | (2Z,5Z)-2-(3-phenylpropylimino)-5-((2,3-dihydrobenzo[b][1,4]dioxin-7-yl)methylene)-3-phenylthiazolidin-4-one |
| 24_C_G | (2Z,5Z)-2-(benzylimino)-3-butyl-5-((2,3-dihydrobenzo[b][1,4]dioxin-7-yl)methylene)thiazolidin-4-one |
| 24_C_O | (2Z,5Z)-2-(benzylimino)-5-((2,3-dihydrobenzo[b][1,4]dioxin-7-yl)methylene)-3-phenethylthiazolidin-4-one |
| 25 | (2Z,5Z)-5-((benzo[d][1,3]dioxol-5-yl)methylene)-3-phenyl-2-(phenylimino)thiazolidin-4-one |
| 24_C_B | (2Z,5Z)-2-(benzylimino)-3-(4-fluorophenyl)-5-((2,3-dihydrobenzo[b][1,4]dioxin-7-yl)methylene)thiazolidin-4-one |
| 24_A_V | (2Z,5Z)-2-(p-tolylimino)-3-dodecyl-5-((2,3-dihydrobenzo[b][1,4]dioxin-6-yl)methylene)thiazolidin-4-one |
| 24_C_K | (2Z,5Z)-2-(benzylimino)-5-((2,3-dihydrobenzo[b][1,4]dioxin-7-yl)methylene)-3-(3-phenylpropyl)thiazolidin-4-one |
| 24_B_V | (2Z,5Z)-2-(4-fluorophenylimino)-3-dodecyl-5-((2,3-dihydrobenzo[b][1,4]dioxin-6-yl)methylene)thiazolidin-4-one |
| 24_C_C | (2Z,5Z)-3-benzyl-2-(benzylimino)-5-((2,3-dihydrobenzo[b][1,4]dioxin-7-yl)methylene)thiazolidin-4-one |
| 24_C_F | (2Z,5Z)-2-(benzylimino)-5-((2,3-dihydrobenzo[b][1,4]dioxin-7-yl)methylene)-3-(4-methoxyphenyl)thiazolidin-4-one |
| 24_U_N | (2Z,5Z)-5-((2,3-dihydrobenzo[b][1,4]dioxin-7-yl)methylene)-2-(phenethylimino)-3-phenylthiazolidin-4-one |

Any embodiment described for $R^2$ or $R^3$ according to the first aspect of the invention may be combined with any embodiment described for $R^1$ according to the first sub aspect of first aspect of the invention.

In some embodiments of a second sub aspect of the first aspect, $R^1$ is selected from a substituted alkyl, in particular a substituted alky, alkenyl or alkynyl, wherein the substituted alkyl, alkenyl or alkynyl comprises the formula 6a

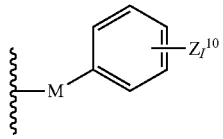

(formula 6a)

or a substituted or unsubstituted heterocycle, in particular a substituted or unsubstituted $C_3$-$C_{10}$ heterocycle, or a substituted or unsubstituted heteroaryl, in particular a substituted or unsubstituted $C_5$-$C_{10}$ heteroaryl, a substituted or unsubstituted $C_6$- aryl, wherein the substituted $C_6$ aryl comprises the formula 6b

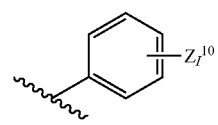

(formula 6b)

with M being an alkyl, in particular a $C_1$-$C_{12}$ alkyl, more particularly a $C_1$-$C_4$ alkyl, an alkenyl, in particular a $C_1$-$C_{12}$ alkenyl, more particularly a $C_1$-$C_4$ alkenyl, an alkynyl, in particular a $C_1$-$C_{12}$ alkynyl, more particularly a $C_1$-$C_4$ alkynyl, and I of $Z^{10}_I$ is 0, 1, 2, 3, 4 or 5, in particular 0, 1 or 2, more particularly 0 or 1, and each $Z^{10}$ independently from any other $Z^{10}$ is selected from —F, —Cl, —Br, —I, CN, —$R^e$, —$OR^e$, —$(CH_2)_rOR^e$, —$SR^e$, —$(CH_2)_rSR^e$ or —$NR^e_2$, with each $R^e$ being selected independently from each other from H, a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl, or a substituted or unsubstituted $C_2$-$C_{12}$ alkynyl, in particular $C_2$-$C_4$ alkynyl, with r being 1, 2, 3 or 4, in particular r is 1.

and $R^2$ is selected from a substituted or unsubstituted alkyl, in particular a substituted or unsubstituted $C_1$-$C_{12}$ alkyl, a substituted or unsubstituted alkoxy, in particular a substituted or unsubstituted $C_1$-$C_{12}$ alkoxy, a substituted or unsubstituted alkenyl, in particular a substituted or unsubstituted $C_1$-$C_{12}$ alkenyl, a substituted or unsubstituted alkynyl, in particular a substituted or unsubstituted $C_1$-$C_{12}$ alkynyl, a substituted or unsubstituted cycloalkyl, in particular a substituted or unsubstituted $C_3$-$C_{10}$ cycloalkyl, a substituted or unsubstituted aryl, in particular a substituted or unsubstituted $C_6$-$C_{10}$ aryl, a substituted or unsubstituted saturated heterocycle, in particular a substituted or unsubstituted $C_3$-$C_{10}$ heterocycle, or a substituted or unsubstituted heteroaryl, in particular a substituted or unsubstituted $C_5$-$C_{10}$ heteroaryl, and $R^3$ is selected from a substituted or unsubstituted cycloalkyl, in particular a substituted or unsubstituted $C_3$-$C_{10}$ cycloalkyl, more particularly cyclohexane Concerning embodiments of $R_1$ with respect to a substituted or unsubstituted heterocycle, in particular a substituted or unsubstituted $C_3$-$C_{10}$ heterocycle, or a substituted or unsubstituted heteroaryl, in particular a substituted or unsubstituted $C_5$-$C_{10}$ heteroaryl, reference is made to the specific embodiments of the first aspect and the first and third sub aspect of the invention.

In some embodiments, particularly of the second sub aspect, $R^1$ is selected from
a substituted or unsubstituted $C_6$- aryl, wherein the $C_6$ aryl comprises the formula 6b

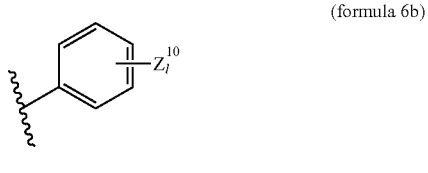

(formula 6b)

with M being an alkyl, in particular a $C_1$-$C_{12}$ alkyl, more particularly a $C_1$-$C_4$ alkyl, and I of $Z^{10}_I$ is 0, 1, 2, 3, 4 or 5, in particular 0, 1, 2 or 3, more particularly 0 or 1, and each $Z^{10}$ independently from any other $Z^{10}$ is selected from —F, —Cl, —Br, —I, CN, —$R^e$, —$OR^e$, —$(CH_2)_rOR^e$, —$SR^e$, —$(CH_2)_rSR^e$ or —$NR^e_2$, with each $R^e$ being selected independently from each other from H, a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl, or a substituted or unsubstituted $C_2$-$C_{12}$ alkynyl, in particular $C_2$-$C_4$ alkynyl, with r being 1, 2, 3 or 4, in particular r is 1.

In some embodiments, particularly of the second sub aspect, I of $Z^{10}_I$ is 0, 1, 2, 3, 4 or 5, in particular 0, 1, 2 or 3, more particularly 0 or 1, and each $Z^{10}$ is selected independently from any other $Z^{10}$ from —F, —Cl, —Br, —I, CN, —$R^e$, —$SR^e$, —$CH_2SR^e$, —$OR^e$, $CH_2OR^e$ or —$NR^e_2$, in particular from —F, —Cl, CN, —$R^e$, —$OR^e$, —$CH_2OR^e$ or —$NR^e_2$, more particularly from CN, —$OR^e$ or $CH_2OR^e$, with each $R^e$ being selected independently from each other from H, a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl, or a substituted or unsubstituted $C_2$-$C_{12}$ alkynyl, in particular $C_2$-$C_4$ alkynyl.

In some embodiments, particularly of the second sub aspect, I of $Z^{10}_I$ is 0, 1, 2, 3, 4 or 5, in particular 0, 1, 2 or 3, more particularly 0 or 1, and each $Z^3$ is selected independently from any other $Z^3$ from —F, —Cl, —Br, —I, CN, —$OR^e$ or —$CH_2OR^e$, in particular from $R^e$, with $R^e$ being selected from a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl or a substituted or unsubstituted $C_2$-$C_{12}$ alkynyl, in particular $C_2$-$C_4$ alkynyl.

In some embodiments, particularly of the second sub aspect, I of $Z^{10}_I$ is 0, 1 or 2, in particular 0 or 1.

In some embodiments, particularly of the second sub aspect, $R^1$ is selected from.

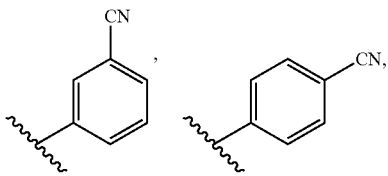

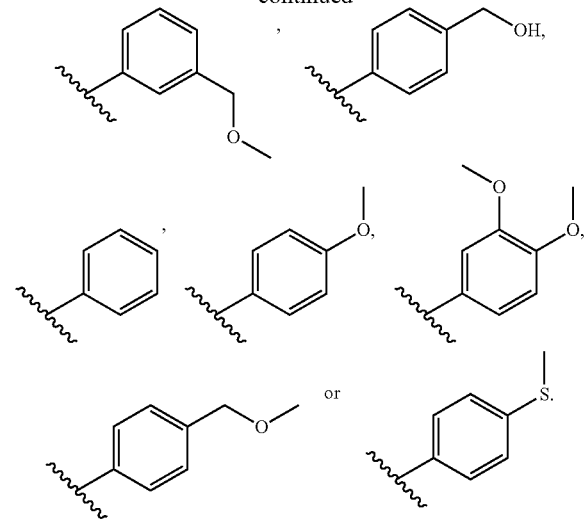

In some embodiments, particularly of the second sub aspect, $R^2$ is selected from a substituted or unsubstituted alkyl, in particular a substituted or unsubstituted $C_1$-$C_{10}$ alkyl, a substituted or unsubstituted alkenyl, in particular a substituted or unsubstituted $C_1$-$C_{10}$ alkenyl, a substituted or unsubstituted alkynyl, in particular a substituted or unsubstituted $C_1$-$C_{10}$ alkynyl, a substituted or unsubstituted cycloalkyl, in particular a substituted or unsubstituted $C_3$-$C_{10}$ cycloalkyl, a substituted or unsubstituted aryl, in particular a substituted or unsubstituted $C_6$-$C_{10}$ aryl, a substituted or unsubstituted heteroaryl, in particular a substituted or unsubstituted $C_5$-$C_{10}$ heteroaryl.

In some embodiments, particularly of the second sub aspect, $R^2$ is selected from a substituted or unsubstituted alkyl, in particular a substituted or unsubstituted $C_1$-$C_{10}$ alkyl, a substituted or unsubstituted alkenyl, in particular a substituted or unsubstituted $C_1$-$C_{10}$ alkenyl, a substituted or unsubstituted alkynyl, in particular a substituted or unsubstituted $C_1$-$C_{10}$ alkynyl, a substituted or unsubstituted aryl, in particular a substituted or unsubstituted $C_6$-$C_{10}$ aryl, or a substituted or unsubstituted heteroaryl, in particular a substituted or unsubstituted $C_5$-$C_{10}$ heteroaryl.

In some embodiments, particularly of the second sub aspect, $R^2$ is selected from a substituted or unsubstituted $C_1$-$C_4$ alkyl, a substituted or unsubstituted $C_1$-$C_4$ alkenyl, a substituted or unsubstituted $C_1$-$C_4$ alkynyl, a substituted or unsubstituted $C_6$ aryl, or a substituted or unsubstituted $C_5$-$C_6$- heteroaryl.

In some embodiments, particularly of the second sub aspect, $R^1$ comprises the general formula 2e,

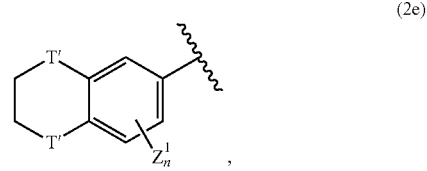

(2e)

with T' being O and n of $Z_n^1$ being 0, and $R^3$ is selected from a substituted or unsubstituted cycloalkyl, in particular a substituted or unsubstituted $C_3$-$C_{10}$ cycloalkyl, more particularly cyclohexane $Z_n^1$, $R^4$ and $R^5$ having the same meaning as defined previously, and $R^2$ is selected from
- a substituted or unsubstituted alkyl, in particular a substituted or unsubstituted $C_1$-$C_{12}$ alkyl,
- a substituted or unsubstituted alkoxy, in particular a substituted or unsubstituted $C_1$-$C_{12}$ alkoxy,
- a substituted or unsubstituted alkenyl, in particular a substituted or unsubstituted $C_1$-$C_{12}$ alkenyl,
- a substituted or unsubstituted alkynyl, in particular a substituted or unsubstituted $C_1$-$C_{12}$ alkynyl,
- a substituted or unsubstituted cycloalkyl, in particular a substituted or unsubstituted $C_3$-$C_{10}$ cycloalkyl,
- a substituted or unsubstituted aryl, in particular a substituted or unsubstituted $C_{6\text{-}10}$ aryl,
- a substituted or unsubstituted saturated heterocycle, in particular a substituted or unsubstituted $C_3$-$C_{10}$ heterocycle, or
- a substituted or unsubstituted heteroaryl, in particular a substituted or unsubstituted $C_5$-$C_{10}$ heteroaryl, or $R^2$ is selected from
- a substituted or unsubstituted cycloalkyl, in particular a substituted or unsubstituted $C_3$-$C_{10}$ cycloalkyl,
- a substituted or unsubstituted aryl, in particular a substituted or unsubstituted $C_6$-$C_{10}$ aryl,
- a substituted or unsubstituted saturated heterocycle, in particular a substituted or unsubstituted $C_3$-$C_{10}$ heterocycle, or
- a substituted or unsubstituted heteroaryl, in particular a substituted or unsubstituted $C_5$-$C_{10}$ heteroaryl, or $R^2$ is selected from
- a substituted or unsubstituted $C_3$-$C_6$ cycloalkyl, a substituted or unsubstituted $C_6$ aryl, or a substituted or unsubstituted $C_5$-$C_6$- heteroaryl, or $R^2$ is selected from
- a substituted alkyl, alkenyl or alkynyl, wherein the substituted alkyl, alkenyl or alkynyl comprises the formula -L-Ar,
  with L being
    - an alkyl, in particular a $C_1$-$C_{12}$ alkyl, more particularly a $C_1$-$C_4$ alkyl,
    - an alkenyl, in particular a $C_1$-$C_{12}$ alkenyl, more particularly a $C_1$-$C_4$ alkenyl,
    - an alkynyl, in particular a $C_1$-$C_{12}$ alkynyl, more particularly a $C_1$-$C_4$ alkynyl, and
  Ar being a substituted or unsubstituted $C_5$-$C_6$- aryl or a substituted or unsubstituted $C_5$-$C_6$- heteroaryl, or
  a substituted or unsubstituted $C_6$- aryl or a substituted or unsubstituted $C_5$-$C_6$- heteroaryl, wherein in particular the substituted $C_6$- aryl or the substituted $C_5$-$C_6$- heteroaryl comprises at least one substituent $Z^2$, or $R^2$ is selected from
- a substituted alkyl, alkenyl or alkynyl, wherein the substituted alkyl, alkenyl or alkynyl comprises the formula 4a

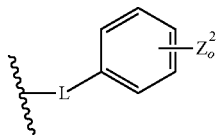

(formula 4a)

or
- a substituted or unsubstituted $C_6$- aryl, wherein the substituted $C_6$ aryl comprises the formula 4b

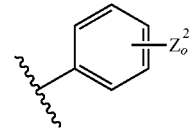

(formula 4b)

with L being
- an alkyl, in particular a $C_1$-$C_{12}$ alkyl, more particularly a $C_1$-$C_4$ alkyl,
- an alkenyl, in particular a $C_1$-$C_{12}$ alkenyl, more particularly a $C_1$-$C_4$ alkenyl,
- an alkynyl, in particular a $C_1$-$C_{12}$ alkynyl, more particularly a $C_1$-$C_4$ alkynyl, and o of $Z^2_o$ is 0, 1, 2, 3, 4 or 5, in particular 0, 1, 2 or 3, more particularly 0 or 1, and
  each $Z^2$ independently from any other $Z^2$ is selected from —F, —Cl, —Br, —I, CN, —$R^b$, —$OR^b$, —$(CH_2)_rOR^b$, —$SR^b$, —$(CH_2)_rSR^b$ or —$NR^b_2$, with each $R^b$ being selected independently from each other from H, a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl, or a substituted or unsubstituted $C_2$-$C_{12}$ alkynyl, in particular $C_2$-$C_4$ alkynyl, with r being 1, 2, 3 or 4, in particular r is 1, or o of $Z^2_o$ is 0, 1, 2, 3, 4 or 5, in particular 0, 1, 2 or 3, more particularly 0 or 1, and each $Z^2$ is selected independently from any other $Z^2$ from —F, —Cl, —Br, —I, CN, —$R^b$, —$OR^b$, $CH_2OR^b$ or —$NR^b_2$, in particular from —F, —Cl, —$R^b$, —$OR^b$, $CH_2OR^b$ or —$NR^b_2$, more particularly from —F, —Cl, —$R^b$, with each $R^b$ being selected independently from each other from H, a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl, or a substituted or unsubstituted $C_2$-$C_{12}$ alkynyl, in particular $C_2$-$C_4$ alkynyl, or o of $Z^2_o$ is 0, 1, 2, 3, 4 or 5, in particular 0, 1, 2 or 3, more particularly 0 or 1, and each $Z^2$ is selected independently from any other $Z^2$ from —F, —Cl, —Br, -1 or —$R^b$, in particular from $R^b$, with $R^b$ being selected from a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl or a substituted or unsubstituted $C_2$-$C_{12}$ alkynyl, in particular $C_2$-$C_4$ alkynyl, o of $Z^2_o$ is 0, or $R^2$ is selected from

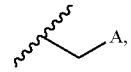

with A being —$(CH)(CH_3)_3$, —$(CH_2)CN$, —$(CH_2)C(=O)ONH_2$, —$(CH_2)N(CH_2CH_3)_2$, —$(CH_2)CH_2OH$, —$(CH_2)C(=O)NH_2$.

Particular embodiment is given below:

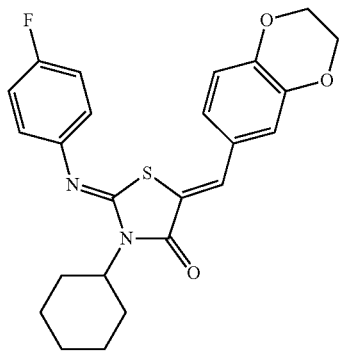 [SMILES: O=C1/C(=C/c2ccc3c(c2)OCCO3)S/C(=N\c2ccc(F)cc2)N1C1CCCCC1]

Concerning further embodiments of $R^2$ reference is made to the first aspect of the invention, particularly to the first sub aspect of first aspect of the invention.

Concerning further embodiments of o of $Z^2_o$ and $Z^2$ reference is made to the first aspect of the invention, particularly to the first sub aspect of first aspect of the invention.

In some embodiments of a third sub aspect of the first aspect, each of $R^2$ and $R^3$ are selected independently from each other from
- a substituted or unsubstituted alkyl, in particular a substituted or unsubstituted $C_1$-$C_{12}$ alkyl,
- a substituted or unsubstituted alkoxy, in particular a substituted or unsubstituted $C_1$-$C_{12}$ alkoxy,
- a substituted or unsubstituted alkenyl, in particular a substituted or unsubstituted $C_1$-$C_{12}$ alkenyl,
- a substituted or unsubstituted alkynyl, in particular a substituted or unsubstituted $C_1$-$C_{12}$ alkynyl,
- a substituted or unsubstituted cycloalkyl, in particular a substituted or unsubstituted $C_3$-$C_{10}$ cycloalkyl,
- a substituted or unsubstituted aryl, in particular a substituted or unsubstituted $C_6$-$C_{10}$ aryl,
- a substituted or unsubstituted saturated heterocycle, in particular a substituted or unsubstituted $C_3$-$C_{10}$ heterocycle, or
- a substituted or unsubstituted heteroaryl, in particular a substituted or unsubstituted $C_5$-$C_{10}$ heteroaryl, and $R^1$ comprises
a. the general formula 2b' to 2d' and 2f' to 2j', (2b')
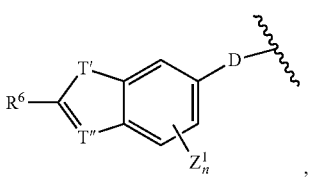

(2c')
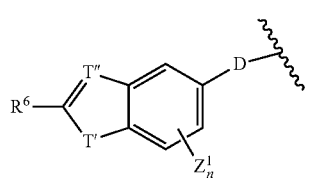

(2d')
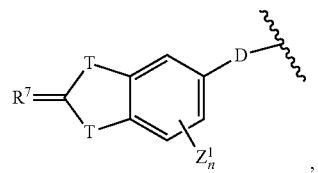

(2f')
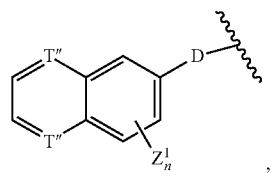

(2g')
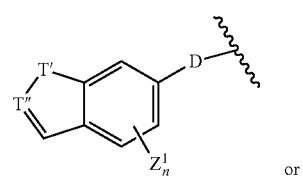

(2h')
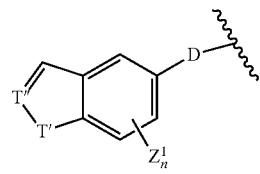

(2i')
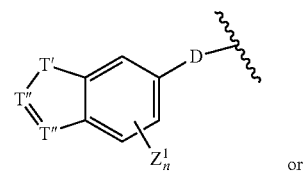

(2j')
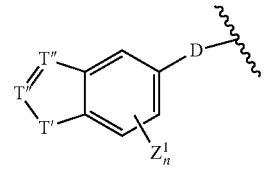

with D being a $C_1$ to $C_4$ alkyl, or $R^1$ comprises the general formula 2b to 2d and 2f to 2j (2b)
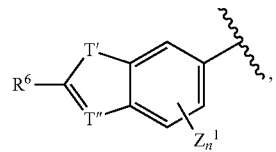

(2c)
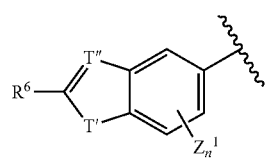

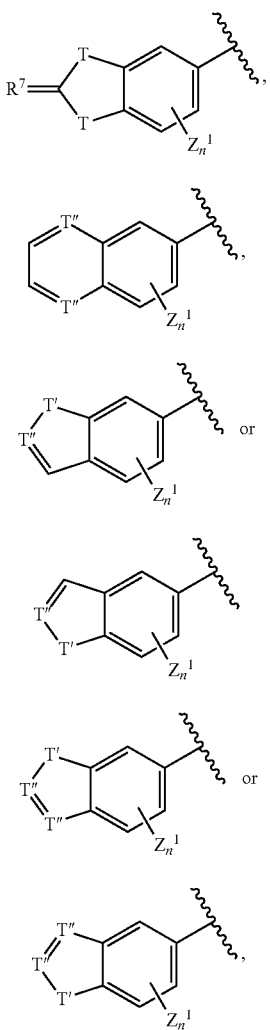

with each T being selected independently from each other from —CH$_2$, —NH, —S, —O, —CHCH$_3$, —C(CH$_3$)$_2$ or —NR$^c$, in particular from NH, —S or —O, and with T' being selected from —CH$_2$, —NH, —S, —O, —CHCH$_3$, —C(CH$_3$)$_2$ or —NR, and with each T" being selected independently from each other from being selected from —CH or =N, with R$^4$ and R$^5$ being selected independently from each other from —H, —F, —CH$_3$, —CH$_2$CH$_3$, —OCH$_3$, —CH$_2$CF$_3$, —CHFCF$_3$, —CF$_2$CF$_3$, —CHF$_2$, —CH$_2$F or —CF$_3$, in particular with R$^5$ and R$^6$ being selected independently from each other from H, —F or —CH$_3$, and with R$^6$ being selected from —OH, —OCH$_3$, —OCH$_2$CH$_3$, —CH$_3$ or H, with R$^7$ being selected from =NH, =S or =O, in particular from 0, and with n of Z$^1_n$ being 0, 1, 2 or 3, in particular n of Z$^1_n$ being 0 or 1, and with each Z$^1$ independently from any other Z$^1$ being selected from —F, —Cl, —Br, —I, CN, —R$^a$, —OR$^a$, —(CH$_2$)$_r$OR$^a$, —SR$^a$, —(CH$_2$)$_r$SR$^a$ or —NR$^a_2$, with each R$^a$ being selected independently from each other from H, a substituted or unsubstituted C$_1$-C$_8$ alkyl, in particular C$_1$-C$_4$ alkyl, a substituted or unsubstituted C$_2$-C$_8$ alkenyl, in particular C$_2$-C$_4$ alkenyl, or a substituted or unsubstituted C$_2$-C$_8$ alkynyl, in particular C$_2$-C$_4$ alkynyl, with r being 1, 2, 3 or 4, in particular r is 1, with R$^c$ being —CH$_2$OH, —CH$_3$, —CH$_2$CH$_3$, —CH$_2$CH$_2$CH$_3$, —CH(CH$_3$)$_2$, —CH$_2$CF$_3$, —CHFCF$_3$, —CF$_2$CF$_3$, —CHF$_2$, —CH$_2$F, —CF$_3$.

In some embodiments, particularly of the third sub aspect, R$^1$ comprises the general formula 2b to 2h, in particular the formula 2b, 2c, 2g or 2h, more particularly the formula 2b, 2c, 2g or 2h.

In some embodiments, particularly of the third sub aspect, R$^1$ comprises the general formula 2b or 2c, in particular 2c.

In some embodiments, particularly of the third sub aspect,

T' of the compound according to formula 2b or 2c is selected from —NH, —S, —O or —NR$^c$, wherein in particular T' is S or —NH, and T" being selected from —CH or =N, and with R$^6$ being selected from —CH$_3$ or H, in particular R$^6$ is H, each T of the compound according to formula 2d being selected independently from each other from —NH, —S, —O or —NR$^c$, in particular at least one T is selected from NH or —NCH$_3$, more particularly the T in the position 4, with respect to the connection to the parent moiety, is —NH, and with R$^7$ being selected from =NH, =S or =O, in particular from 0, and each T" of the compound according to formula 2f is selected independently from each other from —CH or =N, in particular each T" is =N, T' of the compound according to formula 2g or 2h is selected from —NH, —S, —O or —NR$^c$, wherein in particular T' is —NR$^c$ or —NH, and T" being selected from —CH or =N, in particular T" is =N, T' of the compound according to formula 2i or 2j is selected from —NH or —NR$^c$, wherein in particular T' is —NH, and T" is =N.

In some embodiments, particularly of the third sub aspect, R$^c$ is selected from —CH$_2$OH, —CH$_3$, —CH$_2$CH$_3$, —CH$_2$CH$_2$CH$_3$ or —CH(CH$_3$)$_2$, in particular from —CH$_3$, —CH$_2$CH$_3$ or —CH(CH$_3$)$_2$, more particularly R$^c$ is CH$_3$.

Concerning further embodiments of n of Z$^1_n$ and Z$^1_n$ reference is made to the first aspect of the invention, particularly to the first sub aspect of first aspect of the invention.

Concerning further embodiments of R$^2$ reference is made to the first aspect of the invention, particularly to the second sub aspect of first aspect of the invention.

Concerning further embodiments of o of Z$^2_o$ and Z$^2_o$ reference is made to the first aspect of the invention, particularly to the first sub aspect of first aspect of the invention.

Concerning further embodiments of R$^3$ reference is made to the first aspect of the invention, particularly to the second sub aspect of first aspect of the invention.

In some embodiments, particularly of the third sub aspect, R$^3$ is selected from a substituted or unsubstituted C$_1$-C$_4$ alkyl, a substituted or unsubstituted C$_1$-C$_4$ alkenyl, a substituted or unsubstituted C$_1$-C$_4$ alkynyl, a substituted or unsubstituted C$_6$ aryl, a substituted or unsubstituted C$_6$-cycloalkyl or a substituted or unsubstituted $C_5$-$C_6$- heteroaryl, in particular a substituted or unsubstituted $C_6$-cycloalkyl or a substituted or unsubstituted $C_5$-$C_6$- heteroaryl.

Concerning further more specific embodiments of $R^3$ reference is made to the first aspect of the invention, particularly to the second sub aspect of first aspect of the invention.

Concerning further embodiments of p of $Z^3_p$ and $Z^3_p$ reference is made to the first aspect of the invention, particularly to the first sub aspect of first aspect of the invention.

Particular embodiments of this sub aspect are given below:

| ETI-T-compound | IUPAC name |
|---|---|
| 04_A_N | (2Z,5Z)-5-((1H-benzo[d]imidazol-5-yl)methylene)-2-(p-tolylimino)-3-phenylthiazolidin-4-one |
| 04_B_I | (2Z,5Z)-5-((1H-benzo[d]imidazol-5-yl)methylene)-2-(4-fluorophenylimino)-3-cyclohexylthiazolidin-4-one |
| 04_A_X | (2Z,5Z)-5-((1H-benzo[d]imidazol-5-yl)methylene)-2-(p-tolylimino)-3-isobutylthiazolidin-4-one |
| 04_F_N | (2Z,5Z)-5-((1H-benzo[d]imidazol-5-yl)methylene)-2-(4-methoxyphenylimino)-3-phenylthiazolidin-4-one |
| 04 | (2Z,5Z)-5-((1H-benzo[d]imidazol-5-yl)methylene)-3-phenyl-2-(phenylimino)thiazolidin-4-one |
| 03_T_N | (2Z,5Z)-5-((1H-indol-5-yl)methylene)-2-(2-chlorobenzylimino)-3-phenylthiazolidin-4-one |
| 32 | (2Z,5Z)-5-((benzo[d]thiazol-6-yl)methylene)-3-phenyl-2-(phenylimino)thiazolidin-4-one |
| 03_A_A | (2Z,5Z)-5-((1H-indol-5-yl)methylene)-2-(p-tolylimino)-3-p-tolylthiazolidin-4-one |
| 32_A_X | (2Z,5Z)-2-(p-tolylimino)-5-((benzo[d]thiazol-6-yl)methylene)-3-isobutylthiazolidin-4-one |
| 32_A_I | (2Z,5Z)-2-(p-tolylimino)-5-((benzo[d]thiazol-6-yl)methylene)-3-cyclohexylthiazolidin-4-one |
| 28_A_X | (2Z,5Z)-2-(p-tolylimino)-3-isobutyl-5-((1-methyl-1H-indazol-5-yl)methylene)thiazolidin-4-one |
| 28_A_I | (2Z,5Z)-2-(p-tolylimino)-3-cyclohexyl-5-((1-methyl-1H-indazol-5-yl)methylene)thiazolidin-4-one |
| 04_A_A | (2Z,5Z)-5-((1H-benzo[d]imidazol-5-yl)methylene)-2-(p-tolylimino)-3-p-tolylthiazolidin-4-one |
| 03_P_N | (2Z,5Z)-5-((1H-indol-5-yl)methylene)-2-(4-fluorobenzylimino)-3-phenylthiazolidin-4-one |
| 03_B_X | (2Z,5Z)-5-((1H-indol-5-yl)methylene)-2-(4-fluorophenylimino)-3-isobutylthiazolidin-4-one |
| 04_C_F | (2Z,5Z)-5-((1H-benzo[d]imidazol-5-yl)methylene)-2-(benzylimino)-3-(4-methoxyphenyl)thiazolidin-4-one |
| 03_U_N | (2Z,5Z)-5-((1H-indol-5-yl)methylene)-2-(phenethylimino)-3-phenylthiazolidin-4-one |
| 28 | (2Z,5Z)-5-((1-methyl-1H-indazol-5-yl)methylene)-3-phenyl-2-(phenylimino)thiazolidin-4-one |
| 04_B_A | (2Z,5Z)-5-((1H-benzo[d]imidazol-5-yl)methylene)-2-(4-fluorophenylimino)-3-p-tolylthiazolidin-4-one |
| 04_N_G | (2Z,5Z)-5-((1H-benzo[d]imidazol-5-yl)methylene)-3-butyl-2-(phenylimino)thiazolidin-4-one |
| 03_C_K | (2Z,5Z)-5-((1H-indol-5-yl)methylene)-2-(benzylimino)-3-(3-phenylpropyl)thiazolidin-4-one |
| 03_N_K | (2Z,5Z)-5-((1H-indol-5-yl)methylene)-2-(phenylimino)-3-(3-phenylpropyl)thiazolidin-4-one |
| 04_B_X | (2Z,5Z)-5-((1H-benzo[d]imidazol-5-yl)methylene)-2-(4-fluorophenylimino)-3-isobutylthiazolidin-4-one |
| 03_N_C | (2Z,5Z)-5-((1H-benzo[d]imidazol-5-yl)methylene)-3-benzyl-2-(phenylimino)thiazolidin-4-one |
| 32_B_A | (2Z,5Z)-5-((1H-benzo[d]imidazol-5-yl)methylene)-2-(4-fluorophenylimino)-3-p-tolylthiazolidin-4-one |
| 03_N_G | (2Z,5Z)-5-((1H-benzo[d]imidazol-5-yl)methylene)-3-butyl-2-(phenylimino)thiazolidin-4- |
| 03_C_O | (2Z,5Z)-5-((1H-indol-5-yl)methylene)-2-(benzylimino)-3-phenethylthiazolidin-4-one |
| 04_N_K | (2Z,5Z)-5-((1H-benzo[d]imidazol-5-yl)methylene)-2-(phenylimino)-3-(3-phenylpropyl)thiazolidin-4-one |
| 03 | (2Z,5Z)-5-((1H-indol-5-yl)methylene)-3-phenyl-2-(phenylimino)thiazolidin-4-one |
| 03_B_A | (2Z,5Z)-5-((1H-indol-5-yl)methylene)-2-(4-fluorophenylimino)-3-p-tolylthiazolidin-4-one |
| 04_C_B | (2Z,5Z)-5-((1H-benzo[d]imidazol-5-yl)methylene)-2-(benzylimino)-3-(4-fluorophenyl)thiazolidin-4-one |
| 04_S_N | (2Z,5Z)-2-((pyridin-3-yl)methylimino)-5-((1H-benzo[d]imidazol-5-yl)methylene)-3-phenylthiazolidin-4-one |
| 03_N_M | (2Z,5Z)-5-((1H-indol-5-yl)methylene)-3-((furan-2-yl)methyl)-2-(phenylimino)thiazolidin-4-one |
| 32_B_X | (2Z,5Z)-2-(4-fluorophenylimino)-5-((benzo[d]thiazol-6-yl)methylene)-3-isobutylthiazolidin-4-one |
| 04_P_N | (2Z,5Z)-5-((1H-benzo[d]imidazol-5-yl)methylene)-2-(4-fluorobenzylimino)-3-phenylthiazolidin-4-one |

-continued

| ETI-T-compound | IUPAC name |
|---|---|
| 04_C_G | (2Z,5Z)-5-((1H-benzo[d]imidazol-5-yl)methylene)-2-(benzylimino)-3-butylthiazolidin-4-one |
| 03_F_N | (2Z,5Z)-5-((1H-indol-5-yl)methylene)-2-(4-methoxyphenylimino)-3-phenylthiazolidin-4-one |
| 04_C_O | (2Z,5Z)-5-((1H-benzo[d]imidazol-5-yl)methylene)-2-(benzylimino)-3-phenethylthiazolidin-4-one |
| 04_C_K | (2Z,5Z)-5-((1H-benzo[d]imidazol-5-yl)methylene)-2-(benzylimino)-3-(3-phenylpropyl)thiazolidin-4-one |
| 04_U_N | (2Z,5Z)-5-((1H-benzo[d]imidazol-5-yl)methylene)-2-(phenethylimino)-3-phenylthiazolidin-4-one |
| 04_D_N | (2Z,5Z)-5-((1H-benzo[d]imidazol-5-Amethylene)-2-(5-methylpyridin-2-ylimino)-3-phenylthiazolidin-4-one |
| 28_B_I | (2Z,5Z)-2-(4-fluorophenylimino)-3-cyclohexyl-5-((1-methyl-1H-indazol-5-yl)methylene)thiazolidin-4-one |
| 04_N_M | (2Z,5Z)-5-((1H-benzo[d]imidazol-5-yl)methylene)-3-((furan-2-yl)methyl)-2-(phenylimino)thiazolidin-4-one |
| 04_C_N | (2Z,5Z)-5-((1H-benzo[d]imidazol-5-yl)methylene)-2-(benzylimino)-3-phenylthiazolidin-4-one |
| 04_C_C | (2Z,5Z)-5-((1H-benzo[d]imidazol-5-yl)methylene)-3-benzyl-2-(benzylimino)thiazolidin-4-one |
| 04_N_C | (2Z,5Z)-5-((1H-benzo[d]imidazol-5-yl)methylene)-3-benzyl-2-(phenylimino)thiazolidin-4-one |
| 09 | (2Z,5Z)-5-((1H-indol-6-yl)methylene)-3-phenyl-2-(phenylimino)thiazolidin-4-one |
| 03_C_B | (2Z,5Z)-5-((1H-indol-5-yl)methylene)-2-(benzylimino)-3-(4-fluorophenyl)thiazolidin-4-one |
| 03_D_N | (2Z,5Z)-5-((1H-indol-5-yl)methylene)-2-(5-methylpyridin-2-ylimino)-3-phenylthiazolidin-4-one |
| 04_C_N | (2Z,5Z)-5-((1H-benzo[d]imidazol-5-yl)methylene)-2-(benzylimino)-3-phenylthiazolidin-4-one |
| 28_B_A | (2Z,5Z)-2-(4-fluorophenylimino)-5-((l-methyl-1H-indazol-5-yl)methylene)-3-p-tolylthiazolidin-4-one |
| 26 | (2Z,5Z)-5-((benzofuran-5-yl)methylene)-3-phenyl-2-(phenylimino)thiazolidin-4-one |
| 28_A_A | (2Z,5Z)-2-(4-fluorophenylimino)-5-((l-methyl-1H-indazol-5-yl)methylene)-3-p-tolylthiazolidin-4-one |
| 30 | (2Z,5Z)-5-((benzo[b]thiophen-5-yl)methylene)-3-phenyl-2-(phenylimino)thiazolidin-4-one |
| 03_C_G | (2Z,5Z)-5-((1H-indol-5-yl)methylene)-2-(benzylimino)-3-butylthiazolidin-4-one |
| 20 | 6-((13Z)-((Z)-4-oxo-3-phenyl-2-(phenylimino)thiazolidin-5-ylidene)methyl)benzo[d]oxazol-2(3H)-one |
| 11 | (2Z,5Z)-3-phenyl-2-(phenylimino)-5-((quinoxalin-6-yl)methylene)thiazolidin-4-one |
| 04_R_N | (2Z,5Z)-5-((1H-benzo[d]imidazol-5-yl)methylene)-2-(4-tert-butylbenzylimino)-3-phenylthiazolidin-4-one |
| 31 | (2Z,5Z)-5-((benzo[d]thiazol-5-yl)methylene)-3-phenyl-2-(phenylimino)thiazolidin-4-one |
| 03_E_N | (2Z,5Z)-5-((1H-indol-5-yl)methylene)-2-(methylimino)-3-phenylthiazolidin-4-one |
| 03_A_V | (2Z,5Z)-5-((1H-indol-5-yl)methylene)-2-(p-tolylimino)-3-dodecylthiazolidin-4-one |
| 16 | (2Z,5Z)-5-((2-methylbenzo[d]thiazol-6-yl)methylene)-3-phenyl-2-(phenylimino)thiazolidin-4-one |
| 17 | 3-methyl-6-((18Z)-((Z)-4-oxo-3-phenyl-2-(phenylimino)thiazolidin-5-ylidene)methyl)benzo[d]thiazol-2(3H)-one |
| 21 | 5-((18Z)-((Z)-4-oxo-3-phenyl-2-(phenylimino)thiazolidin-5-ylidene)methyl)-1H-benzo[d]imidazol-2(3H)-one |
| 03_N_F | (2Z,5Z)-5-((1H-indol-5-yl)methylene)-3-(4-methoxyphenyl)-2-(phenylimino)thiazolidin-4-one |
| 03_Q_N | (2Z,5Z)-5-((1H-indol-5-yl)methylene)-2-(4-methoxybenzylimino)-3-phenylthiazolidin-4-one |
| 03_R_N | (2Z,5Z)-5-((1H-indol-5-yl)methylene)-2-(4-tert-butylbenzylimino)-3-phenylthiazolidin-4- |
| 04_E_N | (2Z,5Z)-5-((1H-benzo[d]imidazol-5-yl)methylene)-2-(methylimino)-3-phenylthiazolidin-4-one |
| 04_N_F | (2Z,5Z)-5-((1H-benzo[d]imidazol-5-yl)methylene)-3-(4-methoxyphenyl)-2-(phenylimino)thiazolidin-4-one |
| 04_T_N | (2Z,5Z)-5-((1H-benzo[d]imidazol-5-yl)methylene)-2-(2-chlorobenzylimino)-3-phenylthiazolidin-4-one |

According to the second aspect the invention relates to a compound characterized by a general formula 1

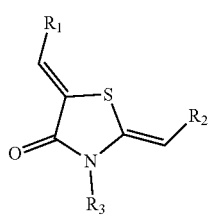

(formula 1)

wherein
$R^2$ is selected from
- a substituted or unsubstituted alkyl, in particular a substituted or unsubstituted $C_1$-$C_{12}$ alkyl,
- a substituted or unsubstituted alkoxy, in particular a substituted or unsubstituted $C_1$-$C_{12}$ alkoxy,
- a substituted or unsubstituted alkenyl, in particular a substituted or unsubstituted $C_2$-$C_{12}$ alkenyl,
- a substituted or unsubstituted alkynyl, in particular a substituted or unsubstituted $C_2$-$C_{12}$ alkynyl,
- a substituted or unsubstituted cycloalkyl, in particular a substituted or unsubstituted $C_3$-$C_{10}$ cycloalkyl,
- a substituted or unsubstituted aryl, in particular a substituted or unsubstituted $C_{6-10}$ aryl,
- a substituted or unsubstituted heterocycle, in particular a substituted or unsubstituted $C_3$-$C_{10}$ heterocycle, or
- a substituted or unsubstituted heteroaryl, in particular a substituted or unsubstituted $C_5$-$C_{10}$ heteroaryl, and each of $R^1$ and $R^3$ are selected independently from each other from
- a substituted or unsubstituted alkyl, in particular a substituted or unsubstituted $C_1$-$C_{12}$ alkyl,
- a substituted or unsubstituted alkoxy, in particular a substituted or unsubstituted $C_1$-$C_{12}$ alkoxy,
- a substituted or unsubstituted alkenyl, in particular a substituted or unsubstituted $C_2$-$C_{12}$ alkenyl,
- a substituted or unsubstituted alkynyl, in particular a substituted or unsubstituted $C_2$-$C_{12}$ alkynyl,
- a substituted or unsubstituted cycloalkyl, in particular a substituted or unsubstituted $C_3$-$C_{10}$ cycloalkyl,
- a substituted or unsubstituted aryl, in particular a substituted or unsubstituted $C_6$-$C_{10}$ aryl,
- a substituted or unsubstituted heterocycle, in particular a substituted or unsubstituted $C_3$-$C_{10}$ heterocycle, or
- a substituted or unsubstituted heteroaryl, in particular a substituted or unsubstituted $C_5$-$C_{10}$ heteroaryl.

In some embodiments, $R^2$ is selected from a moiety described in the embodiments of the first aspect of the invention concerning the substituent $R^2$. Reference made to the detailed description above, in order to avoid repetition.

In some embodiments, $R^1$ is selected from a moiety described in the embodiments of the first aspect of the invention concerning the substituent $R^1$. Reference made to the detailed description above, in order to avoid repetition.

In some embodiments, $R^3$ is selected from a moiety described in the embodiments of the first aspect of the invention concerning the substituent $R^3$. Reference made to the detailed description above, in order to avoid repetition.

Any embodiment described for $R^1$ or $R^3$ according to the second aspect of the invention may be combined with any embodiment described for $R^2$ according to the second aspect of the invention.

According to the third aspect the invention relates to a compound characterized by a general formula 1

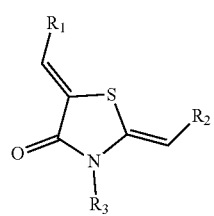

(formula 1)

wherein
$R^3$ is selected from
- a substituted or unsubstituted alkyl, in particular a substituted or unsubstituted $C_1$-$C_{12}$ alkyl,
- a substituted or unsubstituted alkoxy, in particular a substituted or unsubstituted $C_1$-$C_{12}$ alkoxy,
- a substituted or unsubstituted alkenyl, in particular a substituted or unsubstituted $C_2$-$C_{12}$ alkenyl,
- a substituted or unsubstituted alkynyl, in particular a substituted or unsubstituted $C_2$-$C_{12}$ alkynyl,
- a substituted or unsubstituted cycloalkyl, in particular a substituted or unsubstituted $C_3$-$C_{10}$ cycloalkyl,
- a substituted or unsubstituted aryl, in particular a substituted or unsubstituted $C_6$-$C_{10}$ aryl,
- a substituted or unsubstituted heterocycle, in particular a substituted or unsubstituted $C_3$-$C_{10}$ heterocycle, or
- a substituted or unsubstituted heteroaryl, in particular a substituted or unsubstituted $C_5$-$C_{10}$ heteroaryl, and each of $R^1$ and $R^2$ are selected independently from each other from
- a substituted or unsubstituted alkyl, in particular a substituted or unsubstituted $C_1$-$C_{12}$ alkyl,
- a substituted or unsubstituted alkoxy, in particular a substituted or unsubstituted $C_1$-$C_{12}$ alkoxy,
- a substituted or unsubstituted alkenyl, in particular a substituted or unsubstituted $C_2$-$C_{12}$ alkenyl,
- a substituted or unsubstituted alkynyl, in particular a substituted or unsubstituted $C_2$-$C_{12}$ alkynyl,
- a substituted or unsubstituted cycloalkyl, in particular a substituted or unsubstituted $C_3$-$C_{10}$ cycloalkyl,
- a substituted or unsubstituted aryl, in particular a substituted or unsubstituted $C_6$-$C_{10}$ aryl,
- a substituted or unsubstituted heterocycle, in particular a substituted or unsubstituted $C_3$-$C_{10}$ heterocycle, or
- a substituted or unsubstituted heteroaryl, in particular a substituted or unsubstituted $C_5$-$C_{10}$ heteroaryl.

In some embodiments, $R^3$ is selected from a moiety described in the embodiments of the first aspect of the invention concerning the substituent $R^3$. Reference made to the detailed description above, in order to avoid repetition.

In some embodiments, $R^1$ is selected from a moiety described in the embodiments of the first aspect of the invention concerning the substituent $R^1$. Reference made to the detailed description above, in order to avoid repetition.

In some embodiments, $R^2$ is selected from a moiety described in the embodiments of the first aspect of the invention concerning the substituent $R^2$. Reference made to the detailed description above, in order to avoid repetition.

Any embodiment described for $R^1$ or $R^2$ according to the third aspect of the invention may be combined with any embodiment described for $R^3$ according to the third aspect of the invention.

According to the fourth aspect the invention relates to a compound comprising the following general formula (1)

(formula 1)

$$\begin{array}{c} R_1 \\ \diagup \\ \text{structure with S, N-R}_3, \text{C=O, R}_2 \end{array}$$

wherein
R$^1$ is selected from
- a substituted or unsubstituted alkyl, in particular a substituted or unsubstituted $C_1$-$C_{12}$ alkyl,
- a substituted or unsubstituted alkoxy, in particular a substituted or unsubstituted $C_1$-$C_{12}$ alkoxy,
- a substituted or unsubstituted alkenyl, in particular a substituted or unsubstituted $C_2$-$C_{12}$ alkenyl,
- a substituted or unsubstituted alkynyl, in particular a substituted or unsubstituted $C_2$-$C_{12}$ alkynyl,
- a substituted or unsubstituted cycloalkyl, in particular a substituted or unsubstituted $C_3$-$C_{10}$ cycloalkyl,
- a substituted or unsubstituted aryl, in particular a substituted or unsubstituted $C_6$-$C_{10}$ aryl, and each of R$^2$ and R$^3$ are selected independently from each other from
- a substituted or unsubstituted alkyl, in particular a substituted or unsubstituted $C_1$-$C_{12}$ alkyl,
- a substituted or unsubstituted alkoxy, in particular a substituted or unsubstituted $C_1$-$C_{12}$ alkoxy,
- a substituted or unsubstituted alkenyl, in particular a substituted or unsubstituted $C_2$-$C_{12}$ alkenyl,
- a substituted or unsubstituted alkynyl, in particular a substituted or unsubstituted $C_2$-$C_{12}$ alkynyl,
- a substituted or unsubstituted cycloalkyl, in particular a substituted or unsubstituted $C_3$-$C_{10}$ cycloalkyl,
- a substituted or unsubstituted aryl, in particular a substituted or unsubstituted $C_6$-$C_{10}$ aryl,
- a substituted or unsubstituted heterocycle, in particular a substituted or unsubstituted $C_3$-$C_{10}$ heterocycle, or
- a substituted or unsubstituted heteroaryl, in particular a substituted or unsubstituted $C_5$-$C_{10}$ heteroaryl.

In some embodiments, R$^1$ is selected from
- a substituted or unsubstituted alkyl, in particular a substituted or unsubstituted $C_1$-$C_{12}$ alkyl,
- a substituted or unsubstituted alkoxy, in particular a substituted or unsubstituted $C_1$-$C_{12}$ alkoxy,
- a substituted or unsubstituted alkenyl, in particular a substituted or unsubstituted $C_{12}$-$C_{12}$ alkenyl,
- a substituted or unsubstituted alkynyl, in particular a substituted or unsubstituted $C_2$-$C_{12}$ alkynyl,
- a substituted or unsubstituted aryl, in particular a substituted or unsubstituted $C_6$-$C_{10}$ aryl.

In some embodiments, R$^1$ is selected from
- a substituted alkyl, alkenyl or alkynyl, wherein the substituted alkyl, alkenyl or alkynyl comprises the formula -M-Ar, with M being
- an alkyl, in particular a $C_1$-$C_{12}$ alkyl, more particularly a $C_1$-$C_4$ alkyl,
- an alkenyl, in particular a $C_2$-$C_{12}$ alkenyl, more particularly a $C_2$-$C_4$ alkenyl,
- an alkynyl, in particular a $C_2$-$C_{12}$ alkynyl, more particularly a $C_2$-$C_4$ alkynyl, and Ar being a substituted or unsubstituted $C_5$-$C_6$- aryl or a substituted or unsubstituted $C_5$-$C_6$- heteroaryl, or a substituted or unsubstituted $C_6$- aryl, wherein in particular the substituted $C_6$- aryl comprises at least one substituent $Z^{10}$.

In some embodiments, R$^1$ is selected from
- a substituted alkyl, alkenyl or alkynyl, wherein the substituted alkyl, alkenyl or alkynyl comprises the formula 6a (formula 6a)

or
- a substituted or unsubstituted $C_6$- aryl, wherein the substituted $C_6$ aryl comprises the formula 6b (formula 6b)

with M being
- an alkyl, in particular a $C_1$-$C_{12}$ alkyl, more particularly a $C_1$-$C_4$ alkyl,
- an alkenyl, in particular a $C_2$-$C_{12}$ alkenyl, more particularly a $C_2$-$C_4$ alkenyl,
- an alkynyl, in particular a $C_2$-$C_{12}$ alkynyl, more particularly a $C_2$-$C_4$ alkynyl, and l of $Z^{10}_l$ is 0, 1, 2, 3, 4 or 5, in particular 0, 1, 2 or 3, more particularly 0 or 1, and each $Z^{10}$ independently from any other $Z^{10}$ is selected from —F, —Cl, —Br, —I, CN, —R$^e$, —OR$^e$, —(CH$_2$)$_r$OR$^e$, —SR$^e$, —(CH$_2$)$_r$SR$^e$ or —NR$^e_2$, with each R$^e$ being selected independently from each other from H, a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl, or a substituted or unsubstituted $C_2$-$C_{12}$ alkynyl, in particular $C_2$-$C_4$ alkynyl, with r being 1, 2, 3 or 4, in particular r is 1.

In some embodiments, R$^1$ is selected from
- a substituted alkyl, wherein the substituted alkyl comprises the formula 6a (formula 6a)

or
- a substituted or unsubstituted $C_6$- aryl, wherein the $C_6$ aryl comprises the formula 6b

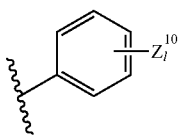

(formula 6b)

with M being
an alkyl, in particular a $C_1$-$C_{12}$ alkyl, more particularly a $C_1$-$C_4$ alkyl, and
I of $Z^{10}{}_I$ is 0, 1, 2, 3, 4 or 5, in particular 0, 1, 2 or 3, more particularly 0 or 1, and
each $Z^{10}$ independently from any other $Z^{10}$ is selected from —F, —Cl, —Br, —I, CN, —$R^e$, —$OR^e$, —$(CH_2)_rOR^e$, —$SR^e$, —$(CH_2)_rSR^e$ or —$NR^e{}_2$, with each $R^e$ being selected independently from each other from H, a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl, or a substituted or unsubstituted $C_2$-$C_{12}$ alkynyl, in particular $C_2$-$C_4$ alkynyl, with r being 1, 2, 3 or 4, in particular r is 1.

In some embodiments, $R^1$ is selected from
a substituted or unsubstituted $C_6$- aryl, wherein the $C_6$ aryl comprises the formula 6b

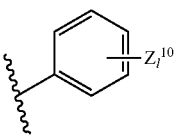

(formula 6b)

with I of $Z^{10}{}_I$ being 0, 1, 2, 3, 4 or 5, in particular 0, 1, 2 or 3, more particularly 0 or 1, and
each $Z^{10}$ independently from any other $Z^{10}$ is selected from —F, —Cl, —Br, —I, CN, —$R^e$, —$OR^e$, —$(CH_2)_rOR^e$, —$SR^e$, —$(CH_2)_rSR^e$ or —$NR^e{}_2$, with each $R^e$ being selected independently from each other from H, a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl, or a substituted or unsubstituted $C_2$-$C_{12}$ alkynyl, in particular $C_2$-$C_4$ alkynyl, with r being 1, 2, 3 or 4, in particular r is 1.

In some embodiments, $R^1$ is selected from
a substituted or unsubstituted $C_6$- aryl, wherein the substituted $C_6$ aryl comprises the formula 6b

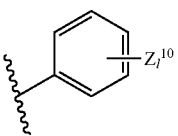

(formula 6b)

I of $Z^{10}{}_I$ is 1, 2, 3, 4 or 5, in particular 1, 2 or 3, more particularly 1, and
each $Z^{10}$ independently from any other $Z^{10}$ is selected from —F, —Cl, —Br, —I, CN, —$R^e$, —$OR^e$, —$(CH_2)_rOR^e$, —$SR^e$, —$(CH_2)_rSR^e$ or —$NR^e{}_2$, with each $R^e$ being selected independently from each other from H, a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl, or a substituted or unsubstituted $C_2$-$C_{12}$ alkynyl, in particular $C_2$-$C_4$ alkynyl, with r being 1, 2, 3 or 4, in particular r is 1, wherein at least one $Z^{10}$ is —$(CH_2)_rOR^e$, in particular in position 3.

In some embodiments, I of $Z^{10}{}_I$ is 0, 1, 2, 3, 4 or 5, in particular 0, 1, 2 or 3, more particularly 0 or 1, and each $Z^{10}$ is selected independently from any other $Z^{10}$ from —F, —Cl, —Br, —I, CN, —$R^e$, —$SR^e$, —$CH_2SR^e$, —$OR^e$, $CH_2OR^e$ or —$NR^e{}_2$, in particular from —F, —Cl, CN, —$R^e$, —$OR^e$, —$CH_2OR^e$ or —$NR^e{}_2$, more particularly from CN, —$OR^e$ or $CH_2OR^e$, with each $R^e$ being selected independently from each other from H, a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl, or a substituted or unsubstituted $C_2$-$C_{12}$ alkynyl, in particular $C_2$-$C_4$ alkynyl.

In some embodiments, I of $Z^{10}{}_I$ is 0, 1, 2, 3, 4 or 5, in particular 0, 1, 2 or 3, more particularly 0 or 1, and each $Z^3$ is selected independently from any other $Z^3$ from —F, —Cl, —Br, —I, CN, —$OR^e$ or —$CH_2OR^e$, in particular from $R^e$, with $R^e$ being selected from a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl or a substituted or unsubstituted $C_2$-$C_{12}$ alkynyl, in particular $C_2$-$C_4$ alkynyl.

In some embodiments, I of $Z^{10}{}_I$ is 1, 2, 3, 4 or 5, in particular 1, 2 or 3, more particularly 1, and each $Z^{10}$ is selected independently from any other $Z^{10}$ from —F, —Cl, —Br, —I, CN, —$R^e$, —$SR^e$, —$CH_2SR^e$, —$OR^e$, $CH_2OR^e$ or —$NR^e{}_2$, in particular from —F, —Cl, CN, —$R^e$, —$OR^e$, —$CH_2OR^e$ or —$NR^e{}_2$, more particularly from CN, —$OR^e$ or $CH_2OR^e$, with each $R^e$ being selected independently from each other from H, a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl, or a substituted or unsubstituted $C_2$-$C_{12}$ alkynyl, in particular $C_2$-$C_4$ alkynyl.

In some embodiments, I of $Z^{10}{}_I$ is 1, 2, 3, 4 or 5, in particular 1, 2 or 3, more particularly 1, and each $Z^3$ is selected independently from any other $Z^3$ from —F, —Cl, —Br, —I, CN, —$OR^e$ or —$CH_2OR^e$, in particular from $R^e$, with $R^e$ being selected from a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl or a substituted or unsubstituted $C_2$-$C_{12}$ alkynyl, in particular $C_2$-$C_4$ alkynyl.

In some embodiments, I of $Z^{10}{}_I$ is 1 or 2, in particular 1.

In some embodiments, I of $Z^{10}{}_I$ the at least one $Z^{10}$ is —$(CH_2)_rOR^e$, in particular in position 3, with $R^e$ being H or $CH_3$, with r being selected from 1, 2, 3, in particular with r being 1.

In some embodiments, I of $Z^{10}{}_I$ is 0, 1 or 2, in particular 0 or 1.

In some embodiments, $R^1$ is selected from.

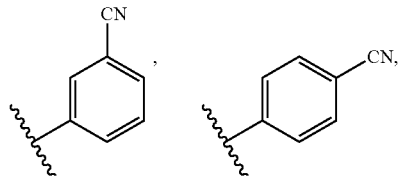

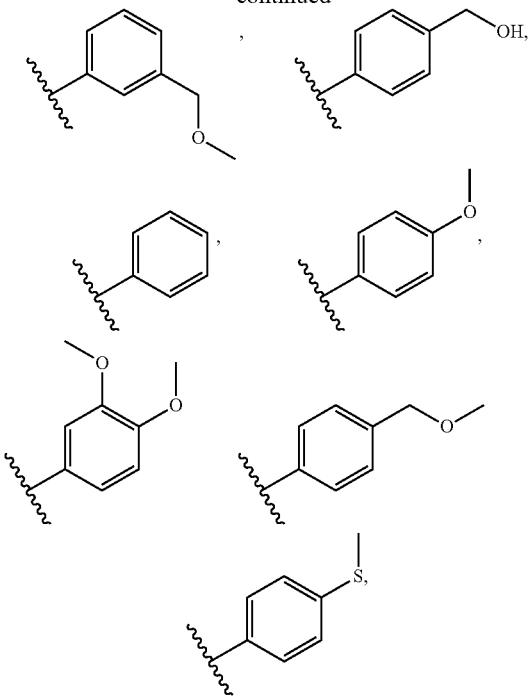

or derivatives thereof.
In some embodiments, R¹ is selected from.

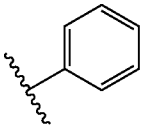

or derivatives thereof.

In some embodiments, R¹ is selected from

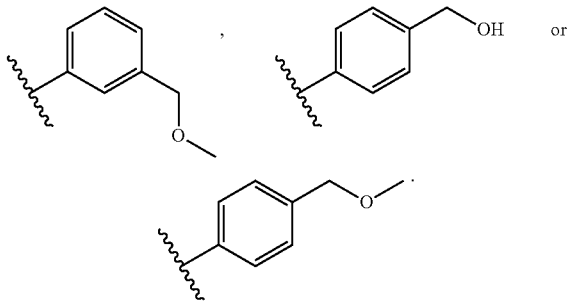

In some embodiments, R² is selected from a moiety described in the embodiments of the first aspect of the invention concerning the substituent R². Reference made to the detailed description above, in order to avoid repetition.

In some embodiments, R³ is selected from a moiety described in the embodiments of the first aspect of the invention concerning the substituent R³. Reference made to the detailed description above, in order to avoid repetition.

Any embodiment described for R² or R³ according to the fourth aspect of the invention may be combined with any embodiment described for R¹ according to the fourth aspect of the invention.

Particular embodiments are given below:

| ETI-T-compound | IUPAC name |
|---|---|
| 22_K_N | (2Z,5Z)-2-(3-phenylpropylimino)-5-(4-(hydroxymethyl)benzylidene)-3-phenylthiazolidin-4-one |
| 22_A_N | (2Z,5Z)-5-(4-(hydroxymethyl)benzylidene)-2-(p-tolylimino)-3-phenylthiazolidin-4-one |
| 22_B_X | (2Z,5Z)-5-(4-(hydroxymethyl)benzylidene)-2-(4-fluorophenylimino)-3-isobutylthiazolidin-4-one |
| 22_F_N | (2Z,5Z)-5-(4-(hydroxymethyl)benzylidene)-2-(4-methoxyphenylimino)-3-phenylthiazolidin-4-one |
| 22_A_X | (2Z,5Z)-5-(4-(hydroxymethyl)benzylidene)-2-(p-tolylimino)-3-isobutylthiazolidin-4- |
| 22_A_A | (2Z,5Z)-5-(4-(hydroxymethyl)benzylidene)-2-(p-tolylimino)-3-p-tolylthiazolidin-4-one |
| 15_Q_N | (2Z,5Z)-5-(3-(methoxymethyl)benzylidene)-2-(4-methoxybenzylimino)-3-phenylthiazolidin-4-one |
| 22_B_A | (2Z,5Z)-5-(4-(hydroxymethyl)benzylidene)-2-(4-fluorophenylimino)-3-p-tolylthiazolidin-4-one |
| 22_P_N | (2Z,5Z)-5-(4-(hydroxymethyl)benzylidene)-2-(4-fluorobenzylimino)-3-phenylthiazolidin-4-one |
| 22_C_F | (2Z,5Z)-5-(4-(hydroxymethyl)benzylidene)-2-(benzylimino)-3-(4-methoxyphenyl)thiazolidin-4-one |
| 22_N_C | (2Z,5Z)-5-(4-(hydroxymethyl)benzylidene)-3-benzyl-2-(phenylimino)thiazolidin-4-one |
| 15_C_K | (2Z,5Z)-5-(3-(methoxymethyl)benzylidene)-2-(benzylimino)-3-(3-phenylpropyl)thiazolidin-4-one |
| 22_Q_N | (2Z,5Z)-5-(4-(hydroxymethyl)benzylidene)-2-(4-methoxybenzylimino)-3-phenylthiazolidin-4-one |
| 22 | (2Z,5Z)-5-(4-(hydroxymethyl)benzylidene)-3-phenyl-2-(phenylimino)thiazolidin-4-one |

| ETI-T-compound | IUPAC name |
| --- | --- |
| 22_U_N | (2Z,5Z)-5-(4-(hydroxymethyl)benzylidene)-2-(phenethylimino)-3-phenylthiazolidin-4-one |
| 22_N_K | (2Z,5Z)-5-(4-(hydroxymethyl)benzylidene)-2-(phenylimino)-3-(3-phenylpropyl)thiazolidin-4- |
| 15 | (2Z,5Z)-5-(3-(methoxymethyl)benzylidene)-3-phenyl-2-(phenylimino)thiazolidin-4-one |
| 22_N_G | (2Z,5Z)-5-(4-(hydroxymethyl)benzylidene)-3-butyl-2-(phenylimino)thiazolidin-4-one |
| 22_C_O | (2Z,5Z)-5-(4-(hydroxymethyl)benzylidene)-2-(benzylimino)-3-phenethylthiazolidin-4- |
| 22_C_G | (2Z,5Z)-5-(4-(hydroxymethyl)benzylidene)-2-(benzylimino)-3-butylthiazolidin-4-one |
| 22_N_M | (2Z,5Z)-5-(4-(hydroxymethyl)benzylidene)-3-((furan-2-yl)methyl)-2-(phenylimino)thiazolidin-4-one |
| 22_C_K | (2Z,5Z)-5-(4-(hydroxymethyl)benzylidene)-2-(benzylimino)-3-(3-phenylpropyl)thiazolidin-4- |
| 22_D_N | (2Z,5Z)-5-(4-(hydroxymethyl)benzylidene)-2-(5-methylpyridin-2-ylimino)-3-phenylthiazolidin-4-one |
| 15_C_O | (2Z,5Z)-5-(4-(hydroxymethyl)benzylidene)-2-(benzylimino)-3-phenethylthiazolidin-4-one |
| 22_C_N | (2Z,5Z)-5-(4-(hydroxymethyl)benzylidene)-2-(benzylimino)-3-phenylthiazolidin-4-one |
| 15_C_N | (2Z,5Z)-5-(3-(methoxymethyl)benzylidene)-2-(benzylimino)-3-phenylthiazolidin-4- |
| 22_C_B | (2Z,5Z)-5-(4-(hydroxymethyl)benzylidene)-2-(benzylimino)-3-(4-fluorophenyl)thiazolidin-4-one |
| 15_T_N | (2Z,5Z)-2-(2-chlorobenzylimino)-5-(3-(methoxymethyl)benzylidene)-3-phenylthiazolidin-4-one |
| 22_R_N | (2Z,5Z)-5-(4-(hydroxymethyl)benzylidene)-2-(4-tert-butylbenzylimino)-3-phenylthiazolidin-4-one |
| 22_C_C | (2Z,5Z)-5-(4-(hydroxymethyl)benzylidene)-3-benzyl-2-(benzylimino)thiazolidin-4-one |
| 23_A_V | (2Z,5Z)-5-(4-(hydroxymethyl)benzylidene)-2-(4-fluorophenylimino)-3-dodecylthiazolidin-4-one |
| 22_B_V | (2Z,5Z)-5-(4-(hydroxymethyl)benzylidene)-2-(4-fluorophenylimino)-3-dodecylthiazolidin-4-one |
| 15_U_N | (2Z,5Z)-5-(3-(methoxymethyl)benzylidene)-2-(phenethylimino)-3-phenylthiazolidin-4-one |
| 34 | (2Z,5Z)-5-(4-(methoxymethyl)benzylidene)-3-phenyl-2-(phenylimino)thiazolidin-4-one |
| 04_A_V | (2Z,5Z)-5-(4-(hydroxymethyl)benzylidene)-2-(p-tolylimino)-3-dodecylthiazolidin-4-one |
| 15_R_N | (2Z,5Z)-5-(3-(methoxymethyl)benzylidene)-2-(4-tert-butylbenzylimino)-3-phenylthiazolidin-4-one |
| 22_A_V | (2Z,5Z)-5-(4-(hydroxymethyl)benzylidene)-2-(p-tolylimino)-3-dodecylthiazolidin-4-one |
| 22_E_N | (2Z,5Z)-5-(4-(hydroxymethyl)benzylidene)-2-(methylimino)-3-phenylthiazolidin-4-one |
| 22_N_F | (2Z,5Z)-5-(4-(hydroxymethyl)benzylidene)-3-(4-methoxyphenyl)-2-(phenylimino)thiazolidin-4-one |
| 22_T_N | (2Z,5Z)-2-(2-chlorobenzylimino)-5-(4-(hydroxymethyl)benzylidene)-3-phenylthiazolidin-4-one |

In some embodiments of a first sub aspect of the fourth aspect of the invention $R^1$ is selected from

- a substituted or unsubstituted alkyl, in particular a substituted or unsubstituted $C_1$-$C_{12}$ alkyl,
- a substituted or unsubstituted alkoxy, in particular a substituted or unsubstituted $C_1$-$C_{12}$ alkoxy,
- a substituted or unsubstituted alkenyl, in particular a substituted or unsubstituted $C_1$-$C_{12}$ alkenyl,
- a substituted or unsubstituted alkynyl, in particular a substituted or unsubstituted $C_1$-$C_{12}$ alkynyl,
- a substituted or unsubstituted cycloalkyl, in particular a substituted or unsubstituted $C_3$-$C_{10}$ cycloalkyl,
- a substituted or unsubstituted aryl, in particular a substituted or unsubstituted $C_6$-$C_{10}$ aryl, and each of $R^2$ and $R^3$ are selected independently from each other from

- a substituted or unsubstituted alkyl, in particular a substituted or unsubstituted $C_1$-$C_{12}$ alkyl,
- a substituted or unsubstituted alkoxy, in particular a substituted or unsubstituted $C_1$-$C_{12}$ alkoxy,
- a substituted or unsubstituted alkenyl, in particular a substituted or unsubstituted $C_1$-$C_{12}$ alkenyl,
- a substituted or unsubstituted alkynyl, in particular a substituted or unsubstituted $C_1$-$C_{12}$ alkynyl,
- a substituted or unsubstituted cycloalkyl, in particular a substituted or unsubstituted $C_3$-$C_{10}$ cycloalkyl,
- a substituted or unsubstituted aryl, in particular a substituted or unsubstituted $C_6$-$C_{10}$ aryl,
- a substituted or unsubstituted saturated heterocycle, in particular a substituted or unsubstituted $C_3$-$C_{10}$ heterocycle, or
- a substituted or unsubstituted heteroaryl, in particular a substituted or unsubstituted $C_5$-$C_{10}$ heteroaryl, wherein at least one of $R_1$, $R_2$ and $R_3$ is selected form,
in case of $R_1$,
from
a substituted alkyl, alkenyl or alkynyl, wherein the substituted alkyl, alkenyl or alkynyl comprises the formula -M-Ar,
  with M being
    an alkyl, in particular a $C_1$-$C_{12}$ alkyl, more particularly a $C_1$-$C_4$ alkyl,
    an alkenyl, in particular a $C_1$-$C_{12}$ alkenyl, more particularly a $C_1$-$C_4$ alkenyl,
    an alkynyl, in particular a $C_1$-$C_{12}$ alkynyl, more particularly a $C_1$-$C_4$ alkynyl, and
  Ar being a $C_6$- aryl, wherein in particular the substituted $C_6$- aryl comprises at least one substituent $Z^{10}$,
in case of $R_2$ from
a substituted alkyl, alkenyl or alkynyl, wherein the substituted alkyl, alkenyl or alkynyl comprises the formula -L-Ar,
  with L being
    an alkyl, in particular a $C_1$-$C_{12}$ alkyl, more particularly a $C_1$-$C_4$ alkyl,
    an alkenyl, in particular a $C_1$-$C_{12}$ alkenyl, more particularly a $C_1$-$C_4$ alkenyl,
    an alkynyl, in particular a $C_1$-$C_{12}$ alkynyl, more particularly a $C_1$-$C_4$ alkynyl, and
  Ar being a substituted or unsubstituted $C_5$-$C_6$- aryl or a substituted or unsubstituted $C_5$-$C_6$- heteroaryl, or
a substituted or unsubstituted $C_6$- aryl or a substituted or unsubstituted $C_5$-$C_6$-heteroaryl, wherein in particular the substituted $C_6$- aryl or the substituted $C_5$-$C_6$-heteroaryl comprises at least one substituent $Z^2$, and
in case of $R_3$ from
a substituted alkyl, alkenyl or alkynyl, wherein the substituted alkyl, alkenyl or alkynyl comprises the formula -D-Ar,
  with D being
    an alkyl, in particular a $C_1$-$C_{12}$ alkyl, more particularly a $C_1$-$C_4$ alkyl,
    an alkenyl, in particular a $C_1$-$C_{12}$ alkenyl, more particularly a $C_1$-$C_4$ alkenyl,
    an alkynyl, in particular a $C_1$-$C_{12}$ alkynyl, more particularly a $C_1$-$C_4$ alkynyl, and
  Ar being a substituted or unsubstituted $C_5$-$C_6$- aryl or a substituted or unsubstituted $C_5$-$C_6$- heteroaryl, or
    a substituted or unsubstituted $C_6$- aryl or a substituted or unsubstituted $C_5$-$C_6$- heteroaryl, wherein in particular the substituted $C_6$- aryl or the substituted $C_5$-$C_6$- heteroaryl comprises at least one substituent $Z^3$ In some embodiments, particularly of the first aspect of the fourth invention, $R^1$ is selected from
a substituted alkyl, alkenyl or alkynyl, wherein the substituted alkyl, alkenyl or alkynyl comprises the formula 6a

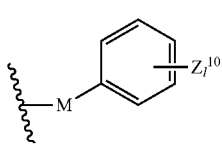

(formula 6a)

or
with M being
  an alkyl, in particular a $C_1$-$C_{12}$ alkyl, more particularly a $C_1$-$C_4$ alkyl,
  an alkenyl, in particular a $C_1$-$C_{12}$ alkenyl, more particularly a $C_1$-$C_4$ alkenyl,
  an alkynyl, in particular a $C_1$-$C_{12}$ alkynyl, more particularly a $C_1$-$C_4$ alkynyl, and
I of $Z^{10}{}_I$ is 0, 1, 2, 3, 4 or 5, in particular 0, 1, 2 or 3, more particularly 0 or 1, and each $Z^{10}$ independently from any other $Z^{10}$ is selected from —F, —Cl, —Br, —I, CN, —$R^e$, —$OR^e$, —$(CH_2)_rOR^e$, —$SR^e$, —$(CH_2)_rSR^e$ or —$NR^e{}_2$, with each $R^e$ being selected independently from each other from H, a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl, or a substituted or unsubstituted $C_2$-$C_{12}$ alkynyl, in particular $C_2$-$C_4$ alkynyl, with r being 1, 2, 3 or 4, in particular r is 1.

In some embodiments, particularly of the first aspect of the fourth invention, $R^1$ is selected from wherein $R^1$ is selected from
a substituted alkyl, wherein the substituted alkyl comprises the formula 6a (formula 6a)

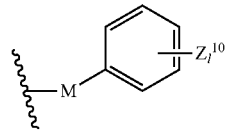

(formula 6a)

with M being
  an alkyl, in particular a $C_1$-$C_{12}$ alkyl, more particularly a $C_1$-$C_4$ alkyl, and
I of $Z^{10}{}_I$ is 0, 1, 2, 3, 4 or 5, in particular 0, 1, 2 or 3, more particularly 0 or 1, and
each $Z^{10}$ independently from any other $Z^{10}$ is selected from —F, —Cl, —Br, —I, CN, —$R^e$, —$OR^e$, —$(CH_2)_rOR^e$, —$SR^e$, —$(CH_2)_rSR^e$ or —$NR^e{}_2$, with each $R^e$ being selected independently from each other from H, a substituted or unsubstituted $C_1$-$C_{12}$ alkyl, in particular $C_1$-$C_4$ alkyl, a substituted or unsubstituted $C_2$-$C_{12}$ alkenyl, in particular $C_2$-$C_4$ alkenyl, or a substituted or unsubstituted $C_2$-$C_{12}$ alkynyl, in particular $C_2$-$C_4$ alkynyl, with r being 1, 2, 3 or 4, in particular r is 1

Concerning further embodiments of I of $Z^{10}{}_I$ and $Z^{10}{}_I$ reference is made to the first aspect of the invention, particularly to the first sub aspect of first aspect of the invention.

Concerning further embodiments of $R^2$ reference is made to the first aspect of the invention, particularly to the second sub aspect of first aspect of the invention.

Concerning further embodiments of o of $Z^2{}_o$ and $Z^2{}_o$ reference is made to the first aspect of the invention, particularly to the first sub aspect of first aspect of the invention.

Concerning further embodiments of $R^3$ reference is made to the first aspect of the invention, particularly to the second sub aspect of first aspect of the invention.

In some embodiments, particularly of the third sub aspect, $R^3$ is selected from
a substituted or unsubstituted $C_1$-$C_4$ alkyl,
a substituted or unsubstituted $C_1$-$C_4$ alkenyl,
a substituted or unsubstituted $C_1$-$C_4$ alkynyl, a substituted or unsubstituted $C_6$ aryl,
a substituted or unsubstituted $C_6$-cycloalkyl or
a substituted or unsubstituted $C_5$-$C_6$- heteroaryl, in particular a substituted or unsubstituted $C_6$-cycloalkyl or a substituted or unsubstituted $C_5$-$C_6$- heteroaryl.

Concerning further more specific embodiments of $R^3$ reference is made to the first aspect of the invention, particularly to the second sub aspect of first aspect of the invention.

Concerning further embodiments of p of $Z^3_p$ and $Z^3_p$ reference is made to the first aspect of the invention, particularly to the first sub aspect of first aspect of the invention.

Particular embodiments are given below:

| ETI-T-compound | IUPAC name |
| --- | --- |
| 23_C_N | (2Z,5Z)-5-benzylidene-2-(benzylimino)-3-phenylthiazolidin-4-one |
| 23_T_N | (2Z,5Z)-2-(2-chlorobenzylimino)-5-benzylidene-3-phenylthiazolidin-4-one |
| 23_Q_N | (2Z,5Z)-2-(4-methoxybenzylimino)-5-benzylidene-3-phenylthiazolidin-4-one |
| 23_C_G | (2Z,5Z)-5-benzylidene-2-(benzylimino)-3-butylthiazolidin-4-one |
| 23_N_K | (2Z,5Z)-5-benzylidene-2-(phenylimino)-3-(3-phenylpropyl)thiazolidin-4-one |
| 23_B_X | (2Z,5Z)-2-(4-fluorophenylimino)-5-benzylidene-3-isobutylthiazolidin-4-one |
| 23_C_O | (2Z,5Z)-5-benzylidene-2-(benzylimino)-3-phenethylthiazolidin-4-one |
| 23_N_M | (2Z,5Z)-5-benzylidene-3-((furan-2-yl)methyl)-2-(phenylimino)thiazolidin-4-one |
| 23_F_N | (2Z,5Z)-2-(4-methoxyphenylimino)-5-benzylidene-3-phenylthiazolidin-4-one |
| 23_A_A | (2Z,5Z)-2-(p-tolylimino)-5-benzylidene-3-p-tolylthiazolidin-4-one |
| 23 | (2Z,5Z)-5-benzylidene-3-phenyl-2-(phenylimino)thiazolidin-4-one |
| 23_K_N | (2Z,5Z)-2-(3-phenylpropylimino)-5-benzylidene-3-phenylthiazolidin-4-one |
| 23_A_N | (2Z,5Z)-2-(p-tolylimino)-5-benzylidene-3-phenylthiazolidin-4-one |
| 23_N_G | (2Z,5Z)-5-benzylidene-3-butyl-2-(phenylimino)thiazolidin-4-one |
| 23_N_C | (2Z,5Z)-3-benzyl-5-benzylidene-2-(phenylimino)thiazolidin-4-one |
| 23_P_N | (2Z,5Z)-2-(4-fluorobenzylimino)-5-benzylidene-3-phenylthiazolidin-4-one |
| 23_C_B | (2Z,5Z)-5-benzylidene-2-(benzylimino)-3-(4-fluorophenyl)thiazolidin-4-one |
| 23_E_N | (2Z,5Z)-5-benzylidene-2-(methylimino)-3-phenylthiazolidin-4-one |
| 23_C_K | (2Z,5Z)-5-benzylidene-2-(benzylimino)-3-(3-phenylpropyl)thiazolidin-4-one |
| 23_B_V | (2Z,5Z)-2-(4-fluorophenylimino)-5-benzylidene-3-dodecylthiazolidin-4-one |
| 23_D_N | (2Z,5Z)-2-(5-methylpyridin-2-ylimino)-5-benzylidene-3-phenylthiazolidin-4-one |
| 23_N_L | (2Z,5Z)-5-benzylidene-3-(4-chlorophenyl)-2-(phenylimino)thiazolidin-4-one |

In some embodiments the compound of the invention according to the first, second, third or fourth aspect of the invention comprises a (2Z,5Z), (2Z,5E), (2E,5Z) or (2E,5E) isomer form, in particular a (2Z,5Z) or (2Z,5E), more particularly a (2Z,5Z) isomer form, characterized by formula 1a

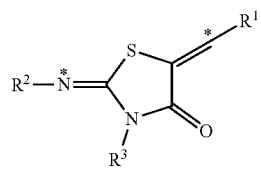

(formula 1a)

with the isomer center being indicated by the asterix (*), with $R^1$, $R^2$ and $R^3$ having the same meaning as defined previously, wherein the compound of the invention comprises the before mentioned isomers in an essentially pure form, with $R^1$, $R^2$ and $R^3$ having the same meaning as defined previously.

As used herein the term "essentially pure" refers to a purity of >90%, in particular of >95%.

In some embodiments the compound of the invention comprises a mixture of the (2Z,5Z), (2Z,5E), (2E,5Z) or (2E,5E) isomer forms, in particular a mixture of (2Z,5Z) and (2Z,5E). characterized by formula 1a as depicted above.

The following formulas show the respective configuration:

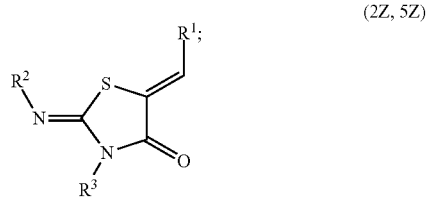

(2Z, 5Z)

(2Z, 5E)

-continued
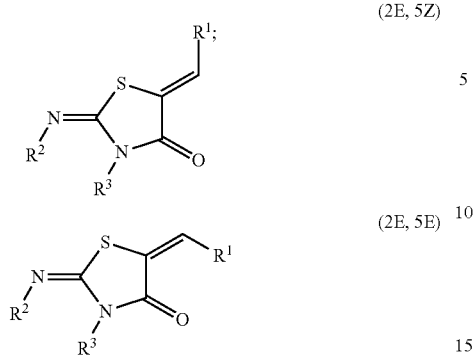
with R¹, R² and R³ having the same meaning as defined previously.
Particular embodiments of the invention are:
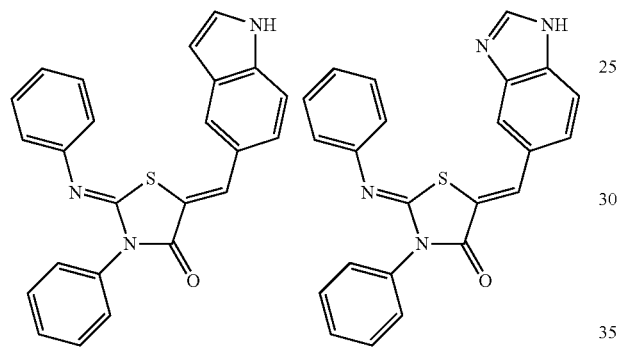
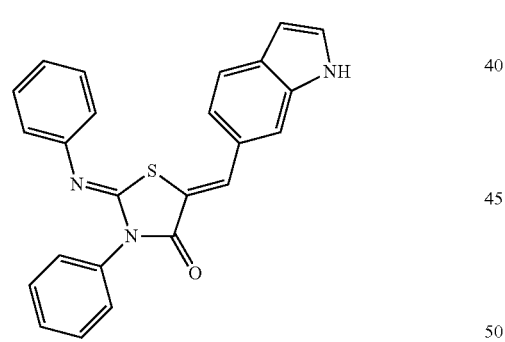
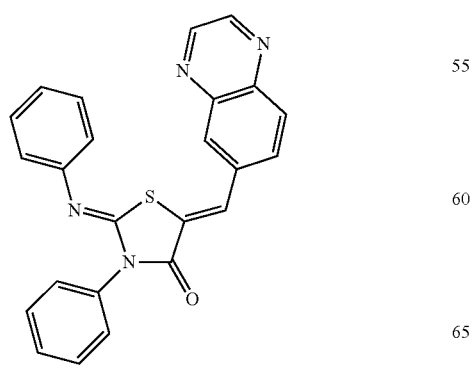
-continued
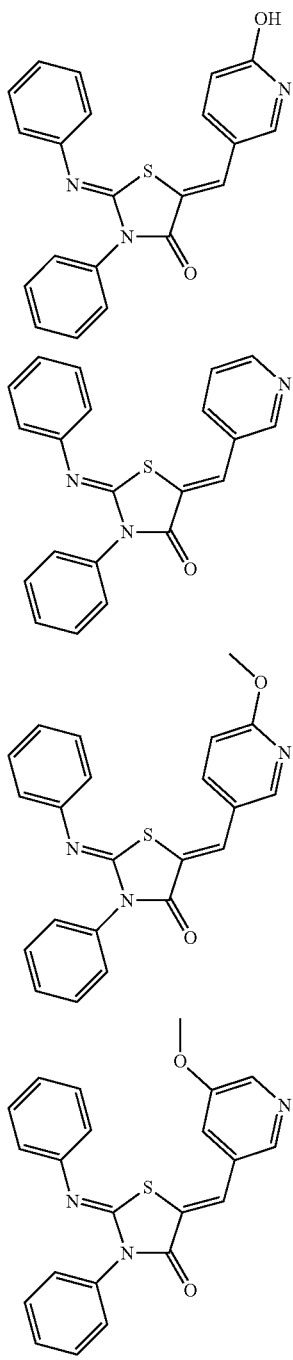
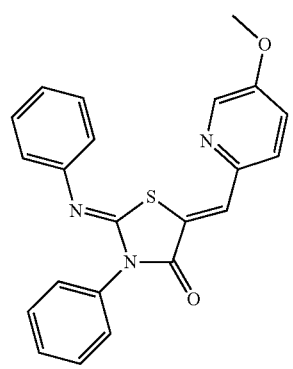 [SMILES: COc1ccc(/C=C2\S/C(=N\c3ccccc3)N(c3ccccc3)C2=O)nc1]

83
-continued
84
-continued
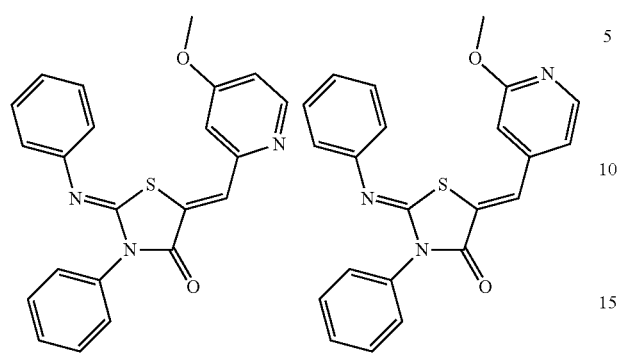
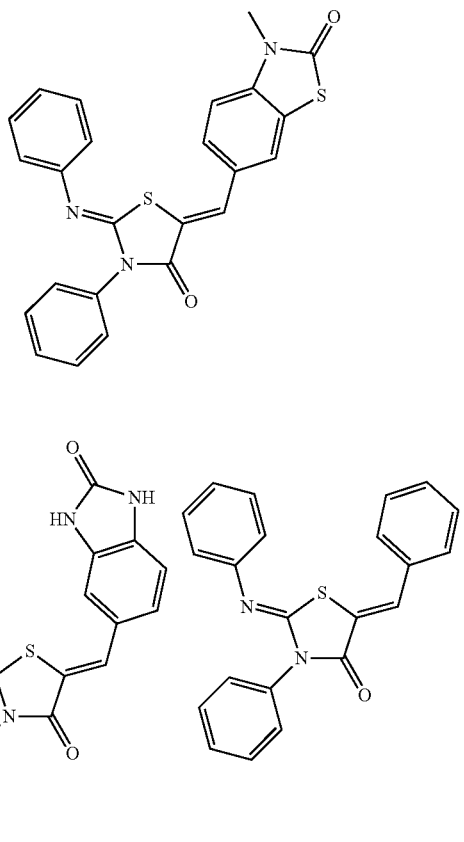
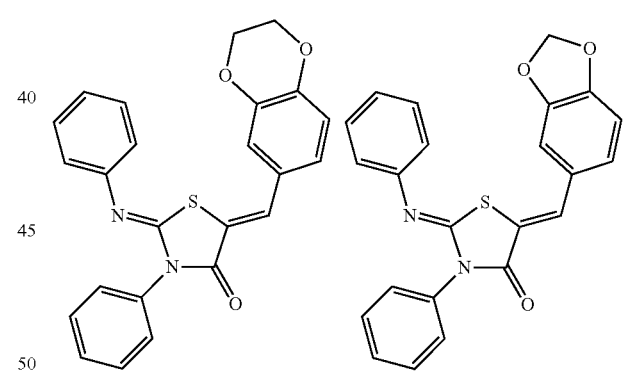
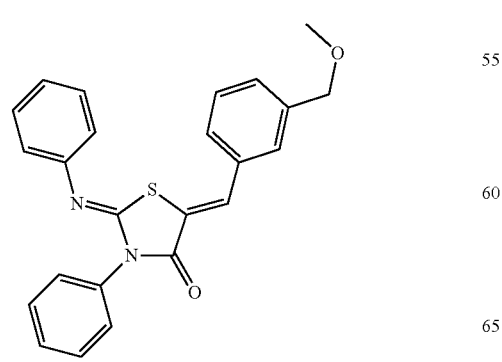
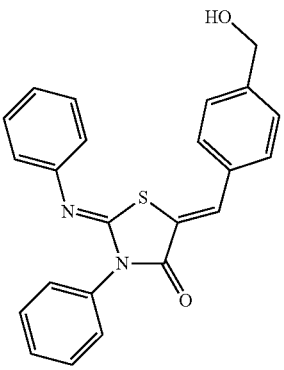 [SMILES: O=C1/C(=C/c2ccc(CO)cc2)S/C(=N\c2ccccc2)N1c1ccccc1]

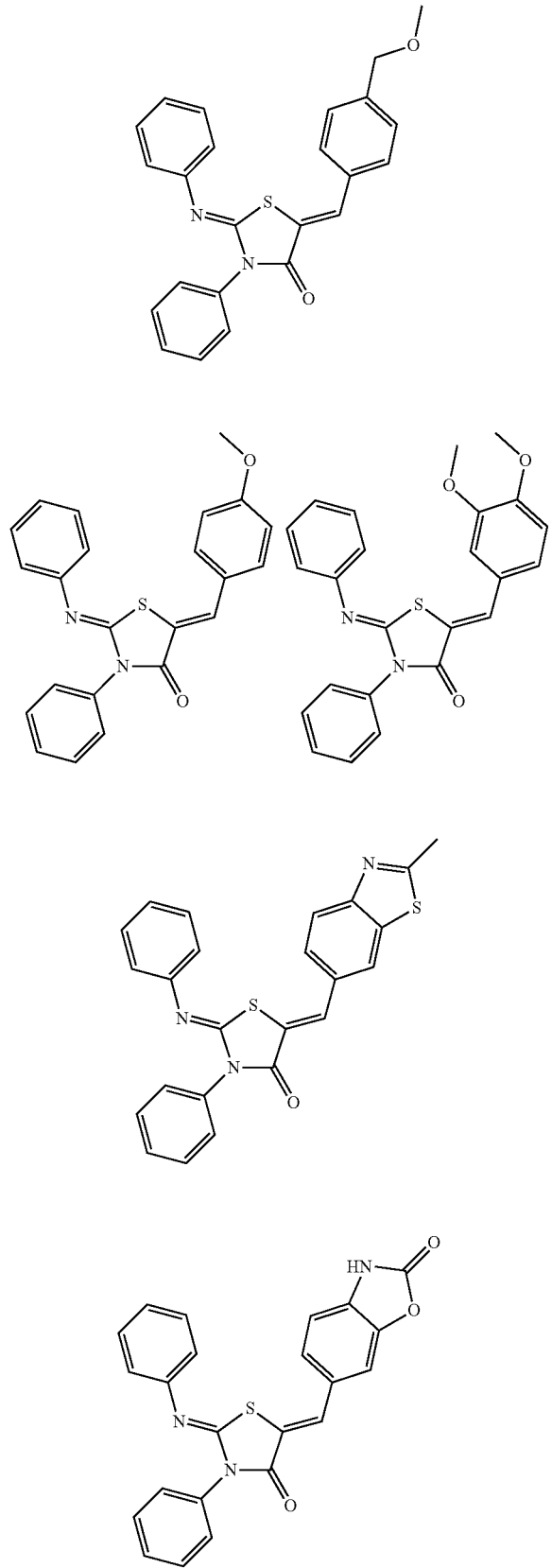
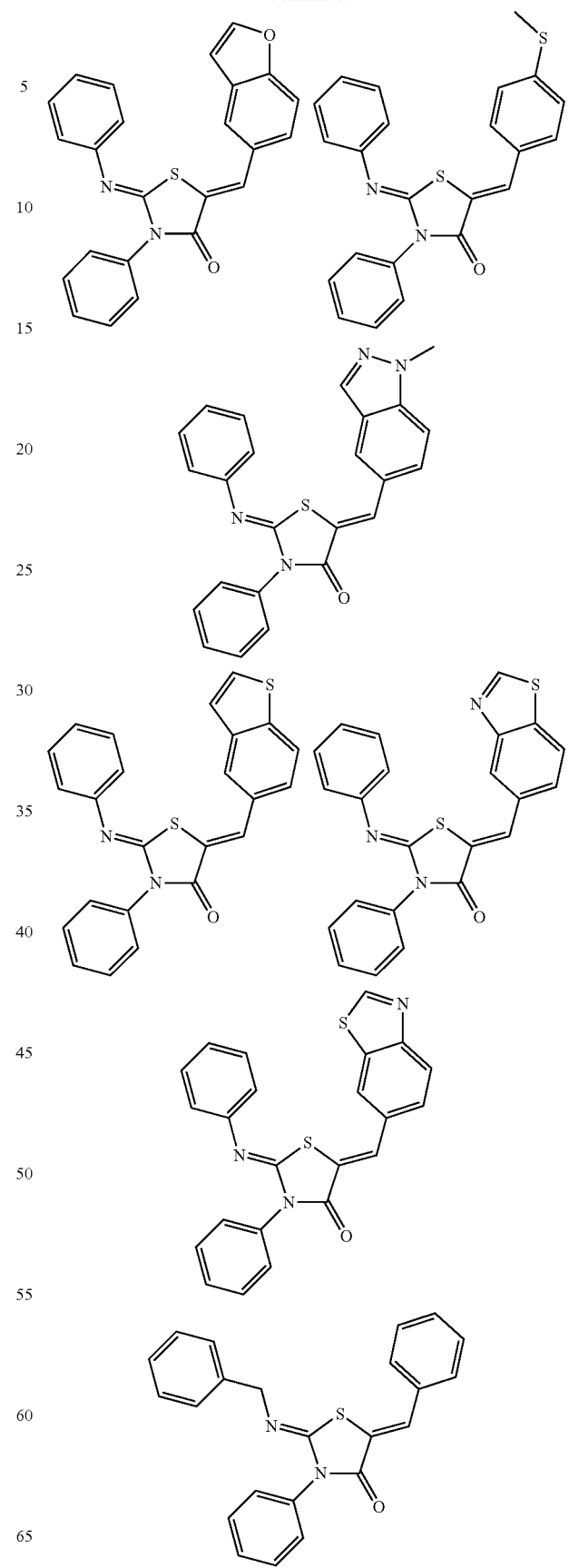

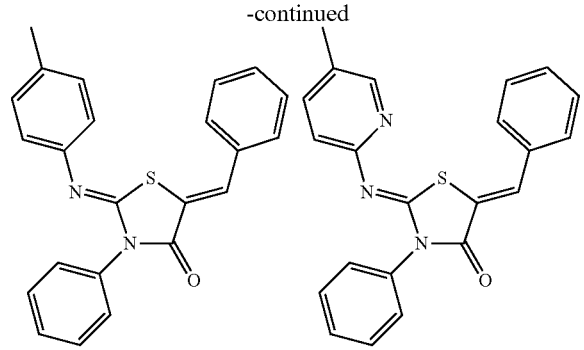
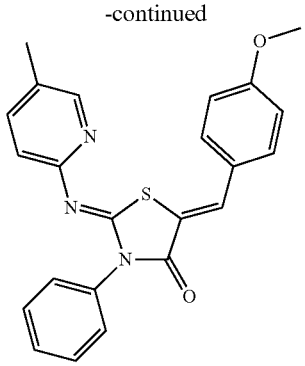
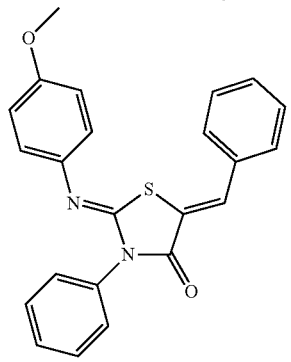 [SMILES: COc1ccc(/N=C2\S/C(=C\c3ccccc3)C(=O)N2c2ccccc2)cc1]
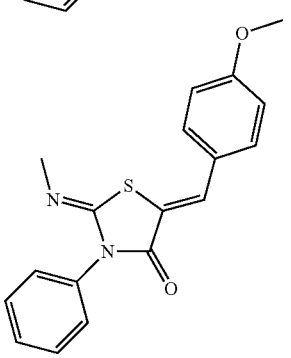
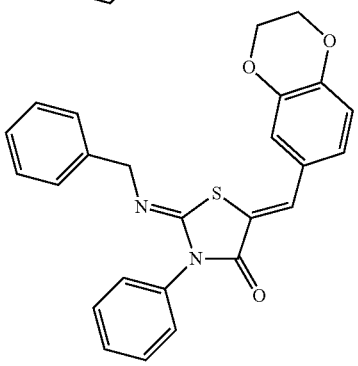
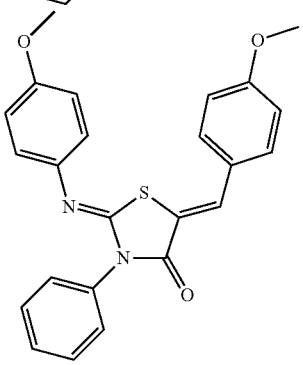
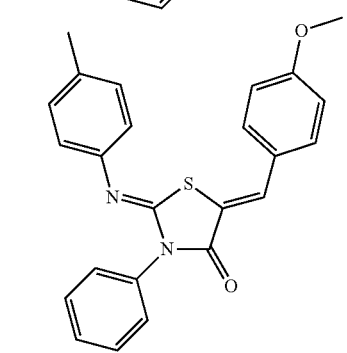
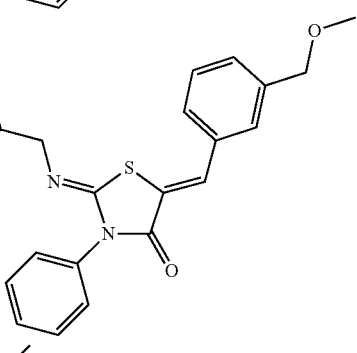
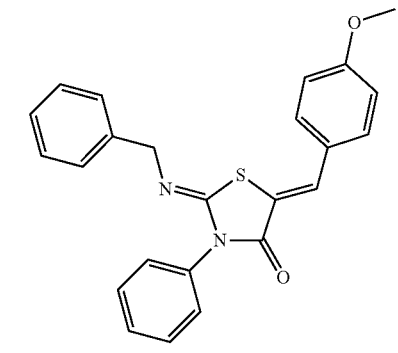
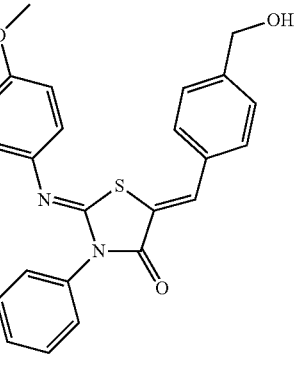

89
-continued
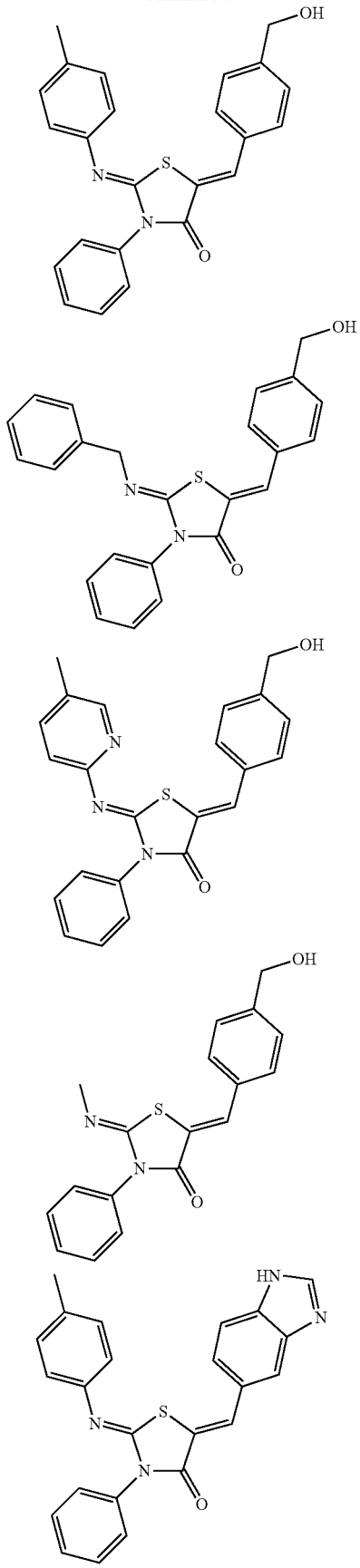
90
-continued
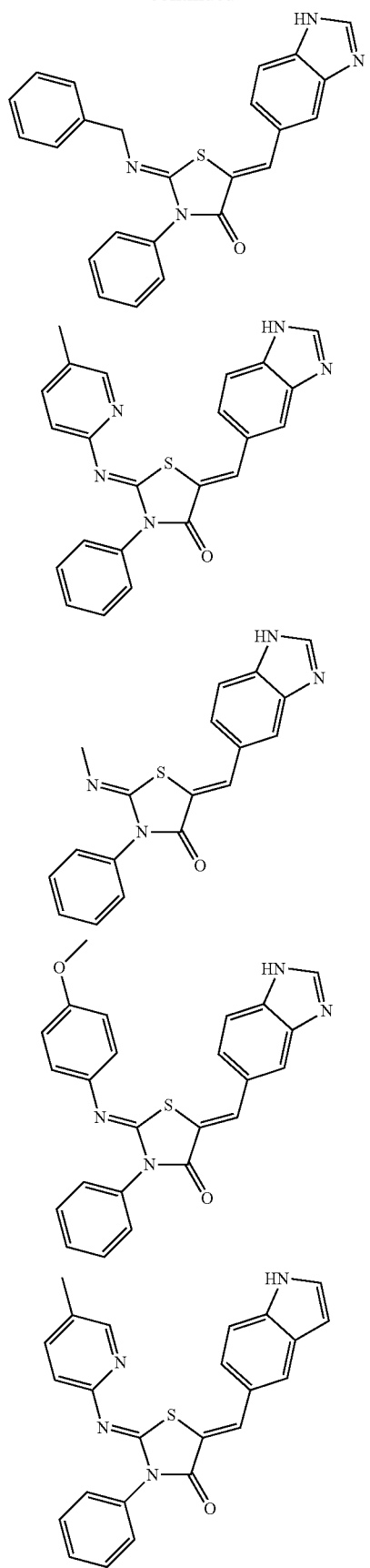

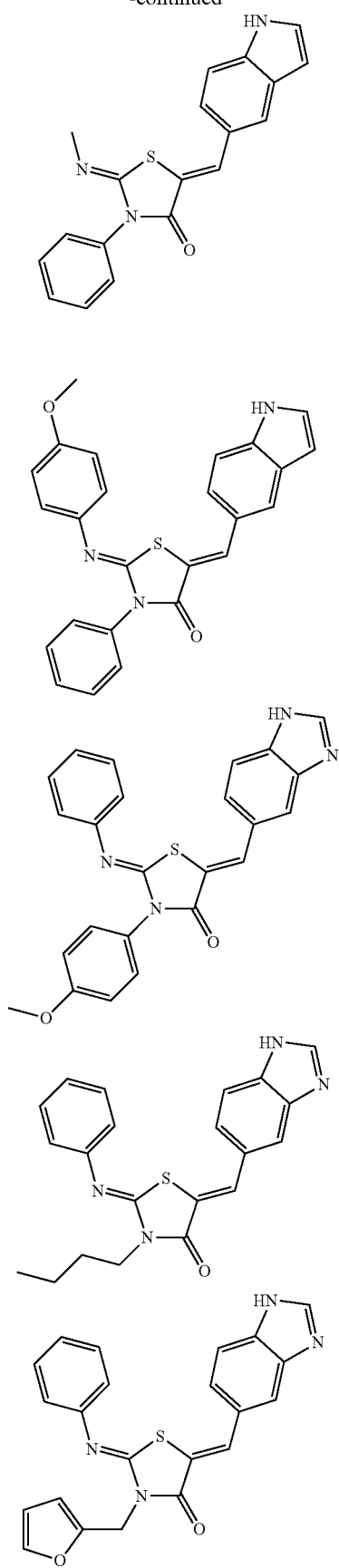
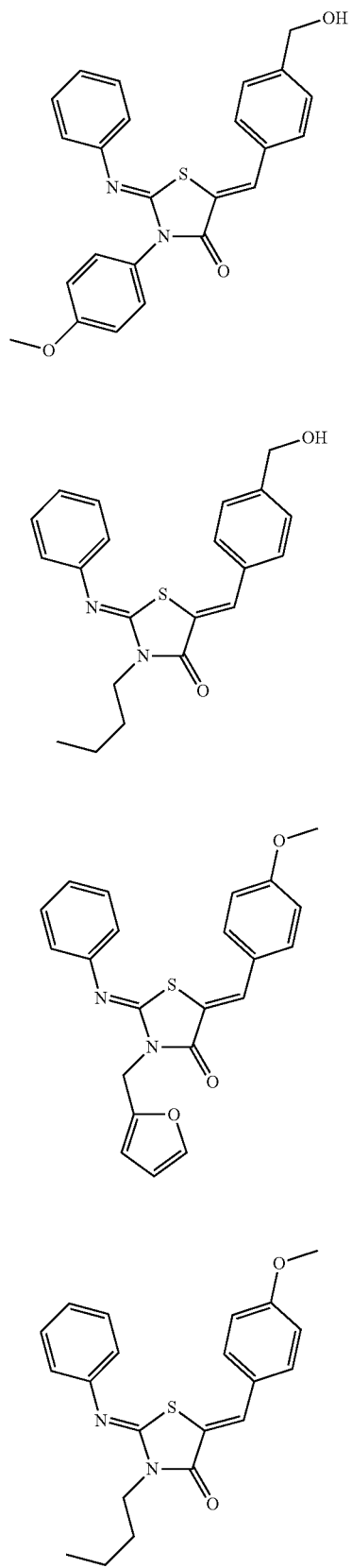

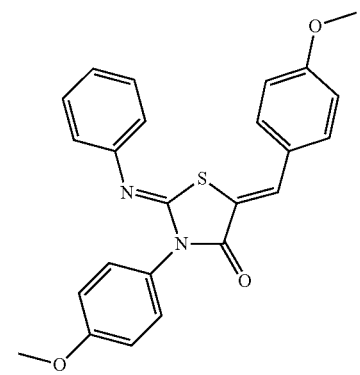
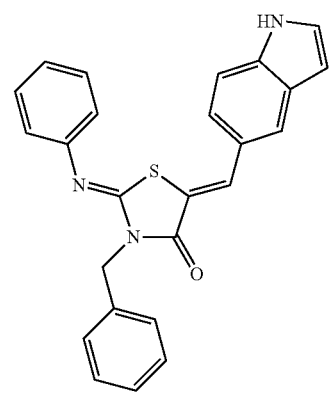 [SMILES: O=C1/C(=C/c2ccc3[nH]ccc3c2)S/C(=N\c2ccccc2)N1Cc1ccccc1]
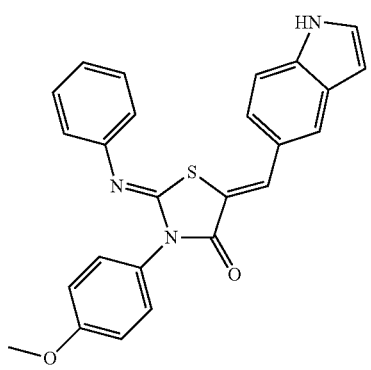
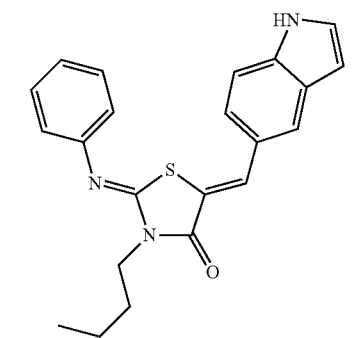 [SMILES: CCCCN1C(=O)/C(=C/c2ccc3[nH]ccc3c2)S/C1=N\c1ccccc1]
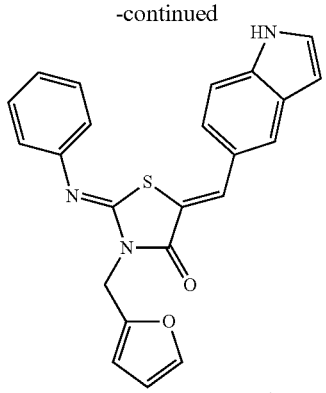
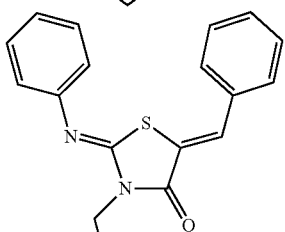
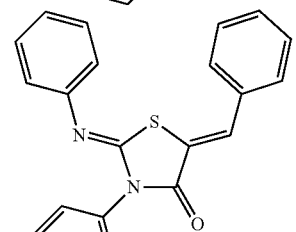
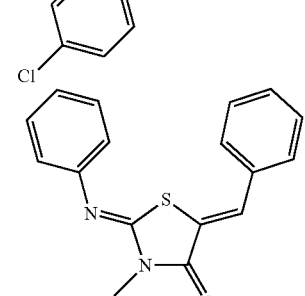
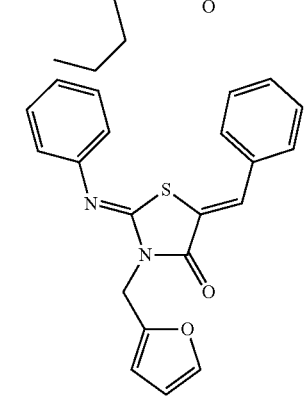
A fifth aspect of the invention relates to a compound according to the first, second, third or fourth aspect of the invention for use as a medicament.

A sixth aspect of the invention relates to a compound according to the first, second, third or fourth aspect of the invention for use in the treatment of psychiatric or neurological disorders and inflammation, in particular neuroinflammation.

A seventh aspect of the invention relates to a pharmaceutical preparation for use in the treatment of psychiatric or neurological disorders and inflammation, in particular neuroinflammation, comprising at least one compound according to the the first, second, third or fourth aspect of the invention.

The compounds of the invention are potent inhibitors of AEA cell membrane transport and do not inhibit the AEA metabolic enzyme FAAH. The compounds of the invention show both cannabimimetic behavioral effects and antiinflammatory effects, in particular an anti-neuroinflammatory effect, as exemplified in the experimental section.

By inhibiting AEA uptake the ECS can be modulated in a unique way, leading to diverse pharmacological actions like analgesia, anti-inflammatory and CNS effects exemplified by the tetrad effect (Nicolussi & Gertsch, 2015, Vitam Horm. 98:441-85).

The use of the compounds of the invention in a method for treatment of psychiatric or neurological disorders is related to attenuation of neuroinflammation and neuronal retrograde signaling mediated via endocannabinoids including AEA. Such diseases include bipolar diseases, schizophrenia, sleeping disorders, multiple sclerosis and Alzheimers disease (Ashton and Moore Acta Psychiatr Scand. 2011, 124, 250-61; Aso and Ferrer I, Front Pharmacol. 2014, 5:37; Correa et al. Vitam Horm. 2009, 81, 207-30.)

In some embodiments, the compounds of the general formula (1) may be isolated in form of salts, in particular in form of pharmaceutically acceptable salts. The same applies to all of the before mentioned embodiments. In some embodiments, the compounds of the general formula (1) may be isolated in form of a tautomer, a hydrate or a solvate.

Such salts are formed, for example, as acid addition salts, preferably with organic or inorganic acids, from compounds of the general formula (1) with a basic nitrogen atom, in particular the pharmaceutically acceptable salts are formed in such a way. Suitable inorganic acids are, without being limited to, halogen acids, such as hydrochloric acid, sulfuric acid, or phosphoric acid and the like. Suitable organic acids are, without being limited to, carboxylic, phosphonic, sulfonic or sulfamic acids and the like. Such organic acids may be, without being limited to, acetic acid, glycolic acid, lactic acid, malic acid, tartaric acid, or citric acid. Salts may also be formed, for example, as salts with organic or inorganic bases, from compounds of the general formula (1) with a nitrogen atom bearing an acidic hydrogen. Examples of suitable cations are—without being limited to—sodium, potassium, calcium or magnesium cations, or cations of organic nitrogen bases, e.g. protonated mono-, di- or tri-(2-hydroxyethyl)amine.

In view of the close relationship between the novel compounds in their free form and those in the form of their salts, any reference to the free compounds hereinbefore and hereinafter is to be understood as referring also to the corresponding salts, as appropriate and expedient. Likewise, in view of the close relationship between the novel compounds of the general formula (1) and their tautomers, any reference to the compounds of the general formula (1) is to be understood as referring also to the corresponding tautomers. The same applies to a hydrate or a solvate.

In some embodiments, the pharmaceutical preparation comprises at least one compound according to the invention as an active ingredient and at least one pharmaceutically acceptable carrier. In some embodiments, the pharmaceutical preparation comprises at least one compound according to the invention in its free form as an active ingredient. In some embodiments, the pharmaceutical preparation comprises at least one compound according to the invention in its free form as an active ingredient and at least one pharmaceutically acceptable carrier.

In some embodiments, the pharmaceutical preparation comprises at least one compound according to the invention in form of a salt, a tautomer, a pharmaceutically acceptable salt, a hydrate or a solvate. In some embodiments, the pharmaceutical preparation comprises at least one compound according to the invention in form of a salt, a tautomer, a pharmaceutically acceptable salt, a hydrate or a solvate and at least one pharmaceutically acceptable carrier.

Furthermore the invention relates to pharmaceutical preparations comprising at least one compound mentioned herein before as active ingredient, which can be used especially in the treatment of the diseases mentioned. The pharmaceutical preparations may be used in particular for a method for treatment of psychiatric disorders.

In some embodiments, the pharmaceutical preparations is for enteral administration, such as nasal, buccal, rectal, local or, especially, oral administration, and for parenteral administration, such as intravenous, intramuscular or subcutaneous administration, are especially preferred. The preparations comprise the active ingredient alone or, in particular, together with a pharmaceutically acceptable carrier. The dosage of the active ingredient depends upon the disease to be treated and upon the species, its age, weight, and individual condition, the individual pharmacokinetic data, and the mode of administration. In particular, the oral application of the active ingredient is preferred.

In some embodiments, the pharmaceutical preparations comprise from approximately 1% to approximately 95% active ingredient. Unit dose forms are, for example, coated and uncoated tablets, ampoules, vials, suppositories, or capsules. Further dosage forms are, for example, ointments, creams, pastes, foams, tinctures, lip-sticks, drops, sprays, dispersions, etc. Examples are capsules containing from about 0.005 g to about 1.0 g active ingredient.

In some embodiments, the pharmaceutical preparations of the present invention are prepared in a manner known per se, for example by means of conventional mixing, granulating, coating, dissolving or lyophilizing processes.

In some embodiments, the pharmaceutical preparations is in form of solutions of the active ingredient, and also suspensions or dispersions, especially isotonic aqueous solutions, dispersions or suspensions which, for example in the case of lyophilized preparations comprising the active ingredient alone or together with a carrier, for example mannitol, can be made up before use.

In some embodiments, the pharmaceutical preparations may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilizing processes.

The said solutions or suspensions may comprise viscosity-increasing agents, typically sodium carboxymethylcellulose, carboxymethylcellulose, dextran, polyvinylpyrrolidone, or gelatins, or also solubilizers, e.g. Tween 80® (polyoxyethylene(20)sorbitan mono-oleate).

In some embodiments, the pharmaceutical preparation comprises suspensions in oil, which comprise as the oil component a vegetable, synthetic, or semi-synthetic oils customary for injection purposes. In some embodiments, the pharmaceutical preparation comprises a mixtures of fatty acid esters, vegetable oils such as, without being limited to, cottonseed oil, almond oil, olive oil, castor oil, sesame oil, soybean oil and groundnut oil. The manufacture of injectable preparations is usually carried out under sterile conditions, as is the filling, for example, into ampoules or vials, and the sealing of the containers.

Suitable carriers are especially fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, also carboxymethyl starch, crosslinked polyvinyl pyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Tablet cores can be provided with suitable, optionally enteric, coatings through the use of, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or tablet coatings, for example for identification purposes or to indicate different doses of active ingredient.

In some embodiments, the pharmaceutical preparation is suitable for oral administration also include hard capsules consisting of gelatin, and also soft, sealed capsules consisting of gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient is preferably dissolved or suspended in suitable liquid excipients, such as fatty oils, paraffin oil or liquid polyethylene glycols or fatty acid esters of ethylene or propylene glycol, to which stabilizers and detergents, for example of the polyoxy ethylene sorbitan fatty acid ester type, may also be added.

In some embodiments, the pharmaceutical preparation is suitable for rectal administration are, for example, suppositories that consist of a combination of the active ingredient and a suppository base. Suitable suppository bases are, for example, natural or synthetic triglycerides, paraffin hydrocarbons, polyethylene glycols or higher alkanols.

In some embodiments, the pharmaceutical preparation is suitable for parenteral administration, aqueous solutions of an active ingredient in water-soluble form or aqueous injection suspensions that contain viscosity-increasing substances, for example sodium carboxymethylcellulose, sorbitol and/or dextran, and, if desired, stabilizers, are especially suitable. The active ingredient, optionally together with excipients, can also be in the form of a lyophilizate and can be made into a solution before parenteral administration by the addition of suitable solvents. Solutions such as are used, for example, for parenteral administration can also be employed as infusion solutions.

Preferred preservatives are, for example, antioxidants, such as ascorbic acid, or microbicides, such as sorbic acid or benzoic acid.

EXAMPLES

General Methods and Materials

Compounds and chemicals were of purest possible grade. Anandamide (AEA), (R)—N-(1-(4-hydroxyphenyl)-2-hydroxyethyl)oleamide (OMDM-2), N-(3-furanylmethyl)-(5Z,8Z,11Z,14Z)-eicosatetraenamide (UCM707), [ethanolamine-1-3H]-AEA (60 Ci/mmol) was purchased from American Radiolabeled Chemicals. Albumin from bovine serum essentially fatty acid free (BSA) (A7030), fetal bovine serum (F7524), RPMI-1640 were purchased from Sigma-Aldrich, Germany. AquaSil™ siliconizing fluid was purchased from Thermo Scientific.

[$^3$H]-AEA Cellular Uptake

Screening for AEA cellular uptake inhibition was performed in a semi-automated procedure: Pipetting and washing steps were performed by a Biomek3000 laboratory workstation. First, required amounts of U937 cells were centrifuged at 100×g for 5 min and resuspended in RPMI (37° C.) to a final concentration of $2 \times 10^6$ cells/mL. Then, 250 µL of cell suspension ($0.5 \times 10^6$ cells per sample) were transferred into AquaSil™ silanized glass vials (Chromacol 1.1-MTV) in 96-well format. After addition of 5 µL vehicle (DMSO) or compounds the cells were incubated at 37° C. for 15 min. As positive controls OMDM-2 and UCM707 were used at 10 µM in each run. The ETI-T compounds were measured at up to 7 concentrations in triplicates from 100 pM-100 µM. After pre-incubation, a mixture of 0.5 nM[ethanolamine-1-$^3$H]-AEA, (60 Ci/mmol) and 99.5 nM of cold AEA (final 100 nM) was added and samples were incubated at 37° C. for another 15 min. The reaction was stopped by rapid filtration over UniFilter-96 GF/C filters (PerkinElmer) pre-soaked with PBS 0.25% BSA. Cells were washed three times with 100 µL ice-cold PBS buffer containing 1% fatty acid free BSA. After drying, 45 µL MicroScint 20 scintillation cocktail (PerkinElmer, Waltham, Mass., US) was added to the wells and the plate was sealed. Radioactivity was measured by liquid scintillation counting on a PerkinElmer Wallac Trilux MicroBeta 1450 during 2 min. Nonspecific binding of [$^3$H]AEA (100 nM) to the glass vials was never higher than 10%. $IC_{50}$ values were calculated by GraphPad® by non-linear regression using the built-in log (inhibitor) vs. response-variable slope (four parameters) function.

FAAH Activity

Hydrolysis of [$^3$H]-AEA by FAAH was determined as previously described in cell homogenates of U937 cells (0.18 mg protein) (Omeir et al., 1999, Biochem Biophys Res Commun, 264, 316-20; Mor et al., 2004, J Med Chem, 47, 4998-5008). Protein amounts of cell homogenates corresponded to $0.5 \times 10^6$ cells (U937), to assure best possible comparability of $IC_{50}$ values as used for the AEA cellular uptake assays. URB597 was used as positive control. Protein quantification was performed using a BCA assay (Thermo Scientific). Enzyme activity was assessed by addition of vehicle or compounds in 10 µL DMSO to 490 µL homogenate in 10 mM Tris HCl, 1 mM EDTA, 0.1% (w/v) BSA fatty acid free, pH=8 and incubation for 15 min at 37° C. After, a mixture of AEA plus [ethanolamine-1-$^3$H]-AEA (0.5 nM) at final 100 nM was added to the homogenates and incubated for 15 min at 37° C. The reaction was stopped by addition of 1 mL ice-cold $CHCl_3$:MeOH (1:1) followed by vigorous vortexing. Phase separation was achieved by centrifugation at 10,000×g at 4° C. for 10 min. Radioactivity of the separated aqueous phase (upper phase) containing [$^3$H-ethanolamine] or [$^3$H-glycerol] was measured by liquid scintillation counting on a Tri-Carb 2100 TR liquid scintillation analyzer after addition of 3.5 mL Ultima Gold scintillation cocktail (PerkinElmer Life Sciences). Results are expressed as hydrolysis of tritium substrate in percent of vehicle treated control. IC$_{50}$ values were calculated by GraphPad®. Data are reported as means of n=3 independent experiments performed in triplicates.

Radioligand CB Receptor Binding

Binding properties of ETI-T compounds to hCB1 or hCB2 receptors were performed as previously reported in a [$^3$H]-CP55,940 displacement assay (Gertsch et al., 2008, Proc Natl Acad Sci 105, 9099-104). WIN 55,212-2 was used as positive control. In brief, 20 µg protein of CHO-K1 hCB$_1$ or hCB$_2$ membrane preparations were thawed on ice and resuspended in a final volume of 500 µL binding buffer (50 mM Tris-HCl, 2.5 mM EDTA, 5 mM MgCl2, 0.5% fatty acid free BSA, pH 7.4) in silanized glass vials. [$^3$H]-CP55,940 (168 Ci/mmol) (PerkinElmer, Waltham, Mass., US) was added to a final concentration of 0.5 nM followed by the addition of competitors or vehicle in 5 µL DMSO. Membrane binding was equilibrated for 2 h at room temperature (25° C.). Samples were filter through a 0.1% polyethylenimine pre-soaked UniFilter®-96 GF/B plate (PerkinElmer) and washed twelve times with 167 µL ice-cold assay-buffer. The plate was dried, bottom sealed and 45 µL MicroScint 20 scintillation cocktail (PerkinElmer) were added before measured on a PerkinElmer 1450 Microbeta TRILUX liquid scintillation counter. Unspecific binding was determined by WIN 55,212-2, 10 µM and subtracted from all values. IC$_{50}$ values.

General Synthesis

The compounds of the invention may be produced according to one of the pathways depicted in scheme 1 or scheme 2. The starting materials may be purchased or produced according to literature procedures.

Scheme 1:

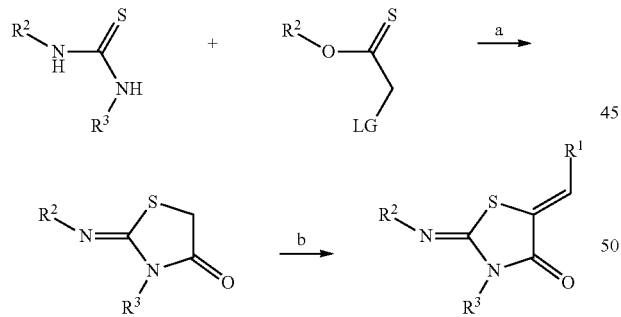

a) solvent, optional a base; b) R$^1$—CH=O, piperidine, EtOH, 18 h or 2 eq. NaOH, AcOH, 60-110° C., 3-24 h (analogue to J. Med.Chem.;2010; 53 (10), 4198 or J. Med. Chem.;2008; 51, 1242), with R being H, methyl or ethyl and LG being a leaving group such as Cl or Br.

Scheme 2:

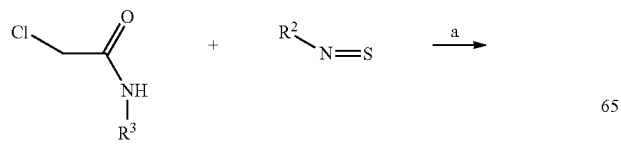

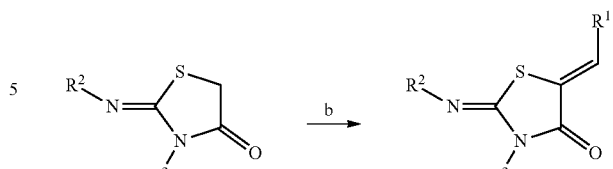

a) solvent, base; b) R$^1$—CH=O, piperidine, EtOH, 18 h or 2 eq. NaOH, AcOh, 60-110° C., 3-24 h (analogue to J. Med.Chem.;2010; 53 (10), 4198 or J. Med. Chem.;2008; 51, 1242).

Evaluation:

TABLE 1

| AEA uptake inhibition | |
|---|---|
| Compound | AEA uptake inhibition IC50 (µM) |
| (structure with indole, phenyl groups) | 0.731 |
| (structure with benzimidazole, phenyl groups) | 0.194 |
| (structure with indole, phenyl groups) | 2.3 |

TABLE 1-continued

AEA uptake inhibition

| Compound | AEA uptake inhibition IC50 (μM) |
|---|---|
| (quinoxalinyl-methylene thiazolidinone with N-phenyl, phenylimino) | 7.1 |
| (6-methoxypyridin-3-yl-methylene thiazolidinone with N-phenyl, phenylimino) | 15.6 |
| (5-methoxypyridin-3-yl-methylene thiazolidinone with N-phenyl, phenylimino) | 6.7 |
| (6-methoxypyridin-2-yl-methylene thiazolidinone with N-phenyl, phenylimino) | 6.6 |

TABLE 1-continued

AEA uptake inhibition

| Compound | AEA uptake inhibition IC50 (μM) |
|---|---|
| (4-methoxypyridin-2-yl-methylene thiazolidinone with N-phenyl, phenylimino) | 1.6 |
| (2-methoxypyridin-4-yl-methylene thiazolidinone with N-phenyl, phenylimino) | 5.5 |
| (3-(methoxymethyl)phenyl-methylene thiazolidinone with N-phenyl, phenylimino) | 1.0 |
| (pyridin-2-yl-methylene thiazolidinone with N-phenyl, phenylimino) | 2.78 |

TABLE 1-continued

AEA uptake inhibition

| Compound | AEA uptake inhibition IC50 (μM) |
|---|---|
| (structure: 2-phenylimino-3-phenyl-5-(2,3-dihydro-1,4-benzodioxin-6-ylmethylene)thiazolidin-4-one) | 0.817 |
| (structure: 2-phenylimino-3-phenyl-5-(benzo[d][1,3]dioxol-5-ylmethylene)thiazolidin-4-one) | 3.36 |
| (structure: 2-phenylimino-3-phenyl-5-(4-(hydroxymethyl)benzylidene)thiazolidin-4-one) | 0.729 |
| (structure: 2-phenylimino-3-phenyl-5-(4-methoxybenzylidene)thiazolidin-4-one) | 2.12 |
| (structure: 2-phenylimino-3-phenyl-5-((2-oxo-2,3-dihydrobenzo[d]oxazol-6-yl)methylene)thiazolidin-4-one) | 5.56 |
| (structure: 2-phenylimino-3-phenyl-5-(benzofuran-5-ylmethylene)thiazolidin-4-one) | 3.26 |
| (structure: 2-phenylimino-3-phenyl-5-(4-(methylthio)benzylidene)thiazolidin-4-one) | 9.94 |
| (structure: 2-phenylimino-3-phenyl-5-((1-methyl-1H-indazol-5-yl)methylene)thiazolidin-4-one) | 0.515 |

TABLE 1-continued

AEA uptake inhibition

| Compound | AEA uptake inhibition IC50 (μM) |
|---|---|
| (structure) | 4.63 |
| (structure) | 11.77 |
| (structure) | 0.291 |
| (structure) | 0.180 |
| (structure) | 3.24 |
| (structure) | 2.34 |
| (structure) | 0.170 |
| (structure) | 5.10 |

TABLE 1-continued

AEA uptake inhibition

| Compound | AEA uptake inhibition IC50 (μM) |
|---|---|
| (structure) | 0.440 |
| (structure) | 2.80 |
| (structure) | 6.92 |
| (structure) | 1.74 |
| (structure) | 1.69 |
| (structure) | 0.135 |
| (structure) | 0.111 |
| (structure) | 0.257 |

TABLE 1-continued

AEA uptake inhibition

| Compound | AEA uptake inhibition IC50 (μM) |
|---|---|
| (5-methylpyridin-2-ylimino, 3-phenyl, 5-(4-hydroxymethylbenzylidene) thiazolidin-4-one) | 1.45 |
| (4-methylphenylimino, 3-phenyl, 5-(1H-benzimidazol-5-ylmethylene) thiazolidin-4-one) | 0.107 |
| (benzylimino, 3-phenyl, 5-(1H-benzimidazol-5-ylmethylene) thiazolidin-4-one) | 2.14 |
| (5-methylpyridin-2-ylimino, 3-phenyl, 5-(1H-benzimidazol-5-ylmethylene) thiazolidin-4-one) | 1.59 |

TABLE 1-continued

AEA uptake inhibition

| Compound | AEA uptake inhibition IC50 (μM) |
|---|---|
| (4-methoxyphenylimino, 3-phenyl, 5-(1H-benzimidazol-5-ylmethylene) thiazolidin-4-one) | 0.164 |
| (5-methylpyridin-2-ylimino, 3-phenyl, 5-(1H-indol-5-ylmethylene) thiazolidin-4-one) | 2.73 |
| (methylimino, 3-phenyl, 5-(1H-indol-5-ylmethylene) thiazolidin-4-one) | 16.6 |
| (4-methoxyphenylimino, 3-phenyl, 5-(1H-indol-5-ylmethylene) thiazolidin-4-one) | 1.07 |

TABLE 1-continued

AEA uptake inhibition

| Compound | AEA uptake inhibition IC50 (μM) |
|---|---|
| (structure: 2-phenylimino-3-benzyl-5-(1H-indol-5-ylmethylene)thiazolidin-4-one) | 0.610 |
| (structure: 2-phenylimino-3-butyl-5-(1H-indol-5-ylmethylene)thiazolidin-4-one) | 0.677 |
| (structure: 2-phenylimino-3-(furan-2-ylmethyl)-5-(1H-indol-5-ylmethylene)thiazolidin-4-one) | 0.879 |
| (structure: 2-phenylimino-3-butyl-5-(1H-benzimidazol-5-ylmethylene)thiazolidin-4-one) | 0.557 |

TABLE 1-continued

AEA uptake inhibition

| Compound | AEA uptake inhibition IC50 (μM) |
|---|---|
| (structure: 2-phenylimino-3-(furan-2-ylmethyl)-5-(1H-benzimidazol-5-ylmethylene)thiazolidin-4-one) | 1.84 |
| (structure: 2-phenylimino-3-benzyl-5-(4-hydroxymethylbenzylidene)thiazolidin-4-one) | 0.657 |
| (structure: 2-phenylimino-3-(furan-2-ylmethyl)-5-(4-hydroxymethylbenzylidene)thiazolidin-4-one) | 1.31 |
| (structure: 2-phenylimino-3-butyl-5-(4-hydroxymethylbenzylidene)thiazolidin-4-one) | 1.09 |

TABLE 1-continued

AEA uptake inhibition

| Compound | AEA uptake inhibition IC50 (μM) |
|---|---|
| (structure) | 5.42 |
| (structure) | 4.15 |
| (structure) | 1.81 |
| (structure) | 2.29 |
| (structure) | 7.18 |
| (structure) | 2.27 |
| (structure) | 3.18 |

TABLE 2

AEA uptake inhibition of further compounds

| ETI-T-compound | AEA uptake IC50 (μM) |
|---|---|
| 24_Q_B | 0.033 |
| 24_Q_I | 0.035 |
| 24_P_L | 0.051 |
| 24_Q_L | 0.085 |
| 24_P_I | 0.087 |
| 24_Q_X | 0.137 |
| 24_A_B | 0.138 |
| 24_B_I | 0.141 |
| 24_B_X | 0.162 |
| 24_Q_A | 0.164 |
| 24_B_B | 0.170 |

TABLE 2-continued

AEA uptake inhibition of further compounds

| ETI-T-compound | AEA uptake IC50 (μM) |
| --- | --- |
| 24_C_N | 0.170 |
| 24_N_X | 0.172 |
| 24_B_A | 0.176 |
| 24_P_A | 0.176 |
| 24_A_A | 0.286 |
| 24_A_I | 0.301 |
| 24_N_A | 0.334 |
| 24_Q_N | 0.373 |
| 24_B_N | 0.419 |
| 24_N_I | 0.462 |
| 24_P_X | 0.509 |
| 24_P_N | 0.53 |
| 24_A_L | 0.616 |
| 24_B_L | 0.663 |
| 24_N_B | 0.667 |
| 24_A_X | 0.721 |
| 24 | 0.817 |
| 24_F_N | 0.939 |
| 24_P_B | 1.043 |
| 24_S_N | 1.43 |
| 24_A_N | 1.510 |
| 24_K_N | 1.620 |

TABLE 3

FAAH inhibition of further compounds

| ETI-T-compound | FAAH inhibition IC50 (pM) |
| --- | --- |
| 24_Q_B | 1.288 |
| 24_Q_I | 0.037 |
| 24_P_L | 0.617 |
| 24_Q_L | 0.813 |
| 24_P_I | 0.170 |
| 24_Q_X | 0.427 |
| 24_B_I | >100 |
| 24_B_X | >100 |
| 24_Q_A | >100 |
| 24_B_B | >100 |
| 24_C_N | 1.585 |
| 24_N_X | >100 |
| 24_P_A | 1.514 |
| 24_A_A | >100 |
| 24_A_I | >100 |
| 24_N_A | >100 |
| 24_Q_N | 0.437 |
| 24_N_I | >100 |
| 24_P_X | 2.63 |
| 24_P_N | 0.912 |
| 24_N_B | >100 |
| 24 | >100 |
| 24_F_N | >100 |
| 24_P_B | 11.22 |
| 24_C_B | >100 |
| 24_C_C | >100 |
| 24_C_F | >100 |
| 22_B_I | >100 |

TABLE 4

CB1 receptor binding of further compounds

| ETI-T-compound | CB1 receptor binding % at 10 μM |
| --- | --- |
| 24_Q_B | 45 |
| 24_Q_I | 47 |

TABLE 4-continued

CB1 receptor binding of further compounds

| ETI-T-compound | CB1 receptor binding % at 10 μM |
| --- | --- |
| 24_P_L | 41 |
| 24_Q_L | 44 |
| 24_P_I | 61 |
| 24_A_B | 29 |
| 24_B_I | 42 |
| 24_B_X | 78 |
| 24_Q_A | 74 |
| 24_B_B | 3 |
| 24_C_N | 68 |
| 24_N_X | 43 |
| 24_B_A | 32 |
| 24_P_A | 83 |
| 24_A_A | 30 |
| 22B_I | 42 |
| 24_A_I | 58 |
| 24_N_A | 80 |
| 24_Q_N | 26 |
| 24_B_N | 53 |
| 24_N_I | 82 |
| 24_P_X | 78 |
| 24_P_N | 52 |
| 24_A_L | 67 |
| 24_B_L | 63 |
| 24_N_B | 86 |
| 24_A_X | 54 |
| 24 | 1 |
| 24_P_B | 50 |
| 24_S_N | 56 |
| 24_K_N | 78 |

TABLE 5

AEA uptake inhibition of further compounds

| ETI-T-compound | AEA uptake IC50 (μM) |
| --- | --- |
| 04_A_N | 0.107 |
| 04_B_I | 0.132 |
| 04_K_N | 0.142 |
| 04_A_X | 0.155 |
| 04_F_N | 0.164 |
| 04 | 0.194 |
| 03_T_N | 0.262 |
| 32 | 0.291 |
| 03_A_A | 0.315 |
| 32_A_X | 0.327 |
| 32_A_I | 0.341 |
| 28_A_X | 0.351 |
| 28_A_I | 0.389 |
| 04_A_A | 0.390 |
| 03_P_N | 0.403 |
| 03_B_X | 0.479 |
| 04_C_F | 0.484 |
| 03_U_N | 0.509 |
| 28 | 0.515 |
| 04_B_A | 0.527 |
| 04_N_G | 0.557 |
| 03_C_K | 0.564 |
| 03_N_K | 0.564 |
| 04_B_X | 0.578 |
| 03_N_C | 0.610 |
| 32_B_A | 0.632 |
| 03_N_G | 0.677 |
| 03_C_O | 0.727 |
| 04_N_K | 0.727 |
| 03 | 0.731 |
| 03_B_A | 0.760 |
| 04_C_B | 0.861 |
| 04_S_N | 0.878 |
| 03_N_M | 0.879 |

TABLE 5-continued

AEA uptake inhibition of further compounds

| ETI-T-compound | AEA uptake IC50 (µM) |
|---|---|
| 32_B_X | 0.993 |
| 04_P_N | 1.020 |
| 04_C_G | 1.060 |
| 03_F_N | 1.070 |
| 04_C_O | 1.120 |
| 04_C_K | 1.140 |
| 04_U_N | 1.4 |
| 04_D_N | 1.590 |

TABLE 6

FAAH inhibition of further compounds

| ETI-T-compound | FAAH inhibition IC50 (µM) |
|---|---|
| 04_A_N | >100 |
| 04_B_I | 22.909 |
| 04_K_N | >100 |
| 04_A_X | 14.454 |
| 04_F_N | >100 |
| 04 | >100 |
| 03_T_N | >100 |
| 32 | >100 |
| 03_A_A | >100 |
| 32_A_X | >100 |
| 32_A_I | >100 |
| 28_A_X | >100 |
| 28_A_I | >100 |
| 04_A_A | >100 |
| 03_P_N | <10 |
| 03_B_X | >100 |
| 04_C_F | >10 |

TABLE 7

CB1 receptor binding of further compounds

| ETI-T-compound | CB1 receptor binding % at 10 µM |
|---|---|
| 04_A_N | 71 |
| 04_B_I | 43 |
| 04_K_N | 80 |
| 04_A_X | 27 |
| 04_F_N | 55 |
| 04 | 43 |
| 03_T_N | 36 |
| 32 | 37 |
| 03_A_A | 57 |
| 32_A_X | 55 |
| 32_A_I | 43 |
| 28_A_X | 51 |
| 28_A_I | 31 |
| 04_A_A | 49 |
| 03_P_N | 71 |
| 03_B_X | 46 |
| 04_C_F | 27 |

TABLE 8

AEA uptake inhibition of further compounds

| ETI-T-compound | AEA uptake IC50 (µM) |
|---|---|
| 22_K_N | 0.097 |
| 22_A_N | 0.111 |
| 22_B_X | 0.127 |
| 22_F_N | 0.135 |
| 22_A_X | 0.150 |
| 22_A_A | 0.341 |
| 15_Q_N | 0.368 |
| 22_B_A | 0.386 |
| 22_P_N | 0.500 |
| 22_C_F | 0.592 |
| 22_N_C | 0.657 |
| 15_C_K | 0.692 |
| 22_Q_N | 0.713 |
| 22 | 0.729 |
| 22_U_N | 0.812 |
| 22_N_K | 0.861 |
| 15 | 1.030 |
| 22_N_G | 1.090 |
| 22_C_O | 1.200 |
| 22_C_G | 1.280 |
| 22_N_M | 1.310 |
| 22_C_K | 1.430 |
| 22_D_N | 1.450 |
| 15_C_O | 1.560 |
| 22_C_N | 1.660 |
| 15_C_N | 1.690 |
| 22_C_B | 2.170 |
| 15_T_N | 2.640 |
| 22_R_N | 5.180 |
| 22_C_C | 10.420 |
| 23_A_V | 10.500 |
| 22_B_V | 12.540 |
| 15_U_N | 15.550 |
| 34 | >10 |
| 04_A_V | >10 |
| 15_R_N | >10 |
| 22_A_V | >10 |
| 22_E_N | >10 |
| 22_N_F | >10 |
| 22_T_N | >10 |

Table 9 and 10—FAAH Inhibition and CB1 Receptor Binding of Further Compounds

| ETI-T-compound | FAAH inhibition IC50 (µM) |
|---|---|
| 22_K_N | 6.607 |
| 22_A_N | 19.498 |
| 22_B_X | 19.055 |
| 22_F_N | >100 |
| 22_A_X | >100 |
| 22_A_A | >100 |
| 15_Q_N | <10 |
| 22_B_A | >100 |

| ETI-T-compound | CB1 receptor binding % at 10 µM |
|---|---|
| 22_K_N | 63 |
| 22_A_N | 71 |
| 22_B_X | 70 |
| 22_F_N | 33 |
| 22_A_X | 41 |
| 22_A_A | 50 |

-continued

| ETI-T-compound | CBI receptor binding % at 10 μM |
|---|---|
| 15_Q_N | 27 |
| 22_B_A | 24 |

TABLE 11

AEA uptake inhibition, FAAH inhibition andCB1 receptor binding of further compounds

| ETI-T-compound | AEA uptake IC50 (μM) | ETI-T-compound | FAAH inhibition IC50 (μM) | ETI-T-compound | CB1 receptor binding % at 10 μM |
|---|---|---|---|---|---|
| 23_C_N | 0.180 | 23_C_N | >10 | 23_C_N | 75 |
| 23_T_N | 0.556 | | | | |
| 23_Q_N | 0.598 | | | | |
| 23_C_G | 0.753 | | | | |
| 23_N_K | 1.120 | | | | |
| 23_B_X | 1.132 | | | | |
| 23_C_O | 1.190 | | | | |

We claim:

1. A compound of formula (1):

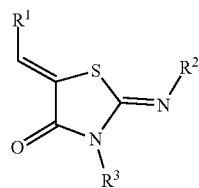

or an (E,E), (E,Z), (Z,E), or (Z,Z) stereoisomer thereof, wherein:
R$^1$ is formula (6b):

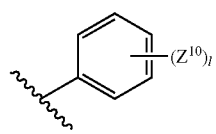

wherein:
each Z$^{10}$ is independently selected from —F, —Cl, —Br, —I, —CN, —R$^e$, —(CH$_2$)$_r$OR$^e$, —(CH$_2$)$_r$SR$^e$, —N(R$^e$)$_2$, —OR$^e$, or —SR$^e$;
each R$^e$ is independently selected from H, an unsubstituted C$_1$-C$_{12}$-alkyl, an unsubstituted C$_2$-C$_{12}$-alkenyl, or an unsubstituted C$_2$-C$_{12}$-alkynyl;
l is 1, 2, 3, 4, or 5; and
r is 1, 2, 3, or 4;
R$^2$ is a substituted or unsubstituted aryl, wherein the substituted aryl is substituted by at least one Z$^2$;
each Z$^2$ is independently selected from —F, —Cl, —Br, —I, —CN, —R$^b$, —(CH$_2$)$_r$OR$^b$, —(CH$_2$)$_r$SR$^b$, —N(R$^b$)$_2$, —OR$^b$, or —SR$^b$;
each R$^b$ is independently selected from H, an unsubstituted C$_1$-C$_{12}$-alkyl, an unsubstituted C$_2$-C$_{12}$-alkenyl, or an unsubstituted C$_2$-C$_{12}$-alkynyl; and r is 1, 2, 3, or 4; and
R$^3$ is selected from an unsubstituted alkyl, an unsubstituted alkenyl, an unsubstituted alkynyl, an unsubstituted alkoxy, an unsubstituted cycloalkyl, a substituted or unsubstituted aryl, an unsubstituted saturated heterocyclyl, or a substituted or unsubstituted heteroaryl, wherein the substituted aryl or the substituted heteroaryl is substituted by at least one Z$^3$;
each Z$^3$ is independently selected from —F, —Cl, —Br, —I, —CN, —R$^d$, —(CH$_2$)$_r$OR$^d$, —(CH$_2$)$_r$SR$^d$, —N(R$^d$)$_2$, —OR$^d$, or —SR$^d$;
each R$^d$ is independently selected from H, an unsubstituted C$_1$-C$_{12}$-alkyl, an unsubstituted C$_2$-C$_{12}$-alkenyl, or an unsubstituted C$_2$-C$_{12}$-alkynyl; and
r is 1, 2, 3, or 4; or
R$^3$ is formula:

-D-Ar, wherein:
D is an alkyl, an alkenyl, or an alkynyl; and
Ar is a substituted or unsubstituted C$_6$ aryl or a substituted or unsubstituted C$_5$-C$_6$ heteroaryl, wherein the substituted C$_6$ aryl or substituted C$_5$-C$_6$ heteroaryl is substituted by at least one Z$^3$;
each Z$^3$ is independently selected from —F, —Cl, —Br, —I, —CN, —R$^d$, —(CH$_2$)$_r$OR$^d$, —(CH$_2$)$_r$SR$^d$, —N(R$^d$)$_2$, —OR$^d$, or —SR$^d$;
each R$^d$ is independently selected from H, an unsubstituted C$_1$-C$_{12}$-alkyl, an unsubstituted C$_2$-C$_{12}$-alkenyl, or an unsubstituted C$_2$-C$_{12}$-alkynyl; and
r is 1, 2, 3, or 4;
with the proviso that at least one Z$^{10}$ is —(CH$_2$)$_r$OR$^e$.

2. The compound according to claim 1, or an (E,E), (E,Z), (Z,E), or (Z,Z) stereoisomer thereof, wherein:
each Z$^{10}$ is independently selected from —F, —Cl, —CN, —R$^e$, —CH$_2$OR$^e$, —N(R$^e$)$_2$, or —OR$^e$;
R$^3$ is selected from substituted aryl or substituted heteroaryl; and
each Z$^3$ is independently selected from —F, —Cl, —Br, —I, —CN, —CH$_2$OR$^d$, or —OR$^d$.

3. The compound according to claim 1, or an (E,E), (E,Z), (Z,E), or (Z,Z) stereoisomer thereof, wherein:
Z$^{10}$ is —(CH$_2$)$_r$OR$^e$;
R$^e$ is selected from H or unsubstituted CH$_3$;
l is 1;
r is 1, 2, or 3; and
Z$^{10}$ is bonded to the meta position.

4. The compound according to claim 1, or an (E,E), (E,Z), (Z,E), or (Z,Z) stereoisomer thereof, wherein R$^2$ is a substituted or unsubstituted C$_6$-C$_{10}$ aryl.

5. The compound according to claim 1, or an (E,E), (E,Z), (Z,E), or (Z,Z) stereoisomer thereof, wherein R$^2$ is formula (4b):

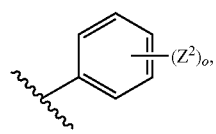

wherein:
o is 0.

6. The compound according to claim 1, or an (E,E), (E,Z), (Z,E), or (Z,Z) stereoisomer thereof, wherein R² is formula (4b):

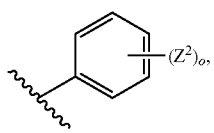

(4b)

wherein:
o is 1, 2, 3, 4, or 5.

7. The compound according to claim 6, or an (E,E), (E,Z), (Z,E), or (Z,Z) stereoisomer thereof, wherein each Z² is independently selected from —F, —Cl, —Br, —I, —CN, —R$^b$, —CH$_2$OR$^b$, —N(R$^b$)$_2$, or —OR$^b$.

8. The compound according to claim 1, or an (E,E), (E,Z), (Z,E), or (Z,Z) stereoisomer thereof, wherein:
R³ is selected from an unsubstituted alkyl, an unsubstituted alkenyl, an unsubstituted alkynyl, an unsubstituted cycloalkyl, a substituted or unsubstituted aryl, or a substituted or unsubstituted heteroaryl; or
R³ is formula:
-D-Ar.

9. The compound according to claim 1, or an (E,E), (E,Z), (Z,E), or (Z,Z) stereoisomer thereof, wherein:
R³ is selected from an unsubstituted $C_1$-$C_4$ alkyl, an unsubstituted $C_2$-$C_4$ alkenyl, an unsubstituted $C_2$-$C_4$ alkynyl, an unsubstituted cyclohexyl, a substituted or unsubstituted phenyl, or a substituted or unsubstituted $C_5$-$C_6$ heteroaryl; or
R³ is formula:
-D-Ar.

10. The compound according to claim 9, or an (E,E), (E,Z), (Z,E), or (Z,Z) stereoisomer thereof, wherein R³ is selected from an unsubstituted cyclohexyl or a substituted or unsubstituted $C_5$-$C_6$ heteroaryl.

11. The compound according to claim 1, or an (E,E), (E,Z), (Z,E), or (Z,Z) stereoisomer thereof, wherein:
R³ is selected from a substituted or unsubstituted phenyl or a substituted or unsubstituted $C_5$-$C_6$ heteroaryl; or
R³ is formula:
-D-Ar.

12. The compound according to claim 1, or an (E,E), (E,Z), (Z,E), or (Z,Z) stereoisomer thereof, wherein:
R³ is formula (5a):

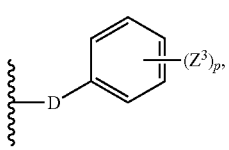

(5a)

wherein:
p is 0, 1, 2, 3, 4, or 5; or
R³ is formula (5b):

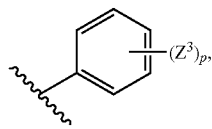

(5b)

wherein:
p is 0, 1, 2, 3, 4, or 5.

13. The compound according to claim 12, or an (E,E), (E,Z), (Z,E), or (Z,Z) stereoisomer thereof, wherein
each Z³ is independently selected from —F, —Cl, —Br, —I, —CN, —R$^d$, —CH$_2$OR$^d$, —N(R$^d$)$_2$, or —OR$^d$.

14. The compound according to claim 1, or an (E,E), (E,Z), (Z,E), or (Z,Z) stereoisomer thereof, wherein
R³ is an unsubstituted $C_3$-$C_{10}$ cycloalkyl.

15. The compound according to claim 1, wherein the compound is a stereoisomer of formula (1a):

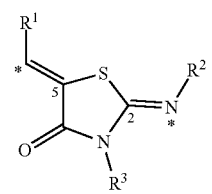

(1a)

wherein the stereoisomer represented by (2*,5*) is selected from the group consisting of (2E,5E), (2E,5Z), (2Z,5E), and (2Z,5Z).

16. A method for inhibiting N-arachidonoylethanolamine uptake in a subject, comprising administering to a subject in need thereof a therapeutically effective amount of a compound according to claim 1.

17. The method according to claim 16, wherein the subject has a disorder selected from the group consisting of a psychiatric disorder, a neurological disorder, and neuroinflammation.

18. A method for modulating an endocannabinoid system in a subject, comprising administering to a subject in need thereof a therapeutically effective amount of a compound according to claim 1.

19. The method according to claim 18, wherein modulation of the endocannabinoid system inhibits N-arachidonoylethanolamine uptake.

* * * * *